US005597922A

United States Patent [19]
Cai et al.

[11] Patent Number: 5,597,922
[45] Date of Patent: Jan. 28, 1997

[54] GLYCINE RECEPTOR ANTAGONIST PHARMACOPHORE

[75] Inventors: Sui X. Cai, Irvine, Calif.; John F. W. Keana, Eugene, Oreg.; Eckard Weber, Laguna Beach, Calif.

[73] Assignees: State of Oregon, Acting by and through the Oregon State Board of Higher Education, Acting for and on Behalf of the Oregon Health Sciences University and the University of Oregon, Eugene, Oreg.; Acea Pharmaceuticals, Inc., Irvine; The Regents of the University of California, Oakland, both of Calif.

[21] Appl. No.: 281,995

[22] Filed: Jul. 29, 1994

[51] Int. Cl.$^6$ ............... C07D 241/44; C07D 265/36; A61K 31/495; A61K 31/535

[52] U.S. Cl. ............ 544/354; 540/491; 540/507; 540/523; 544/1; 544/94; 544/105; 544/234; 544/285; 544/344; 544/355; 546/13; 546/153; 546/157; 546/158; 548/306.4; 548/483; 548/485; 548/486; 548/492; 562/455; 564/44; 564/441; 564/442

[58] Field of Search ............................................. 544/354

[56] References Cited

U.S. PATENT DOCUMENTS

| | | | |
|---|---|---|---|
| 3,816,470 | 6/1974 | Tronche | 544/376 X |
| 3,898,214 | 8/1975 | Vogt | 540/523 |
| 3,904,603 | 9/1975 | Kim | 540/569 |
| 3,925,361 | 12/1975 | Kim | 540/569 |
| 3,985,731 | 10/1976 | Vogt | 540/523 X |
| 4,297,491 | 10/1981 | Reissenweber et al. | 544/105 |
| 4,307,091 | 12/1981 | Brown et al. | 424/248.4 |
| 4,405,513 | 9/1983 | Brown et al. | 424/272 |
| 4,477,446 | 10/1984 | Jones et al. | 540/523 X |
| 5,026,704 | 6/1991 | Honore et al. | 514/250 |
| 5,198,461 | 3/1993 | Wätjen et al. | 514/411 |
| 5,308,844 | 5/1994 | Rieu et al. | 514/230.5 |

FOREIGN PATENT DOCUMENTS

| | | |
|---|---|---|
| 0072352 | 2/1983 | European Pat. Off. . |
| 0130538 | 1/1985 | European Pat. Off. . |
| 0362942 | 4/1990 | European Pat. Off. . |
| 0444924 | 9/1991 | European Pat. Off. . |
| 0463810 | 1/1992 | European Pat. Off. . |
| 1932455 | 9/1970 | Germany . |
| 2944696 | 5/1981 | Germany . |
| 57-183761 | 12/1982 | Japan . |
| 1247554 | 9/1971 | United Kingdom . |
| 1460936 | 1/1977 | United Kingdom . |
| WO94/00124 | 1/1994 | WIPO . |
| WO94/07500 | 4/1994 | WIPO . |
| WO9426747 | 11/1994 | WIPO . |

OTHER PUBLICATIONS

*Advanced Organic Chemistry* by Jerry March pp. 20–22 (1977).

Akssira et al., "Nouvelle Application Des Anhydrides N–Carboxy Aminoacides: Synthese Des 1,4–Benzodiazepine–2,5–Diones," *Tetrahedron Lett.* 33(14):1887–1888 (1992).

Alimov, E. and Tadzhiddinov, Z., "Synthesis of potentially biologically active compounds," *Chem. Abstracts* 85:545 Abstract No. 192615d (1976).

Bauer et al., "Benzodiazepines with Psychotropic Activity. 7. Synthesis and Biological Action of 4–Amino–1,5–benzodiazepines," *J. Med. Chem.* 16(9):1011–1014 (1973).

Bellamy, F. D. and Ou, K., "Selective Reduction of Aromatic Nitro Compounds with Strannous Chloride in Non Acidic and Non Aqueous Medium," *Tetrahedron Lett.* 25(8):839–842 (1984).

Bigge, C. F., "Structural Requirements for the Development of Potent N–Methyl–D–Aspartic Acid (NMDA) Receptor Antagonists," *Biochemical Pharmacol.* 45(8):1547–1561 (1993).

Bonsignore et al., "Novel Reactions of Carbon Suboxide. Synthesis of 1,5–Benzodioxepins, 1,5–Benzoxathiepins and 1,5–Benzoxazepins (1)," *J. Heterocyclic Chem.* 19:1241–1242 (1982).

Bonsignore et al., "Synthesis and Anti–Microbial Activity of Benzo–Condensed Heterocyclic Derivatives," *Il Farmaco* 45(11):1245–1250 (1990).

Buckle et al., "Synthesis and Antiallergic Activity of 2–Hydroxy–3–nitro–1,4–naphthoquinones," *J. Med. Chem.* 20(8):1059–1064 (1977).

Burrell et al., "Quinoxaline Precursors of Fungitoxic Benzimidazolylcarbamates: Syntheses and Photochemically–induced Transformations," *J. Chem. Soc. Perkin I*:2707–2713 (1973).

Cai et al., "Synthesis, Structure and Properties of New Boron–Containing Heterocycles," *13th Intl. Congress of Heterocyclic Chemistry*, Corvallis, OR (Aug., 1991).

Cheeseman, G. W. H., "Quinoxalines and Related Compounds. Part VI. Substitution of 2,3–Dihydroxyquinoxaline and its 1,4–Dimethyl Derivative," *J. Chem. Soc.* 84:1170–1176 (1962).

(List continued on next page.)

*Primary Examiner*—Emily Bernhardt
*Attorney, Agent, or Firm*— Sterne, Kessler, Goldstein & Fox, P.L.L.C.

[57] ABSTRACT

Methods of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the hyperactivity of the excitatory amino acids, as well as treating anxiety, chronic pain, convulsions and inducing anesthesia are disclosed by administering to an animal in need of such treatment a compound which has high binding to the glycine receptor.

6 Claims, No Drawings

OTHER PUBLICATIONS

Clifford et al., "Herbicidal and Pesticidal Properties of Some 1,5–Benzodiazepines, 1,3,5–Benzotriazepines and 3,1, 5–Benzothiadiazepines," *Pestic. Sci.* 7:453–458 (1976).

Couquelet et al., "Sur le pouvoir angioprotecteur de quelques sels d'acide chromone–carboxylique–2: relation avec le pKa des amines," *Société De Biologie De Clermont–Ferrand* pp. 329–331 (1970).

Dahn, H. and Danzel, A., "Über die 1,2–Verschiebung der Säuremidgruppe bei der Benzilsäureumlagerung von Chinisatin," *Helvetica Chimica Acta* 50(7):1911–1917.

Di Braccio et al., "1,5–Benzodiazepines X. Dialkylamino substituted 1,5–benzodiazepine and [1,2,4] triazolo [4,3–a] [1,5] benzodiazepine derivatives with inhibitory activity on PAF–induced platelet aggregation," *Il Farmaco* 47(1):77–90 (1992).

Ehrhardt et al., "Amide und Thioamide der Quadratsäure: Synthese und Reaktionen," *Chem. Ber.* 110:2506–2523 (1977).

Eicher, T. and Kruse, A., "Synthese und Eigenschaften von 2–Amino–3–oxo–3H–azepinen," *Synthesis* pp. 612–619 (Jun./Jul. 1985).

El–Enany et al., "Synthesis of Certain Benzo—and Pyridodiazepines Likely to Possess Tranquilizing Effect," *Pharmazie* 32:79–81 (1977).

Faber et al., "Non–Steroidal Antiinflammatory Agents. 1. Synthesis of 4–Hydroxy–2–oxo–1,2–dihydroquinolin–3–yl Alkanoic Acids by the Wittig Reaction of Quinisatines," *J. Heterocyclic Chem.* 21:1177–1181 (1984).

Fletcher and Lodge, "Glycine reverses antagonism of N–methyl–D–aspartate (NMDA) by 1–hydroxy–3–aminopyrrolidone–2 (HA–966) but not by D–2–amino–5–phophonovalerate (D–AP5) on rat cortical slices," *Eur. J. Pharmacol.* 151:161–162 (1988).

Garcia et al., "Acyl Indoles. III(1). The Synthesis of [1,4] Diazepino[6,5–b]indoles," *J. Heterocyclic Chem.* 10:51–53 (1973).

Gray et al., "Novel Indole–2–carboxylates as Ligands for the Strychnine–Insensitive N–Methyl–D–aspartate–Linked Glycine Receptor," *J. Med. Chem.* 34:1283–1292 (1991).

Greibrokk, T. and Undheim, K., "N–Quaternary Compounds. Part XXII. Quinoline Derivatives," *Acta Chemica Scandinavica* 25(8):2935–2942 (1971).

Harsányi et al., "Synthese und Oxidation von 2–(Hydroxyimino)–1,2–dihydro–chinoxalin," *Liebigs Ann. Chem.* pp. 190–194 (1973).

Hughes, C. G. and Rees, A. H., "2,3–Dihydro–2, 3–dioxo–1–benzazepine," *Chemistry and Industry* p. 1439 (Dec. 11, 1971).

Iijima, C., "Quinoxalines. XXV. Synthesis and Chemical Properties of 2–Nitroquinoxaline," *Yakugaku Zasshi* 109(1):18–25 (1989).

Johnsen, B. A. and Undheim, K., "N–Quaternary Compounds. Part LVI. 3–Hydroxyquinoline–2(1H)–thiones and Their N–Vinylation," *Acta Chemica Scandinavica B* 38(2):109–112 (1984).

Johnson, J. W. and Ascher, P., "Glycine potentiates the NMDA response in cultured mouse brain neurons," *Nature* 325:529–531 (1987).

Jones, G., "Some Basic and Acidic Derivatives of 2,5–Dihydro–1H–1–Benzazepine as Potential Therapeutic Agents," *J. Chem. Soc.* (C):1808–1813 (1967).

Kappe, Th. and Ziegler, E., "Synthesen von Heterocyclen, 53.Mitt.: Zur Chemie der Chlornitromalonyl–Verbindungen," *Mh. Chem.* 95:415–421 (1964).

Keana, J. F. W. and Cai, S. X., "New Reagents for Photoaffinity Labeling: Synthesis and Photolysis of Functionalized Perfluorophenyl Azides," *J. Org. Chem.* 55:3640–3647 (1990).

Kemp, J. A. and Leeson, P. D., "The glycine site of the NMDA receptor – five years on," *TiPS* 14:20–25 (1993).

Kemp et al., "7–Chlorokynurenic acid is a selective antagonist at the glycine modulatory site of the N–methyl–D–aspartate receptor complex," *PNAS USA* 85:6547–6550 (1988).

Kim, D. H., "Improved Syntheses of 1,4–Benzodiazepine–2, 5–diones," *J. Heterocyclic Chem.* 12:1323–1324 (1975).

Kulagowski et al., "3'–(Arylmethyl)– and 3'–(Aryloxy)–3–phenyl–4–hydroxyquinolin–2(1H)–ones: Orally Active Antagonists of the Glycine Site on the NMDA Receptor," *J. Med. Chem.* 37(10):1402–1405 (1994).

Leeson, P. D., "Glycine–Site N–Methyl–D–Aspartate Receptor Antagonists," *Drug Design for Neuroscience*, Chap. 13, A. P. Kozikowski, ed., Raven Press, Ltd., NY, pp. 339–381 (1993).

Leeson, P. D. and Iversen, L. L., "The Glycine Site on the NMDA Receptor: Structure–Activity Relationships and Therapeutic Potential," *J. Med. Chem.* 37(24):4053–4067 (1994).

Leeson et al., "Amino Acid Bioisosteres: Design of 2–Quinolone Derivatives as Glycine–Site N–Methyl–D–Aspartate Receptor Antagonists," *Bioorganic and Medicinal Chem. Lett.* 3(2):299–304 (1993).

Leeson et al., "Kynurenic Acid Derivatives. Structure–Activity Relationships for Excitatory Amino Acid Antagonism and Identification of Potent and Selective Antagonists at the Glycine Site on the N–Methyl–D–aspartate Receptor," *J. Med. Chem.* 34:1243–1252 (1991).

Loev et al., "[1,4]Benzoxazine–2,3–diones as Antiallergic Agents," *J. Med. Chem.* 28:24–27 (1985).

McKillop et al., "Heterocyclic Synthesis Using Ethyl Carboethoxyformimidate," *Tetrahedron Lett.* 23(33):3357–3360 (1982).

McQuaid et al., "Synthesis and Excitatory Amino Acid Pharmacology of a Series of Heterocyclic–Fused Quinoxalinones and Quinazolinones," *J. Med. Chem.* 35:3319–3324 (1992).

Minami et al., "Synthesis of a 3,1–Benzoxazin–4–one, 2,4(1H,3H)–Quinolinedones, and 2,4(1H,3H)–Quinazolinediones from the Reaction of Phosphoryl–Stabilized Anions Containing no α–Hydrogen Atoms with Isatoic Anhydride," *Synthesis* pp. 231–233 (Mar. 1982).

Mitchell et al., "N–Bromosuccinimide–Dimethylformamide: A Mild, Selective Nuclear Monobromination Reagent for Reactive Aromatic Compounds," *J. Org. Chem.* 44(25):4733–4735 (1979).

Mohiuddin et al., "A Versatile Synthesis of 3H–1 (H), 4(H)–Benzodiazepin–2,5–diones," *Indian J. Chem.* 24B:905–907 (1985).

Mordecai et al., "Comparative Effect of Transient Global Ischemia on Extracellular Levels of Glutamate, Glycine, and Y–Aminobutyric Acid in Vulnerable and Nonvulnerable Brain Regions in the Rat," *J. Neurochem.* 57(2):470–478 (1991).

Movrin, M. and Mladar, M. J., "Biologisch aktive N–Mannich–Basen von 2,3–Dioxo–1,4–benzoxazin," *Pharmazie* 38(12):883–885 (1983).

Movrin et al., "1,3–Benzoxazin–2,4–dione and 1,4–benzoxazin–2,3–dione derivatives, as biologically active compounds," *Acta Pharm. Jugosl.* 35:193–202 (1985).

Neville et al., "An FT–Raman and IR Study of Oxazepam, Temazepam, Lorazepam, and Lormetazepam," *Can. J. Appl. Spectroscopy* 37(1):18–29 (1992).

Nishi et al., "Studies on 2–Oxoquinoline Derivatives as Blood Platelet Aggregation Inhibitors. III. N–Cyclohexyl–N–(2–hydroxyethyl)–4–(1, 2–dihydro–2–oxo–6–quinolyloxy)–butyramide and Related Compounds," *Chem. Pharm. Bull.* 31(3):852–860 (1983).

Osman, A. N. and El–Enani, M. M., "Nucleophilic Cleavage of 3,5–Dioxo–2,3,4,5–Tetrahydro–1,4–Benzoxazepine," *Egypt. J. Pharm. Sci.* 22(1–4):1–7 (1981).

Peet et al., "The N–Methyl–D–Aspartate Receptor and Burst Firing of CA1 Hippocampal Pyramidal Neurons," *Neuroscience* 22(2):563–571 (1987).

Reissenweber, G. and Mangold, D., "Oxidation of Isatins to Isatoic Anhydrides and 2,3–Dioxo–1,4–benzoxazines," *Angew. Chem. Int. Ed. Engl.* 19(3):222–223 (1980).

Rickards, R. W. and Smith, R. M., "The Synthesis of 1H,2H,5H–Azepine–2,5–Diones by Schmidt Rearrangement of Quinones," *Tetrahedron Lett.* 22:2361–2365 (1966).

Rowley et al., "3–Acyl–4–hydroxyquinolin–2(1H)–ones. Systemically Active Anticonvulsants Acting by Antagonism at the Glycine Site of the N–Methyl–D–Aspartate Receptor Complex," *J. Med. Chem.* 36:3386–3396 (1993).

Schmidt, S. P. and Schuster, G. B., "Photolysis of o–Phenylene Oxalate. A High–Yield Photodecarbonylation Reaction," *J. Org. Chem.* 43(9):1823–1824 (1978).

Skujins, S. and Webb, G. A., "Synthesis of Cyclobuta[b] quinoxalines," *Chemical Comm.* pp. 598–599 (1968).

Soliman et al., "Medium and Temperature Effects on the Ionisation Process of Some 4–(Substituted)–3–Hydroxy–2–Quinolone Compounds," *Annali di Chimica* 78:287–296 (1988).

Soloway, A. H., "Synthesis of Aromatic Diboronic Acids," *J. Amer. Chem. Soc.* 82:2442–2444 (1960).

Stefănescu, P. N., "Noi Compusi De Isatină," *Rev. Chim. (Bucharest)* 20:353–355 (1969).

Stempel et al., "Quinazolines and 1,4–Benzodiazepines. XLI. 1,3–Dihydro–2H–1,4–benzodiazepin–2–one 4–Oxide Previously Described as 1,3–Dihydro–2H–4,1, 5–benzoxadiazocin–2–one," *J. Org. Chem.* 33(7):2963–2966 (1968).

Sterk, H. and Ziegler, E., "Infrarotspektroskopische Untersuchungen am 4–Hydroxy–carbostyril und seinen Derivaten," *Mh. Chem.* 98:100–104 (1967).

Šunjić et al., "Chiral 1,4–Benzodiazepines. X. Further Investigations of Configurational Stability of the Chiral Centre C(3)," *Croatica Chemica Acta* 49(3):505–515 (1977).

Takahashi et al., "Synthesis of 1,2,4–Oxadiazoles, Quinazolines and 1,4–Benzodiazepines from Isatoic Anhydride," *Nippon Kagaku Kaishi* 7:1259–1263 (1972).

Taniguchi, M. and Satomura, Y., "Structure and Physiological Activity of Carbostyril Compounds," *Agr. Biol. Chem.* 36(12):2169–2175 (1972).

Tricklebank et al., "The behavioural effects of MK–801: a comparison with antagonists acting non–competitively and competitively at the NMDA receptor," *Eur. J. Pharmacol.* 167:127–135 (1989).

Tricklebank et al., "A role for receptors of N–methyl–D–aspartic acid in the discriminative stimulus properties of phencyclidine," *Eur. J. Pharmacol.* 141:497–501 (1987).

Varma, R. S. and Singh, A. P., "A novel pH dependent separation of isatins from their isomeric mixtures," *Indian J. Chem.* 29B:578–581 (1990).

Walker, G. N., "Synthesis of 2–Benzazepine–1,3–diones and Corresponding 4,5–Dihydro Compounds," *J. Org. Chem.* 37(24):3955–3958 (1972).

Ziegler, E. and Hanus, H. D., "Syntheses of heterocycles. LXV. Reactions with salicylic acid chloride," *Chem. Abstracts* 63:5635–5637 (1965).

GLYCINE RECEPTOR ANTAGONIST PHARMACOPHORE

The present invention was made under NIDA Grant No. DA 6726 awarded by the National Institutes of Health. Therefore, the U.S. Government has certain rights in the invention.

FIELD OF THE INVENTION

The present invention is in the field of medicinal chemistry. In particular, the present invention relates to glycine receptor antagonists and pharmaceutically acceptable salts thereof and their use to treat or prevent neuronal degeneration associated with ischemia, pathophysiologic conditions associated with neuronal degeneration, convulsions, anxiety, chronic pain and to induce anesthesia.

BACKGROUND OF THE INVENTION

Glutamate is thought to be the major excitatory neurotransmitter in the brain. There are three major subtypes of glutamate receptors in the CNS. These are commonly referred to as kainate, AMPA and N-methyl-D-aspartate (NMDA) receptors (Watkins and Olverman, *Trends in Neurosci.* 7:265–272 (1987)). NMDA receptors are found in the membranes of virtually every neuron in the brain. NMDA receptors are ligand-gated cation channels that allow $Na^+$, $K^+$ and $Ca^{++}$ to permeate when they are activated by glutamate or aspartate (non-selective, endogenous agonists) or by NMDA (a selective, synthetic agonist) (Wong and Kemp, *Ann. Rev. Pharmacol. Toxicol.* 31:401–425 (1991)).

Glutamate alone cannot activate the NMDA receptor. In order to become activated by glutamate, the NMDA receptor channel must first bind glycine at a specific, high affinity glycine binding site which is separate from the glutamate/NMDA binding site on the receptor protein (Johnson and Ascher, *Nature* 325:329–331 (1987)). Glycine is therefore an obligatory co-agonist at the NMDA receptor/channel complex (Kemp, J. A., et al., *Proc. Natl. Acad. Sci. USA* 85:6547–6550 (1988)).

Besides the binding sites for glutamate/NMDA and glycine, the NMDA receptor carries a number of other functionally important binding sites. These include binding sites for $Mg^{++}$, $Zn^{++}$, polyamines, arachidonic acid and phencyclidine (PCP) (Reynolds and Miller, *Adv. in Pharmacol.* 21:101–126 (1990); Miller, B., et al., *Nature* 355:722–725 (1992)). The PCP binding site—now commonly referred to as the PCP receptor—is located inside the pore of the ionophore of the NMDA receptor/channel complex (Wong, E. H. F., et al., *Proc. Natl. Acad. Sci. USA* 83:7104–7108 (1986); Huettner and Bean, *Proc. Natl. Acad. Sci. USA* 85:1307–1311 (1988); MacDonald, J. F., et al., *Neurophysiol.* 58:251–266 (1987)). In order for PCP to gain access to the PCP receptor, the channel must first be opened by glutamate and glycine. In the absence of glutamate and glycine, PCP cannot bind to the PCP receptor although some studies have suggested that a small amount of PCP binding can occur even in the absence of glutamate and glycine (Sircar and Zukin, *Brain Res.* 556:280–284 (1991)). Once PCP binds to the PCP receptor, it blocks ion flux through the open channel. Therefore, PCP is an open channel blocker and a non-competitive glutamate antagonist at the NMDA receptor/channel complex.

One of the most potent and selective drugs that bind to the PCP receptor is the anticonvulsant drug MK-801. This drug has a $K_d$ of approximately 3 nM at the PCP receptor (Wong, E. H. F., et al., *Proc. Natl. Acad. Sci. USA* 83:7104–7108 (1986)).

Both PCP and MK-801 as well as other PCP receptor ligands [e.g., dextromethorphan, ketamine and N,N,N'-trisubstituted guanidines] have neuroprotective efficacy both in vitro and in vivo (Gill, R., et al., *J. Neurosci.* 7:3343–3349 (1987); Keana, J. F. W., et al., *Proc. Natl. Acad. Sci. USA* 86:5631–5635 (1989); Steinberg, G. K., et al., *Neuroscience Lett.* 89:193–197 1988); Church, J., et al., In: *Sigma and Phencyclidine-Like Compounds as Molecular Probes in Biology*, Domino and Kamenka, eds., Ann Arbor: NPP Books, pp. 747–756 (1988)). The well-characterized neuroprotective efficacy of these drugs is largely due to their capacity to block excessive $Ca^{++}$ influx into neurons through NMDA receptor channels which become over activated by excessive glutamate release in conditions of brain ischemia (e.g., in stroke, cardiac arrest ischemia etc.) (Collins, R. C., *Metabol. Br. Dis.* 1:231–240 (1986); Collins, R. C., et al., *Annals Int. Med.* 110:992–1000 (1989)).

However, the therapeutic potential of these PCP receptor drugs as ischemia rescue agents in stroke has been severely hampered by the fact that these drugs have strong PCP-like behavioral side effects (psychotomimetic behavioral effects) which appear to be due to the interaction of these drugs with the PCP receptor (Tricklebank, M. D., et al., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988)). These PCP-like behavioral side effects appear to have caused the withdrawal of MK801 from clinical development as an ischemia rescue agent. Furthermore, these PCP receptor ligands appear to have considerable abuse potential as demonstrated by the abuse liability of PCP itself.

The PCP-like behavioral effects of the PCP receptor ligands can be demonstrated in animal models: PCP and related PCP receptor ligands cause a behavioral excitation (hyperlocomotion) in rodents (Tricklebank, M. D., et al., *Eur. J. Pharmacol.* 167:127–135 (1989))and a characteristic katalepsy in pigeons (Koek, W., et al., *J. Pharmacol. Exp. Ther.* 245:969 (1989); Willets and Balster, *Neuropharmacology* 27:1249 (1988)); in drug discrimination paradigms, there is a strong correlation between the PCP receptor affinity of these drugs and their potency to induce a PCP-appropriate response behavior (Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)).

Drugs acting as competitive antagonists at the glutamate binding site of the NMDA receptor such as CGS 19755 and LY274614 also have neuroprotective efficacy because these drugs-like the PCP receptor ligands—can prevent excessive $Ca^{++}$ flux through NMDA receptor/channels in ischemia (Boast, C. A., et al., *Brain Res.* 442:345–348 (1988); Schoepp, D. D., et al., *J. Neural. Trans.* 85:131–143 (1991)). However, competitive NMDA receptor antagonists also have PCP-like behavioral side-effects in animal models (behavioral excitation, activity in PCP drug discrimination tests) although not as potently as MK-801 and PCP (Tricklebank, M. D., et al., *Eur. J. Pharmacol.* 167:127–135 (1989)).

An alternate way of inhibiting NMDA receptor channel activation is by using antagonists at the glycine binding site of the NMDA receptor. Since glycine must bind to the glycine site in order for glutamate to effect channel opening (Johnson and Ascher, *Nature* 325:329–331 (1987); Kemp, J.A., et al., *Proc. Natl. Acad. Sci. USA* 85:6547–6550

(1988)), a glycine antagonist can completely prevent ion flux through the NMDA receptor channel—even in the presence of a large amount of glutamate.

Recent in vivo microdialysis studies have demonstrated that in the rat focal ischemia model, there is a large increase in glutamate release in the ischemic brain region with no significant increase in glycine release (Globus, M. Y. T., et al., *J. Neurochem.* 57:470–478 (1991)). Thus, theoretically, glycine antagonists should be very powerful neuroprotective agents, because they can prevent the opening of NMDA channels by glutamate non-competitively and therefore—unlike competitive NMDA antagonists—do not have to overcome the large concentrations of endogenous glutamate that are released in the ischemic brain region.

Furthermore, because glycine antagonists act at neither the glutamate/NMDA nor the PCP binding sites to prevent NMDA channel opening, these drugs might not cause the PCP-like behavioral side effect seen with both PCP receptor ligands and competitive NMDA receptor antagonists (Tricklebank, M. D., et al., *Eur. J. Pharmacol.* 167:127–135 (1989); Koek, W., et al., *J. Pharmacol. Exp. Ther.* 245:969 (1989); Willets and Balster, *Neuropharmacology* 27:1249 (1988); Tricklebank, M. D., et al., *Eur. J. Pharmacol.* 167:127–135 (1989); Zukin, S. R., et al., *Brain Res.* 294:174 (1984); Brady, K. T., et al., *Science* 215:178 (1982); Tricklebank, M. D., et al., *Eur. J. Pharmacol.* 141:497 (1987)). That glycine antagonists may indeed be devoid of PCP-like behavioral side effects has been suggested by recent studies in which available glycine antagonists were injected directly into the brains of rodents without resulting in PCP-like behaviors (Tricklebank, M. D., et al., *Eur. J. Pharmacol.* 167:127–135 (1989)).

There have been two major problems which have prevented the development of glycine antagonists as clinically useful neuroprotective agents:

A. Most available glycine antagonists with relatively high receptor binding affinity in vitro such as 7-Cl-kynurenic acid (Kemp, J. A., et al., *Proc. Natl. Acad. Sci. USA* 85:6547–6550 (1988)), 5,7-dichlorokynurenic acid (McNamara, D., et al., *Neuroscience Lett.* 120:17–20 (1990)) and indole-2-carboxylic acid (Gray, N. M., et al., *J. Med. Chem.* 34:1283–1292 (1991)) cannot penetrate the blood/brain barrier and therefore have no utility as therapeutic agents;

B. The only widely available glycine antagonist that sufficiently penetrates the blood/brain barrier-the drug HA-966 (Fletcher and Lodge, *Eur. J. Pharmacol.* 151:161–162 (1988))—is a partial agonist with micromolar affinity for the glycine binding site. A neuroprotective efficacy for HA-966 in vivo has not been demonstrated nor has it been demonstrated for the other available glycine antagonists because they lack bioavailability in vivo.

However, one recent success in identifying orally active glycine receptor antagonists was reported by Kulagowski et al., *J. Med. Chem.* 37:1402–1405 (1994), who disclose that 3-substituted 4-hydroxyquinoline-2(1H)-ones are selective glycine antagonists possessing potent in vivo activity.

A need continues to exist for potent and selective glycine/NMDA antagonists which can penetrate the blood/brain barrier and which:

lack the PCP-like behavioral side effects common to the PCP-like NMDA channel blockers such as MK801 or to the competitive NMDA receptor antagonists such as CGS19755;

show potent anti-ischemic efficacy because of the non-competitive nature of their glutamate antagonism at the NMDA receptor;

have utility as novel anticonvulsants with fewer side-effects than the PCP-like NMDA channel blockers or the competitive NMDA antagonists;

help in defining the functional significance of the glycine binding site of the NMDA receptor in vivo.

SUMMARY OF THE INVENTION

The invention relates to glycine receptor antagonists defined by the following pharmacophore (I)

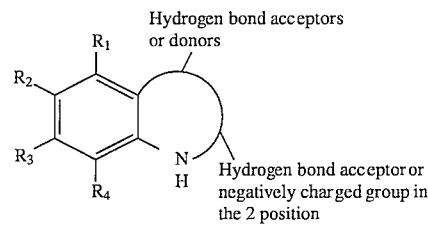

$R_2$ and $R_3$ may form a cyclic system as follows:

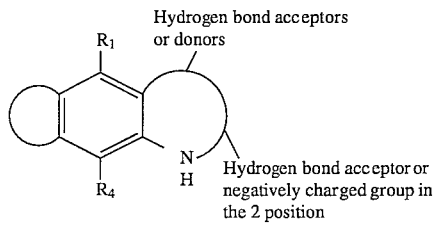

The heterocyclic portion of the molecule also may be a bicyclic system

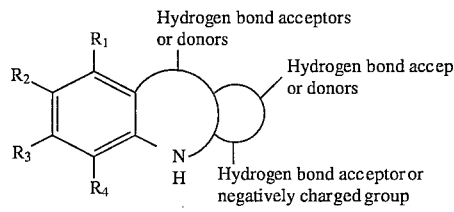

wherein
$R_1$-$R_3$ may be nitro, amino, halo, haloalkyl, cyano, alkyl, alkenyl, alkynyl, azido, acylamino, sulfonyl, aryl, alkoxy, carbonyl, alkoxycarbonyl or alkylcarbonyl; and $R_4$ may be hydrogen or fluoro.

In particular, the glycine receptor antagonists of the present invention include:

(1) compounds wherein the heterocyclic ring has 5, 6 or 7 members;

(2) compounds with multi-substitution on the benzene ring, e.g., di, tri- or tetra-substitution. Preferred compounds are substituted with electron withdrawing groups such as halo, nitro, $CF_3$ and/or with amino or methyl groups;

(3) compounds with an unsubstituted nitrogen in the 1-position of the heterocyclic ring;

(4) compounds having a hydrogen bond acceptor such as carbonyl, nitro, boronic acid (—$B(OH)_2$), carboxyl, $N(CN)_2$, $C(CN)_3$, NHCN, CH=$C(CN)_2$ or a negatively charged group at the 2-position of the heterocyclic ring, however, non-charged groups such as carbonyl, nitro and boronic acid are preferred;

(5) compounds with one or more hydrogen bond acceptors such as hydroxy, amido, oxime and amino or hydrogen bond donors such as hydroxy, oxime, amino and amido on the 3, 4, and/or 5 positions of the heterocyclic ring;

(6) compounds having one or more heteroatoms, e.g., nitrogen or nitrogen N-oxides, in place of the carbon atoms of the benzene ring.

It has been discovered that the structure of the heterocyclic ring determines whether the compounds is an antagonist for the glycine binding site. In addition, it has also been discovered that multi-substitution on the benzene ring enhances the binding affinity to the glycine binding site.

The present pharmacophore model is an improvement over the model proposed by Lesson et al., *J. Med. Chem.* 34:1243–1252 (1991), as Lesson et al. did not recognize that:

(1) the heterocyclic ring may be a 5, 6 or 7-membered ring;

(2) multi-substitution on the benzene ring enhances the binding affinity to the glycine binding site;

(3) hydrogen bond acceptors such as carbonyl, nitro and boronic acid in the 2-position are important for high affinity to the glycine binding site;

(4) non-charged groups such as carbonyl, nitro, oxime, halo, haloalkyl, O-alkyloxime, alkoxyamine or a well-known bioisostere of a carboxyl group (5-tetrazolyl or 4- or 5-substituted 3-hydroxyisoxazoles), enhance lipophilicity and, thus, the ability to cross the blood-brain barrier;

(5) mono- and multi-hydrogen bond acceptors such as carbonyl, nitro, oxime and hydroxy and/or hydrogen bond donors such as oxime, hydroxy and amino in the 3, 4 and 5-positions of the heterocyclic ring increase affinity to the glycine binding site;

(6) that the definition of the substitutions on the heterocyclic portion of the molecule and the benzene portion of the molecule are important for high binding to the glycine binding site; and (7) that one or more heteroatoms may be substituted for the carbon atoms of the benzene ring.

The invention relates to a method of treating or preventing neuronal loss associated with stroke, ischemia, CNS trauma, hypoglycemia and surgery, as well as treating neurodegenerative diseases including Alzheimer's disease, amyotrophic lateral sclerosis, Huntington's disease and Down's syndrome, treating or preventing the adverse consequences of the overstimulation of the excitatory amino acids, as well as treating anxiety, convulsions, chronic pain and inducing anesthesia, comprising administering to an animal in need of such treatment a compound defined by the pharmacophore of Formula (I), or a pharmaceutically acceptable salt thereof.

Examples of compounds defined by the pharmacophore having Formula (I) include, but are not limited to, compounds selected from the group consisting of:

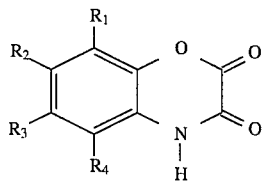

IV

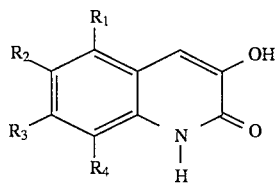

V

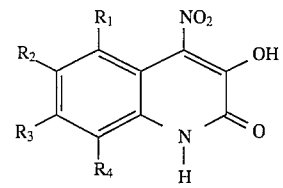

VI

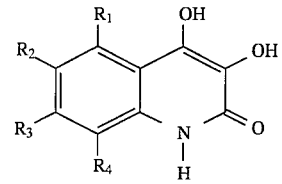

VII

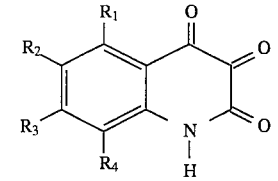

VIII

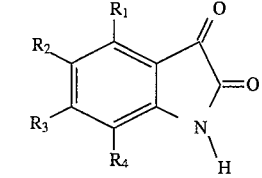

IX

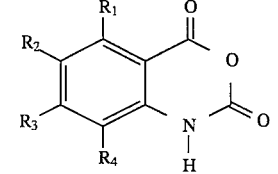

X

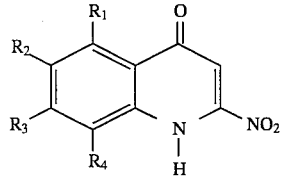

XI

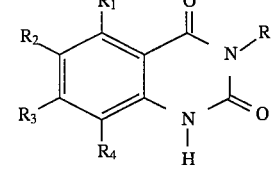

XII

R = H, OH, Ph, CH$_2$Ph, OCOR

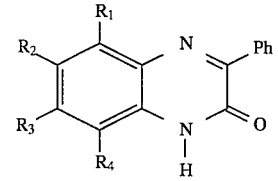

XIII

-continued
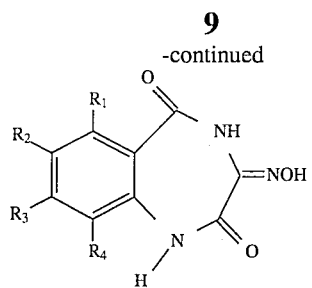 XXIX
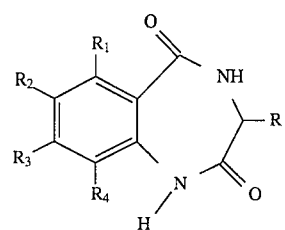 XXX
R = Ph, CH₂Ph
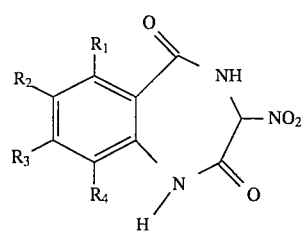 XXXI
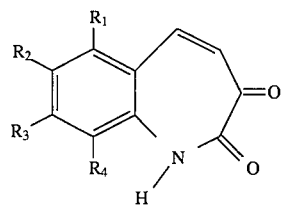 XXXII
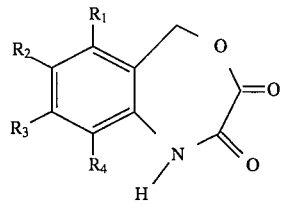 XXXIII
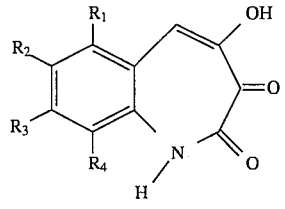 XXXIV
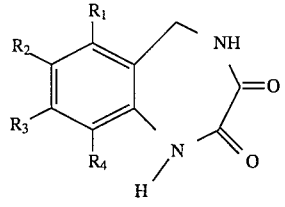 XXXV
-continued
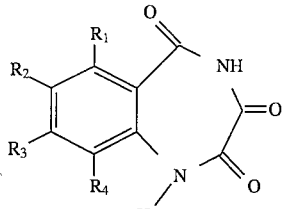 XXXVI
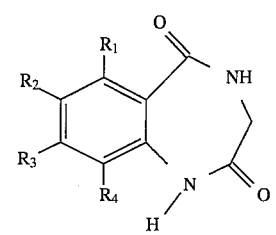 XXXVII
XXXVIII
XXXIX
XL
XLI
XLII
R = alkyl (methyl)

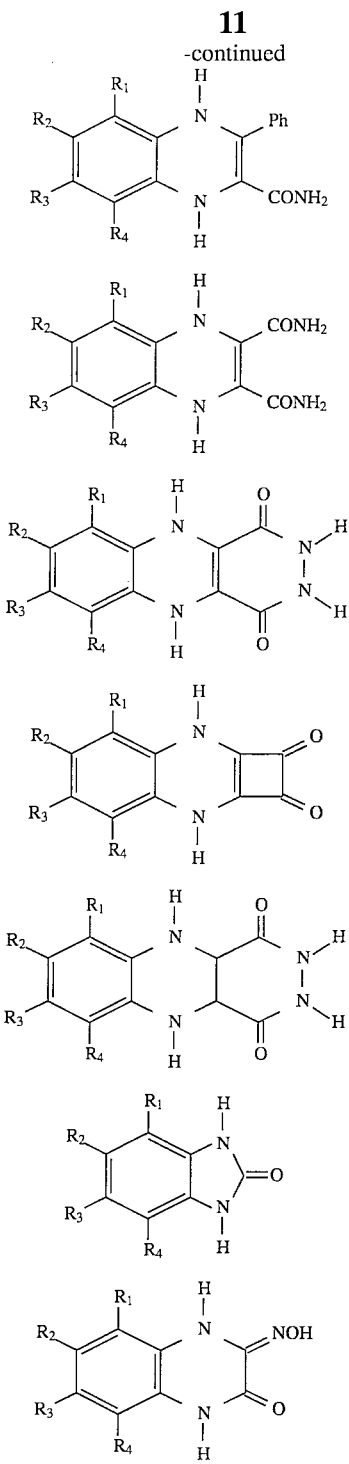

wherein $R_1$ to $R_4$ may be independently hydrogen, alkyl, hydrogen, nitro, amino, halo, haloalkyl, cyano, alkenyl, alkynyl, arylalkyl, arylalkenyl, arylalkynyl, aryloxyalkyl, azido, acylamino, sulfonyl, aryl, alkoxy, carbonyl, alkoxycarbonyl or alkylcarbonyl;

with the proviso that with respect to the compounds having Formulas IV, V, VI, VII, VIII, IX, X, XI, XII, XIII, XIV, XV, XVI, XVII, XVIII, XIX, XX, XXI, XXII, XXIII, XXIV, XXV, XXVI, XXVIII, XXIX, XXX, XXXI, XXXII, XXXIII, XXXIV, XXXV, XXXVI, XXXVII, and XXXVIII, $R_4$ is hydrogen or fluoro.

DESCRIPTION OF THE PREFERRED EMBODIMENTS

The present invention relates to compounds defined by the pharmacophore having Formula (I), e.g., compounds having the Formulae IV–XLIX, as well as the tautomeric isomers thereof, which are highly selective, competitive antagonists of the glycine binding site of the NMDA receptor and of the excitatory amino acids.

Preferred compounds within the scope of the present invention are wherein $R_1$, $R_2$ and $R_3$ are other than hydrogen, e.g., $R_1$ is nitro, amino, chloro, alkyl or bromo; $R_2$ is hydrogen, chloro, bromo, alkyl or trifluoromethyl; $R_3$ is nitro, chloro, bromo, alkyl or trifluoromethyl; and $R_4$ is hydrogen or fluoro.

Other preferred compounds are wherein $R_2$ is an arylalkyl, arylalkenyl, arylalkynyl or aryloxyalkyl group. Such compounds are expected to show increased lipophilicity and, therefore, ability to cross the blood-brain barrier. Such compounds are also expected to bind favorably to a hypothetical hydrophobic binding pocket which might be present at a position 10 o'clock to the benzene ring (or heteroaryl ring). Alternatively, a long chain alkanoylamino group (an acylamino group) may be present at $R_1$ to interact with this binding pocket.

Typical $C_{6-14}$ aryl groups include phenyl, naphthyl, phenanthryl, anthracyl, indenyl, azulenyl, biphenyl, biphenylenyl and fluorenyl groups.

Typical amino groups include $NH_2$, $NHR_5$ and $NR_5R_6$, wherein $R_5$ and $R_6$ are $C_{1-4}$ alkyl groups.

Typical halo groups include fluorine, chlorine, bromine and iodine.

Typical $C_{1-4}$ alkyl groups include methyl, ethyl, propyl, isopropyl, butyl, sec.-butyl, and tert.-butyl groups.

Typical $C_{2-4}$ alkenyl groups include vinyl, allyl, 1-butenyl, 2-butenyl, 3-butenyl, and isobutenyl groups.

Typical $C_{2-4}$ alkynyl groups include propargyl, 1-propynyl, 2-propynyl, 1-butynyl, 2-butynyl and 3-butynyl groups.

Typical haloalkyl groups include $C_{1-4}$ alkyl groups substituted by one or more fluorine, chlorine, bromine or iodine atoms, e.g., fluoromethyl, difluoromethyl, trifluoromethyl, pentafluoroethyl, 1,1-difluoroethyl and trichloromethyl groups.

Typical alkoxy groups include oxygen substituted by one of the $C_{1-4}$ alkyl groups mentioned above.

Typical $C_{2-4}$ acylamino (alkanoylamino) groups include acetamido, propanamido, and butanamido.

With respect to Formula IV, particularly preferred compounds which may be used in the practice of the present invention include, but are not limited to 4,1-benzoxazine-2,3-dione, 6,7-dichloro-5-nitro-4,1-benzoxazine-2,3-dione, 6,7-dibromo-5-nitro-4,1-benzoxazine-2,3-dione, 6,7-difluoro-5-nitro-4,1-benzoxazine-2,3-dione, 6,7-methyl-5-nitro-4, 1-benzoxazine-2,3-dione, 5,7-bis(trifluoromethyl)-4,1-benzoxazine-2,3-dione, 5,7-dimethyl-4,1 -benzoxazine-2,3-dione, 5,7-dichloro-4,1-benzoxazine-2,3-dione, 5,7-difluoro-4,1-benzoxazine-2,3-dione, and 5,6,7-trichloro-4,1-benzoxazine-2,3-dione.

With respect to Formula V, particularly preferred compounds which may be used in the practice of the present invention include, but are not limited to 2,3-dihydroxyquinoline, 6,7-dichloro-5-nitro-2,3-dihydroxyquinoline, 6,7-dibromo-5-nitro-2,3-dihydroxyquinoline, 6,7-difluoro-5-nitro-2,3-dihydroxyquinoline, 6,7-dimethyl-5-nitro-2,3-dihydroxyquinoline, 5,7-bis(trifluoromethyl)-2,3-dihydroxquinoline, 5,7-dimethyl-2,3-dihydroxyquinoline, 5,7-dichloro-2,3-dihydroxyquinoline, 5,7-difluoro-2,3-dihydroxyquinoline, and 5,6,7-trichloro-2,3-dihydroxyquinoline.

With respect to Formula VI, particularly preferred compounds which may be used in the practice of the present invention include, but are not limited to 3-hydroxy-4-nitro-2-quinolone, 6,7-dichloro-3-hydroxy-4,5-dinitro-2-quinolone, 6,7-dibromo-3-hydroxy-4,5-dinitro-2-quinolone, 6,7-difluoro-3-hydroxy-4,5-dinitro-2-quinolone, 6,7-dimethyl-3-hydroxy-4,5-dinitro-2-quinolone, 5,7-bis(trifluoromethyl)-3-hydroxy-4-nitro-2-quinolone, 5,7-dimethyl-3-hydroxy-4-nitro-2-quinolone, 5,7-dichloro-3-hydroxy-4-nitro-2-quinolone, 5,7-difluoro-3-hydroxy-4-nitro-2-quinolone, and 5,6,7-trichloro-3-hydroxy-4-nitro-2-quinolone.

With respect to Formula VII, particularly preferred compounds which may be used in the practice of the present invention include, but are not limited to 2,3,4-trihydroxyquinoline, 6,7-dichloro-5-nitro-2,3,4-trihydroxyquinoline, 6,7-dibromo-5-nitro-2,3,4-trihydroxyquinoline, 6,7-difluoro-5-nitro-2,3,4-trihydroxyquinoline, 6,7-dimethyl-5-nitro-2,3,4-trihydroxyquinoline, 5,7-bis(trifluoromethyl)-2,3,4-trihydroxyquinoline, 5,7-dimethyl-2,3,4-trihydroxyquinoline, 5,7-dichloro-2,3,4-trihydroxyquinoline, 5,7-difluoro-2,3,4-trihydroxyquinoline, and 5,6,7-trichloro-2,3,4-trihydroxyquinoline.

With respect to Formula VIII, particularly preferred compounds which may be used in the practice of the present invention include, but are not limited to quinoline-2,3,4-trione, 6,7-dichloro-5-nitroquinoline-2,3,4-trione, 6,7-dibromo-5-nitro-quinoline-2,3,4-trione, 6,7-difluoro-5-nitroquinoline-2,3,4-trione, 6,7-dimethyl-5-nitro-quinoline-2,3,4-trione, 5,7-bis(trifluoromethyl)quinoline-2,3,4-trione, 5,7-dimethyl-quinoline-2,3,4-trione, 5,7-dichloro-quinoline-2,3,4-trione, 5,7-difluoro-quinoline-2,3,4-trione, and 5,6,7-trichloro-quinoline-2,3,4-trione.

With respect to Formula IX, particularly preferred compounds which may be used in the practice of the present invention include, but are not limited to isatin, 5,6-dichloro-4-nitroisatin, 5,6-dibromo-4-nitroisatin, 5,6-difluoro-4-nitroisatin, 5,6-dimethyl-4-nitroisatin, 4,6-bis(trifluoromethyl)isatin, 4,6-dimethylisatin, 4,6-dichloroisatin, 4,6-difluoroisatin, and 4,5,6-trichloroisatin.

With respect to Formula X, particularly preferred compounds which may be used in the practice of the present invention include, but are not limited to isatoic anhydride, 6,7-dichloro-5-nitroisatoic anhydride, 6,7-dibromo-5-nitroisatoic anhydride, 6,7-difluoro-5-nitroisatoic anhydride, 6,7-dimethyl-5-nitroisatoic anhydride, 5,7-bis(trifluoromethyl)isatoic anhydride, 5,7-dimethylisatoic anhydride, 5,7-dichloroisatoic anhydride, 5,7-difluoroisatoic anhydride, and 5,6,7-trichloroisatoic anhydride.

With respect to Formula XI, particularly preferred compounds which may be used in the practice of the present invention include, but are not limited to 2-nitro-4-quinolone, 6,7-dichloro-2,5-dinitro-4-quinolone, 6,7-dibromo-2,5-dinitro-4-quinolone, 6,7-difluoro-2,5-dinitro-4-quinolone, 6,7-dimethyl-2,5-dinitro-4-quinolone, 5,7-bis(trifluoromethyl)-2-nitro-4-quinolone, 5,7-dimethyl-2-nitro-4-quinolone, 5,7-dichloro-2-nitro-4-quinolone, 5,7-difluoro-2-nitro-4-quinolone, and 5,6,7-trichloro-2-nitro-4-quinolone.

With respect to Formula XII, particularly preferred compounds are quinazoline-2,4-dione, 3-hydroxyquinazoline-2,4-dione, 6,7-dichloro-5-nitro-3-hydroxyquinazoline-2,4-dione, 6,7-dibromo-5-nitro-3-hydroxyquinazoline-2,4-dione, 6,7-difluoro-5-nitro-3-hydroxyquinazoline-2,4-dione, 6,7-dimethyl-5-nitro-3-hydroxyquinazoline-2,4-dione, 5,7-bis-(trifluoromethyl)-3-hydroxyquinazoline-2,4-dione, 5,7-dimethyl-3-hydroxyquinazoline-2,4-dione, 5,7-dichloro-3-hydroxyquinazoline-2,4-dione, 5,7-difluoro-3-hydroxyquinazoline-2,4-dione, and 5,6,7-trichloro-3-hydroxyquinazoline-2,4-dione.

With respect to Formula XIII, particularly preferred compounds are 1,2-dihydro-3-phenyl-quinoxaline-2-one, 6,7-dichloro-5-nitro-1,2-dihydro-3-phenyl-quinoxaline-2-one, 6,7-dibromo-5-nitro-1,2-dihydro-3-phenyl-quinoxaline-2-one, 6,7-difluoro-5-nitro-1,2-dihydro-3-phenyl-quinoxaline-2-one, 6,7-dimethyl-5-nitro-1,2-dihydro-3-phenyl-quinoxaline-2-one, 5,7-bis(trifluoromethyl)-1,2-dihydro-3-phenyl-quinoxaline-2-one, 5,7-dimethyl-1,2-dihydro-3-phenyl-quinoxaline-2-one, 5,7-dichloro-1,2-dihydro-3-phenyl-quinoxaline-2-one, 5,7-difluoro-1,2-dihydro-3-phenyl-quinoxaline-2-one, and 5,6,7-trichloro-1,2-dihydro-3-phenyl-quinoxaline-2-one.

With respect to Formula XIV, particularly preferred compounds are 2,3-dihydroindole-2-one-3-acetic acid, 5,6-dichloro-4-nitro-2,3-dihydroindole-2-one-3-acetic acid, 5,6-dibromo-4-nitro-2,3-dihydroindole-2-one-3-acetic acid, 5,6-difluoro-4-nitro-2,3-dihydroindole-2-one-3-acetic acid, 5,6-dimethyl-4-nitro-2,3-dihydroindole-2-one-3-acetic acid, 4,6-bis(trifluoromethyl)-2,3-dihydroindole-2-one-3-acetic acid, 4,6-dimethyl-2,3-dihydroindole-2-one-3-acetic acid, 4,6-dichloro-2,3-dihydroindole-2-one-3-acetic acid, 4,6-difluoro-2,3-dihydroindole-2-one-3-acetic acid, and 4,5,6-trichloro-2,3-dihydroindole-2-one-3-acetic acid.

With respect to Formula XV, particularly preferred compounds are 3-hydroxy-2-nitroindole, 5,6-dichloro-3-hydroxy-2,4-dinitroindole, 5,6-dibromo-3-hydroxy-2,4-dinitroindole, 5,6-difluoro-3-hydroxy-2,4-dinitroindole, 5,6-dimethyl-3-hydroxy-2,4-dinitroindole, 4,6-bis(trifluoromethyl)-3-hydroxy-2-nitroindole, 4,6-dimethyl-3-hydroxy-2-nitroindole, 4,6-dichloro-3-hydroxy-2-nitroindole, 4,6-difluoro-3-hydroxy-2-nitroindole, 4,5,6-trichloro-3-hydroxy-2-nitroindole.

With respect to Formula XVI, particularly preferred compounds are 2,3,4,5-tetrahydro-1H-1-benzazepine-2,3,4,5-tetraone-4-oxime, 7,8-dichloro-6-nitro-2,3,4,5-tetrahydro-1H-1-benzazepine-2,3,4,5-tetraone-4-oxime, 7,8 -dibromo-6-nitro-2,3,4,5-tetrahydro-1H-1-benzazepine-2,3,4,5-tetraone-4-oxime, 7,8-difluoro-6-nitro-2,3,4,5-tetrahydro-1H-1-benzazepine-2,3,4,5-tetraone-4-oxime, 7,8-dimethyl-6-nitro-2,3,4,5-tetrahydro-1H-1-benzazepine-2,3,4,5-tetraone-4-oxime, 6,8-bis(trifluoromethyl)-2,3,4,5-tetrahydro-1H-1-benzazepine-2,3,4,5-tetraone-4-oxime, 6,8-dimethyl-2,3,4,5-tetrahydro-1H-1-benzazepine-2,3,4,5-tetraone-4-oxime, 6,8-dichloro-2,3,4,5-tetrahydro-1H-1-benzazepine-2,3,4,5-tetraone-4-oxime, 6,8-difluoro-2,3,4,5-tetrahydro-1H-1-benzazepine-2,3,4,5-tetraone-4-oxime, 6,7,8-trichloro-2,3,4,5-tetrahydro-1H-1-2,3,4,5-tetraone-4-oxime, 8-trifluoromethyl-2,3,4,5-tetrahydro-1H-1-benzazepine-2,3,4,5-tetraone-4-oxime, 8-methyl-2,3,4,5-tetrahydro-1H-1-benzazepine-2,3,4,5-tetraone-4-oxime, 8-chloro-2,3,4,5-tetrahydro-1H-1-benzazepine-2,3,4,5-tetraone-4-oxime, and 8-fluoro-2,3,4,5-tetrahydro-1H-1-benzazepine-2,3,4,5-tetraone-4-oxime.

With respect to Formula XVII, particularly preferred compounds are 3-hydroxy-4-nitro-2,5-dihydro-1H-benzazepine-2,5-dione, 7,8-dichloro-3-hydroxy-4,6-dinitro-2,5-dihydro-1H-1-benzazepine-2,5-dione, 7,8-dibromo-3-hydroxy-4,6-dinitro-2,5-dihydro-1 H-1-benzazepine-2,5- dione, 7,8-difluoro-3-hydroxy-4,6-dinitro-2,5-dihydro-1H-1-benzazepine-2,5-dione, 7,8-dimethyl-3-hydroxy-4,6-dinitro-2,5-dihydro-1H-1-benzazepine-2,5-dione, 6,8-bis(trifluoromethyl)-3-hydroxy-4-nitro-2,5-dihydro-1H-1-benzazepine-2,5-dione, 6,8-dimethyl-3-hydroxy-4-nitro-2,5-dihydro-1H-1-benzazepine-2,5-dione, 6,8-dichloro-3-hydroxy-4-nitro-2,5-dihydro-1H-1-benzazepine-2,5-dione, 6,8-difluoro-3-hydroxy-4-nitro-2,5-dihydro-1H-1-benzazepine-2,5-dione, 6,7,8-trichloro-3-hydroxy-4-nitro-2,5-dihydro-1H-1-benzazepine-2,5-dione, 8-trifluoromethyl-3-hydroxy-4-nitro-2,5-dihydro-1H-1-benzazepine-2,5-dione, 8-methyl-3-hydroxy-4-nitro-2,5-dihydro-1H-1-benzazepine-2,5-dione, 8-chloro-3-hydroxy-4-nitro-2,5-dihydro-1H-1-benzazepine-2,5-dione, and 8-fluoro-3-hydroxy-4-nitro-2,5-dihydro-1H-1-benzazepine-2,5-dione.

With respect to Formula XVIII, particularly preferred compounds are 2,3,4,5-tetrahydro-1H-1-benzazepine-2,3,4,5-tetraone-3-oxime, 7,8-dichloro-6-nitro-2,3,4,5-tetrahydro-1H-1-benzazepine-2,3,4,5-tetraone-3-oxime, 7,8-dibromo-6-nitro-2,3,4,5-tetrahydro-1H-benzazepine-2,3,4,5-tetraone-3-oxime, 7,8-difluoro-6-nitro-2,3,4,5-tetrahydro-1H-1-benzazepine-2,3,4,5-tetraone-3-oxime, 7,8-dimethyl-6-nitro-2,3,4,5-tetrahydro-1H-1-benzazepine-2,3,4,5-tetraone-3-oxime, 6,8-bis(trifluoromethyl)-2,3,4,5-tetrahydro-1H-1-benzazepine-2,3,4,5-tetraone-3-oxime, 6,8-dimethyl-2,3,4,5-tetrahydro-1H-1-benzazepine-2,3,4,5-tetraone-3-oxime, 6, 8-dichloro-2,3,4,5-tetrahydro-1H-1-benzazepine-2,3,4,5-tetraone-3-oxime, 6,8-difluoro-2,3,4,5-tetrahydro-1H-1-benzazepine-2,3,4,5-tetraone-3-oxime, 6,7,8-trichloro-2,3,4,5-tetrahydro-1H-1-benzazepine-2,3,4,5-tetraone-3-oxime, 8-trifluoromethyl-2,3,4,5-tetrahydro-1H-1-benzazepine-2,3,4,5-tetraone-3-oxime, 8-methyl-2,3,4,5-tetrahydro-1H-1-benzazepine-2,3,4,5-tetraone-3-oxime, 8-chloro-2,3,4,5-tetrahydro-1H-1-benzazepine-2,3,4,5-tetraone-3-oxime, and 8-fluoro-2,3,4,5-tetrahydro-1H-1-benzazepine-2,3,4,5-tetraone-3-oxime.

With respect to Formula XIX, particularly preferred compounds are 4-hydroxy-3-nitro-2,5-dihydro-1H-1-benzazepine-2,5-dione, 7,8-dichloro-4-hydroxy-3,6-dinitro-2,5-dihydro-1H-1-benzazepine-2,5-dione, 7,8-dibromo-4-hydroxy-3,6-dinitro-2,5-dihydro-1H-1-benzazepine-2,5-dione, 7,8-difluoro-4-hydroxy-3,6-dinitro-2,5-dihydro-1H-1-benzazepine-2,5-dione, 7,8-dimethyl-4-hydroxy-3,6-dinitro-2,5-dihydro-1H-1-benzazepine-2,5-dione, 6,8-bis(trifluoromethyl)-4-hydroxy-3-nitro-2,5-dihydro-1H-1-benzazepine-2,5-dione, 6,8-dimethyl-4-hydroxy-3-nitro-2,5-dihydro-1H-1-benzazepine-2,5-dione, 6,8-dichloro-4-hydroxy-3-nitro-2,5-dihydro-1H-1-benzazepine-2,5-dione, 6,8-difluoro-4-hydroxy-3-nitro-2,5-dihydro-1H-1-benzazepine-2,5-dione, 6,7,8-trichloro-4-hydroxy-3-nitro-2,5-dihydro-1H-1-benzazepine-2,5-dione, 8-trifluoromethyl-4-hydroxy-3-nitro-2,5-dihydro-1H-1-benzazepine-2,5-dione, 8-methyl-4-hydroxy-3-nitro-2,5-dihydro-1H-1-benzazepine-2,5-dione, 8-chloro-4-hydroxy-3-nitro-2,5-dihydro-1H-1-benzazepine-2,5-dione, and 8-fluoro-4-hydroxy-3-nitro-2,5-dihydro-1H-1-benzazepine-2,5-dione.

With respect to Formula XX, particularly preferred compounds which may be used in the practice of the present invention include, but are not limited to 2-boronato-4-quinolone, 6,7-dichloro-5-nitro-2-boronato-4-quinolone, 6,7-dibromo-5-nitro-2-boronato-4-quinolone, 6,7-difluoro-5-nitro-2-boronato-4-quinolone, 6,7-dimethyl-5-nitro-2-boronato-4-quinolone, 5,7-bis(trifluoromethyl)-2-boronato-4-quinolone, 5,7-dimethyl-2-boronato-4-quinolone, 5,7-dichloro-2-boronato-4-quinolone, 5,7-difluoro-2-boronato-4-quinolone, and 5,6,7-trichloro-2-boronato-4-quinolone.

With respect to Formula XXI, particularly preferred compounds are 4-hydroxy-3-methyl-4,3-boraza-2-quinolone, 4-hydroxy-3-phenyl-4,3-boraza-2-quinolone, 4-hydroxy-3-benzyl-4,3-boraza-2-quinolone, 6,7-dichloro-5-nitro-4-hydroxy-3-methyl-4,3-boraza-2-quinolone, 6,7-dibromo-5-nitro-4-hydroxy-3-methyl-4,3-boraza-2-quinolone, 6,7-difluoro-5-nitro-4-hydroxy-3-methyl-4,3-boraza-2-quinolone, 6,7-dimethyl-5-nitro-4-hydroxy-3-benzyl-4,3-boraza-2-quinolone, 5,7-bis(trifluoromethyl)-4-hydroxy-3-benzyl-4,3-boraza-2-quinolone, 5,7-dimethyl-4-hydroxy-3-benzyl-4,3-boraza-2-quinolone, 5,7-dichloro-4-hydroxy-3-benzyl-4,3-boraza-2-quinolone, 5,7-difluoro-4-hydroxy-3-benzyl-4,3-boraza-2-quinolone, 5,6,7-trichloro-4-hydroxy-3-benzyl-4,3-boraza-2-quinolone, 6,7-dimethyl-5-nitro-4-hydroxy-3-phenyl-4,3-boraza-2-quinolone, 5,7-bis(trifluoromethyl)-4-hydroxy-3-phenyl-4,3-boraza-2-quinolone, 5,7-dimethyl-4-hydroxy-3-phenyl-4,3-boraza-2-quinolone, 5,7-dichloro-4-hydroxy-3-phenyl-4,3-boraza-2-quinolone, 5,7-difluoro-4-hydroxy-3-phenyl-4,3-boraza-2-quinolone, and 5,6,7-trichloro-4-hydroxy-3-phenyl-4,3-boraza-2-quinolone.

With respect to Formula XXII, particularly preferred compounds which may be used in the practice of the invention include, but are not limited to 4,4-dihydroxy-3,3-dimethyl-4,3-boraza-2-quinolone, 6,7-dichloro-5-nitro-4,4-dihydroxy-3,3-dimethyl-4,3-boraza-2-quinolone, 6,7-dibromo-5-nitro-4,4-dihydroxy-3,3-dimethyl-4,3-boraza-2-quinolone, 6,7-difluoro-5-nitro-4,4-dihydroxy-3,3-dimethyl-4,3-boraza-2-quinolone, 6,7-dimethyl-5-nitro-4,4-dihydroxy-3,3-dimethyl-4,3-boraza-2-quinolone, 5,7-bis(trifluoromethyl)-4,4-dihydroxy-3,3-dimethyl-4,3-boraza-2-quinolone, 5,7-dimethyl-4,4-dihydroxy-3,3-dimethyl-4,3-boraza-2-quinolone, 5,7-dichloro-4,4-dihydroxy-3,3-dimethyl-4,3-boraza-2-quinolone, 5,7-difluoro-4,4-dihydroxy-3,3-dimethyl-4,3-boraza-2-quinolone, and 5,6,7-trichloro-4,4-dihydroxy-3,3-dimethyl-4,3-boraza-2-quinolone.

With respect to Formula XXIII, particularly preferred compounds which may be used in the practice of the present invention include, but are not limited to 2-nitro-3-carboxymethylindole, 5,6-dichloro-2,4-dinitro-3-carboxymethylindole, 5,6-dibromo-2,4-dinitro-3-carboxymethylindole, 5,6-difluoro-2,4-dinitro-3-carboxymethylindole, 5,6-dimethyl-2,4-dinitro-3-carboxymethylindole, 4,6-bis(trifluoromethyl)-2-nitro-3-carboxymethylindole, 4,6-dimethyl-2-nitro-3-carboxymethylindole, 4,6-dichloro-2-nitro-3-carboxymethylindole, 4,6-difluoro-2-nitro-3-carboxymethylindole, and 4,5,6-trichloro-2-nitro-3-carboxymethylindole.

With respect to Formula XXIV, particularly preferred compounds which may be used in the practice of the present invention include, but are not limited to 3-(nitromethyl)-2-carboxylindole, 5,6-dichloro-4-nitro-3-(nitromethyl)-2-carboxylindole, 5,6-dibromo-4-nitro-3-(nitromethyl)-2-carboxylindole, 5,6-difluoro-4-nitro-3-(nitromethyl)-2-carboxylindole, 5,6-dimethyl-4-nitro-3-(nitromethyl)-2-carboxylindole, 4,6-bis(trifluoromethyl)-3-(nitromethyl)-2-carboxylindole, 4,6-dimethyl-3-(nitromethyl)-2-carboxylindole, 4,6-dichloro-3-(nitromethyl)-2-carboxylindole, 4,6-difluoro-3-(nitromethyl)-2-carboxylindole, and 4,5,6-trichloro-3-(nitromethyl)-2-carboxylindole.

With respect to Formula XXV, particularly preferred compounds which may be used in the practice of the present invention include, but are not limited to 2-nitro-3-(nitromethyl)indole, 5,6-dichloro-2,4-dinitro-3-(nitromethyl)indole, 5,6-dibromo-2,4-dinitro-3-(nitromethyl)indole, 5,6-difluoro-2,4-dinitro-3-(nitromethyl)indole, 5,6-dimethyl-2,4-dinitro-3-(nitromethyl)indole, 4,6-bis(trifluoromethyl)-2- nitro-3-(nitromethyl)indole, 4,6-dimethyl-2-nitro-3-(nitromethyl)indole, 4,6-dichloro-2-nitro-3-(nitromethyl)indole, 4,6-difluoro-2-nitro-3-(nitromethyl)indole, and 4,5,6-trichloro-2-nitro-3-(nitromethyl)indole.

With respect to Formula XXVI, particularly preferred compounds which may be used in the practice of the present invention include, but are not limited to 1,2-dihydro-3-nitroquinoxaline-2-one, 1,2-dihydro-6,7-dichloro-3,5-dinitro-quinoxaline-2-one, 1,2-dihydro-6,7-dibromo-3,5-dinitro-quinoxaline-2-one, 1,2-dihydro-6,7-difluoro-3,5-dinitroquinoxaline-2-one, 1,2-dihydro-6,7-dimethyl-3,5-dinitroquinoxaline-2-one, 1,2-dihydro-5,7-bis(trifluoromethyl)-3-nitro-quinoxaline-2-one, 1,2-dihydro-5,7-dimethyl-3-nitroquinoxaline-2-one, 1,2-dihydro-5,7-dichloro-3-nitroquinoxaline-2-one, 1,2-dihydro-5,7-difluoro-3-nitroquinoxaline-2-one, and 1,2-dihydro-5,6,7-trichloro-3-nitroquinoxaline-2-one.

With respect to Formula XXVII, particularly preferred compounds which may be used in the practice of the present invention include, but are not limited to 1,2,3,4-tetrahydro-3-nitro-quinoxaline-2-one, 1,2,3,4-tetrahydro-6,7-dichloro-3,5-dinitro-quinoxaline-2-one, 1,2,3,4-tetrahydro-6,7-dibromo-3,5-dinitro-quinoxaline-2-one, 1,2,3,4-tetrahydro-6,7-difluoro-3,5-dinitro-quinoxaline-2-one, 1,2,3,4-tetrahydro-6,7-dimethyl-3,5-dinitro-quinoxaline-2-one, 1,2,3,4-tetrahydro-5,7-bis(trifluoromethyl)-3-nitro-quinoxaline-2-one, 1,2,3,4-tetrahydro-5,7-dimethyl-3-nitro-quinoxaline-2-one, 1,2,3,4-tetrahydro-5,7-dichloro-3-nitro-quinoxaline-2-one, 1,2,3,4-tetrahydro-5,7-difluoro-3-nitro-quinoxaline-2-one, and 1,2,3,4-tetrahydro-5,6,7-trichloro-3-nitro-quinoxaline-2-one.

With respect to Formula XXVIII, particularly preferred compounds which may be used in the practice of the present invention include, but are not limited to 2,5-dihydro-1H-1-benzazepine-2,5-dione, 7,8-dichloro-6-nitro-2,5-dihydro-1H-1-benzazepine-2,5-dione, 7,8-dibromo-6-nitro-2,5-dihydro-1H-1-benzazepine-2,5-dione, 7,8-difluoro-6-nitro-2,5-dihydro-1H-1-benzazepine-2,5-dione, 7,8-dimethyl-6-nitro-2,5-dihydro-1H-1-benzazepine-2,5-dione, 6,8-bis(trifluoromethyl)-2,5-dihydro-1H-1-benzazepine-2,5-dione, 6,8-dimethyl-2,5-dihydro-1H-1-benzazepine-2,5-dione, 6,8-dichloro-2,5-dihydro-1H-1-benzazepine-2,5-dione, 6,8-difluoro-2,5-dihydro-1H-1-benzazepine-2,5-dione, 6,7,8-trichloro-2,5-dihydro-1H-1-benzazepine-2,5-dione, 8-trifluoromethyl-2,5-dihydro-1H-1-benzazepine-2,5-dione, 8-methyl-2,5-dihydro-1H-1-benzazepine-2,5-dione, 8-chloro-2,5-dihydro-1H-1-benzazepine-2,5-dione, and 8-fluoro-2,5-dihydro-1H-1-benzazepine-2,5-dione.

With respect to Formula XXIX, particularly preferred compounds which may be used in the practice of the present invention include, but are not limited to 2,3,5-trihydro-1H, 4H-1,4-benzodiazepine-2,3,5-trione-3-oxime, 7,8-dichloro-6-nitro-2,3,5-trihydro-1H, 4H-1,4-benzodiazepine-2,3,5-trione-3-oxime, 7,8-dibromo-6-nitro-2,3,5-trihydro-1H, 4H-1,4-benzodiazepine-2,3,5-trione-3-oxime, 7,8-difluoro-6-nitro-2,3,5-trihydro-1H, 4H-1,4-benzodiazepine-2,3,5-trione-3-oxime, 7,8-dimethyl-6-nitro-2,3,5-trihydro-1H,4H-1,4-benzodiazepine-2,3,5-trione-3-oxime, 6,8-bis(trifluoromethyl)-2,3,5-trihydro-1H,4H-1,4-benzodiazepine-2,3,5-trione-3-oxime, 6,8-dimethyl-2,3,5-trihydro-1H, 4H-1,4-benzodiazepine-2,3,5-trione-3-oxime, 6,8-dichloro-2,3,5-trihydro-1H,4H-1,4-benzodiazepine-2,3,5-trione-3-oxime, 6,8-difluoro-2,3,5-trihydro-1H, 4H-1,4-benzodiazepine-2,3,5-trione-3-oxime, 6,7,8-trichloro-2,3,5-trihydro-1H,4H-1,4-benzodiazepine-2,3,5-trione-3-oxime, 8-trifluoromethyl-2,3,5-trihydro-1H, 4H-1,4-benzodiazepine-2,3,5-trione-3-oxime, 8-methyl-2,3,5-trihydro-1H, 4H-1,4-benzodiazepine-2,3,5-trione-3-oxime, 8-chloro-2,3,5-trihydro-1H,4H-1,4-benzodiazepine-2,3,5-trione-3-oxime, and 8-fluoro-2,3,5-trihydro-1H, 4H-1,4-benzodiazepine-2,3,5-trione-3-oxime.

With respect to Formula XXX, particularly preferred compounds which may be used in the practice of the present invention include, but are not limited to 3-benzyl-2,3,5-trihydro-1H,4H-1,4-benzodiazepine-2,5-dione, 7,8-dichloro-6-nitro-3-benzyl-2,3,5-trihydro-1H,4H-1,4-benzodiazepine-2,5-dione, 7,8-dibromo-6-nitro-3-benzyl-2,3,5-trihydro-1H, 4H-1,4-benzodiazepine-2,5-dione, 7,8-difluoro-6-nitro-3-benzyl-2,3,5-trihydro-1H,4H-1,4-benzodiazepine-2,5-dione, 7,8-dimethyl-6-nitro-3-benzyl-2,3,5-trihydro-1H,4H-1,4-benzodiazepine-2,5-dione, 6,8-bis(trifluoromethyl)-3-benzyl-2,3,5-trihydro-1H, 4H-1,4-benzodiazepine-2,5-dione, 6,8-dimethyl-3-benzyl-2,3,5-trihydro-1H,4H-1,4-benzodiazepine-2,5-dione, 6,8-dichloro-3-benzyl-2,3,5-trihydro-1H, 4H-1,4-benzodiazepine-2,5-dione, 6,8-difluoro-3-benzyl-2,3,5-trihydro-1H, 4H-1,4-benzodiazepine-2,5-dione, 6,7,8-trichloro-3-benzyl-2,3,5-trihydro- 1H,4H-1,4-benzodiazepine-2,5-dione, 8-trifluoromethyl-3-benzyl-2,3,5-trihydro-1H,4H-1,4-benzodiazepine-2,5-dione, 8-methyl-3-benzyl-2,3,5-trihydro-1H,4H-1,4-benzodiazepine-2,5-dione, 8-chloro-3-benzyl-2,3,5-trihydro-1H,4H-1,4-benzodiazepine-2,5-dione, and 8-fluoro-3-benzyl-2,3,5-trihydro-1H, 4H-1,4-benzodiazepine-2,5-dione.

With respect to Formula XXXI, particularly preferred compounds which may be used in the practice of the present invention include, but are not limited to 3-nitro-2,3,5-trihydro-1H,4H-1,4-benzodiazepine-2,5-dione, 7,8-dichloro-3,6-dinitro-2,3,5-trihydro-1H, 4H-1,4-benzodiazepine-2,5-dione, 7,8-dibromo-3,6-dinitro-2,3,5-trihydro-1H, 4H-1,4-benzodiazepine-2,5-dione, 7,8-difluoro-3,6-dinitro-2,3,5-trihydro-1H, 4H-1,4-benzodiazepine-2,5-dione, 7,8-dimethyl-3,6-dinitro-2,3,5-trihydro-1H,4H-1,4-benzodiazepine-2,5-dione, 6,8-bis(trifluoromethyl)-3-nitro-2,3,5-trihydro-1H, 4H-1,4-benzodiazepine-2,5-dione, 6,8-dimethyl-3-nitro-2,3,5-trihydro-1H,4H-1,4-benzodiazepine-2,5-dione, 6,8-dichloro-3-nitro-2,3,5-trihydro-1H, 4H-1,4-benzodiazepine-2,5-dione, 6,8-difluoro-3-nitro-2,3,5-trihydro-1H,4H-1,4-benzodiazepine-2,5-dione, 6,7,8-trichloro-3-nitro-2,3,5-trihydro-1H,4H-1,4-benzodiazepine-2,5-dione, 8-trifluoromethyl-3-nitro-2,3,5-trihydro-1H,4H-1,4-benzodiazepine-2,5-dione, 8-methyl-3-nitro-2,3,5-trihydro-1H,4H-1,4-benzodiazepine-2,5-dione, 8-chloro-3-nitro-2,3,5-trihydro-1H,4H-1,4-benzodiazepine-2,5-dione, and 8-fluoro-3-nitro-2,3,5-trihydro-1H,4H-1,4-benzodiazepine-2,5-dione.

With respect to Formula XXXII, particularly preferred compounds which may be used in the practice of the present invention include, but are not limited to 2,3-dihydro-1H-1-benzazepine-2,3-dione, 7,8-dichloro-6-nitro-2,3-dihydro-1H-1-benzazepine-2,3-dione, 7,8-dibromo-6-nitro-2,3-dihydro-1H-1-benzazepine-2,3-dione, 7,8-difluoro-6-nitro-2,3-dihydro-1H-1-benzazepine-2,3-dione, 7,8-dimethyl-6-nitro-2,3-dihydro-1H-1-benzazepine-2,3-dione, 6,8-bis(trifluoromethyl)-2,3-dihydro-1H-1-benzazepine-2,3-dione, 6,8-dimethyl-2,3-dihydro-1H-1-benzazepine-2,3-dione, 6,8-dichloro-2,3-dihydro-1H-1-benzazepine-2,3-dione, 6,8-difluoro-2,3-dihydro-1H-1-benzazepine-2,3-dione, 6,7,8-trichloro-2,3-dihydro-1H-1-benzazepine-2,3-dione, 8-trifluoromethyl-2,3 -dihydro-1H-1-benzazepine-2,3-dione, 8-methyl-2,3-dihydro-1H-1-benzazepine-2,3-dione, 8-chloro-2,3-dihydro-1H-1-benzazepine-2,3-dione, and 8-fluoro-2,3-dihydro-1H-1-benzazepine-2,3-dione.

With respect to Formula XXXIII, particularly preferred compounds which may be used in the practice of the present invention include, but are not limited to 2,3,5-trihydro-1H-4,1-benzoxazepine-2,3-dione, 7,8-dichloro-6-nitro-2,3,5-trihydro-1H-4,1-benzoxazepine-2,3-dione, 7,8-dibromo-6-nitro-2,3,5-trihydro-1H4,1-benzoxazepine-2,3-dione, 7,8-difluoro-6-nitro-2,3,5-trihydro-1H-4,1-benzoxazepine-2,3-dione, 7,8-dimethyl-6-nitro-2,3,5-trihydro-1H-4,1-benzoxazepine-2,3-dione, 6,8-bis(trifluoromethyl)-2,3,5-trihydro-1H-4,1-benzoxazepine-2,3-dione, 6,8-dimethyl-2,3,5-trihydro-1H-4,1-benzoxazepine-2,3-dione, 6,8-dichloro-2,3,5-trihydro-1H-4,1-benzoxazepine-2,3-dione, 6,8-difluoro-2,3,5-trihydro-1H-4,1-benzoxazepine-2,3-dione, 6,7,8-trichloro-2,3,5-trihydro-1H-4,1-benzoxazepine-2,3-dione, 8-trifluoromethyl-2,3,5-trihydro-1H-4,1-benzoxazepine-2,3-dione, 8-methyl-2,3,5-trihydro-1H-4,1-benzoxazepine-2,3-dione, 8-chloro-2,3,5-trihydro-1H-4,1-benzoxazepine-2,3-dione, and 8-fluoro-2,3,5-trihydro-1H-4,1-benzoxazepine-2,3-dione.

With respect to Formula XXXIV, particularly preferred compounds which may be used in the practice of the present invention include, but are not limited to 4-hydroxy-2,3-dihydro-1H-1-benzazepine-2,3-dione, 4-hydroxy-7,8-dichloro-6-nitro-2,3-dihydro-1H-1-benzazepine-2,3-dione, 4-hydroxy-7,8-dibromo-6-nitro-2,3-dihydro-1H-1-benzazepine-2,3-dione, 4-hydroxy-7,8-difluoro-6-nitro-2,3-dihydro-1H-1-benzazepine-2,3-dione, 4-hydroxy-7,8-dimethyl-6-nitro-2,3-dihydro-1H-1-benzazepine-2,3-dione, 4-hydroxy-6,8-bis(trifluoromethyl)-2,3-dihydro-1H-1-benzazepine-2,3-dione, 4-hydroxy-6,8-dimethyl-2,3-dihydro-1H-1-benzazepine-2,3-dione, 4-hydroxy-6,8-dichloro-2,3-dihydro-1H-1-benzazepine-2,3-dione, 4-hydroxy-6,8-difluoro-2,3-dihydro-1H-1-benzazepine-2,3-dione, 4-hydroxy-6,7,8-trichloro-2,3-dihydro-1H-1-benzazepine-2,3-dione, 4-hydroxy-8-trifluoromethyl-2,3-dihydro-1H-1-benzazepine-2,3-dione, 4-hydroxy-8-methyl-2,3-dihydro-1H-1-benzazepine-2,3 -dione, 4-hydroxy-8-chloro-2,3-dihydro-1H-1-benzazepine-2,3-dione, and 4-hydroxy-8-fluoro-2,3-dihydro-1H-1-benzazepine-2,3-dione.

With respect to Formula XXXV, particularly preferred compounds which may be used in the practice of the present invention include, but are not limited to 2,3,5-trihydro-1H, 4H-1,4-benzodiazepine-2,3-dione, 7,8-dichloro-6-nitro-2,3,5-trihydro-1H,4H-1,4-benzodiazepine-2,3-dione, 7,8-dibromo-6-nitro-2,3,5-trihydro-1H, 4H-1,4-benzodiazepine-2,3-dione, 7,8-difluoro-6-nitro-2,3,5-trihydro-1H,4H-1,4-benzodiazepine-2,3-dione, 7,8-dimethyl-6-nitro-2,3,5-trihydro-1H,4H-1,4-benzodiazepine-2,3-dione, 6,8-bis(trifluoromethyl)-2,3,5-trihydro-1H,4H-1,4-benzodiazepine-2,3-dione, 6,8-dimethyl-2,3,5-trihydro-1H, 4H-1,4-benzodiazepine-2,3-dione, 6,8-dichloro-2,3,5-trihydro-1H,4H-1,4-benzodiazepine-2,3-dione, 6,8-difluoro-2,3,5-trihydro-1H,4H-1,4-benzodiazepine-2,3-dione, 6,7,8-trichloro-2,3,5-trihydro-1H,4H-1,4-benzodiazepine-2,3-dione, 8-trifluoromethyl-2,3,5-trihydro-1H,4H-1,4-benzodiazepine-2,3-dione, 8-methyl-2,3,5-trihydro-1H,4H-1,4-benzodiazepine-2,3-dione, 8-chloro-2,3,5-trihydro-1H,4H-1,4-benzodiazepine-2,3-dione, and 8-fluoro-2,3,5-trihydro-1H, 4H-1,4-benzodiazepine-2,3-dione.

With respect to Formula XXXVI, particularly preferred compounds which may be used in the practice of the present invention include, but are not limited to 2,3,5-trihydro-1H, 4H-1,4-benzodiazepine-2,3,5-trione, 7,8-dichloro-6-nitro-2,3,5-trihydro-1H,4H-1,4-benzodiazepine-2,3,5-trione, 7,8-dibromo-6-nitro-2,3,5-trihydro-1H,4H-1,4-benzodiazepine-2,3,5-trione, 7,8-difluoro-6-nitro-2,3,5-trihydro-1H,4H-1,4-benzodiazepine-2,3,5-trione, 7,8-dimethyl-6-nitro-2,3,5-trihydro-1H,4H, 1,4-benzodiazepine-2,3,5-trione, 6,8-bis(trifluoromethyl)-2,3,5-trihydro-1H,4H-1,4-benzodiazepine-2,3,5-trione, 6,8-dimethyl-2,3,5-trihydro-1H,4H-1,4-benzodiazepine-2,3,5-trione, 6,8-dichloro-2,3,5-trihydro-1H, 4H-1,4-benzodiazepine-2,3,5-trione, 6,8-difluoro-2,3,5-trihydro-1H, 4H-1,4-benzodiazepine-2,3,5-trione, 6,7,8-trichloro-2,3,5-trihydro-1H,4H-1,4-benzodiazepine-2,3,5-trione, 8-trifluoromethyl-2,3,5-trihydro-1H,4H-1,4-benzodiazepine-2,3,5-trione, 8-methyl-2,3,5-trihydro-1H,4H-1,4-benzodiazepine-2,3,5-trione, 8-chloro-2,3,5-trihydro-1H,4H-1,4 -benzodiazepine-2,3,5-trione, and 8-fluoro-2,3,5-trihydro-1H,4H-1,4-benzodiazepine-2,3,5-trione.

With respect to Formula XXXVII, particularly preferred compounds which may be used in the practice of the present invention include, but are not limited to 2,3,5-trihydro-1H, 4H-1,4-benzodiazepine-2,5-dione, 7,8-dichloro-6-nitro-2,3, 5-trihydro-1H,4H-1,4-benzodiazepine-2,5-dione, 7,8-dibromo-6-nitro-2,3,5-trihydro-1H,4H-1,4-benzodiazepine-2, 5-dione, 7,8-difluoro-6-nitro-2,3,5-trihydro-1H,4H-1,4-benzodiazepine-2,5-dione, 7,8-dimethyl-6-nitro-2,3,5-trihydro-1H,4H-1,4-benzodiazepine-2,5-dione, 6,8-bis(trifluoromethyl)-2,3,5trihydro-1H,4H-1,4-benzodiazepine-2,5-dione, 6,8-dimethyl-2,3,5-trihydro-1H, 4H-1,4-benzodiazepine-2,5-dione, 6,8-dichloro-2,3,5-trihydro-1H,4H-1,4-benzodiazepine-2,5-dione, 6,8-difluoro-2,3,5-trihydro-1H,4H-1,4-benzodiazepine-2,5-dione, 6,7,8-trichloro-2,3,5-trihydro-1H,4H-1,4-benzodiazepine-2,5-dione, 8-trifluoromethyl-2,3,5-trihydro-1H, 4H-1,4-benzodiazepine-2,5-dione, 8-methyl-2,3,5-trihydro-1H,4H-1,4-benzodiazepine-2,5-dione, 8-chloro-2, 3,5-trihydro-1H,4H-1,4-benzodiazepine-2,5-dione, and 8-fluoro-2,3,5-trihydro-1H, 4H-1, 4-benzodiazepine-2,5-dione.

With respect to Formula XXXVIII, particularly preferred compounds which may be used in the practice of the present invention include, but are not limited to 2,3-dihydro-1H-1, 5-benzodiazepine-2,3-dione, 7,8-dichloro-6-nitro-2,3-dihydro-1H-1,5-benzodiazepine-2,3-dione, 7,8-dibromo-6-nitro-2,3-dihydro-1H-1,5-benzodiazepine-2,3-dione, 7,8-difluoro-6-nitro-2,3-dihydro-1H-1,5-benzodiazepine-2,3-dione, 7,8-dimethyl-6-nitro-2,3-dihydro-1H-1,5-benzodiazepine-2,3-dione, 6,8-bis(trifluoromethyl)-2,3-dihydro-1H-1,5-benzodiazepine-2,3-dione, 6,8-dimethyl-2, 3-dihydro-1H-1,5-benzodiazepine-2,3-dione, 6,8-dichloro-2,3-dihydro-1H, 1,5-benzodiazepine-2,3-dione, 6,8-difluoro-2,3-dihydro-1H-1,5-benzodiazepine-2,3-dione, 6,7, 8-trichloro-2,3-dihydro-1H-1,5-benzodiazepine-2,3-dione, 8-trifluoromethyl-2,3-dihydro-1H-1,5-benzodiazepine-2,3-dione, 8-methyl-2,3-dihydro-1H-1,5-benzodiazepine-2,3-dione, 8-chloro-2,3-dihydro-1H-1,5-benzodiazepine-2,3-dione, and 8-fluoro-2,3-dihydro-1H-1,5-benzodiazepine-2,3-dione.

With respect to Formula XXXIX, particularly preferred compounds which may be used in the practice of the present invention include, but are not limited to 2,3,4-trihydro-1H, 5H-1,5-benzodiazepine-2,3,4-trione, 7,8-dichloro-6-nitro-2, 3,4-trihydro-1H,5H-1,5-benzodiazepine-2,3,4-trione, 7,8-dibromo-6-nitro-2,3,4-trihydro-1H, 5H-1,5-benzodiazepine-2,3,4-trione, 7,8-difluoro-6-nitro-2,3,4-trihydro-1H,5H-1,5-benzodiazepine-2,3,4-trione, 7,8-dimethyl-6-nitro-2,3,4-trihydro-1H,5H-1,5-benzodiazepine-2,3,4-trione, 6,8-bis(trifluoromethyl)-2,3,4-trihydro-1H,5 H-1,5-benzodiazepine-2,3,4-trione, 6,8-dimethyl-2,3,4-trihydro-1H,5H-1,5-benzodiazepine-2,3,4-trione, 6,8-dichloro-2,3,4-trihydro-1H,5H-1,5-benzodiazepine-2,3,4- trione, 6,8-difluoro-2,3,4-trihydro-1H,5H-1,5-benzodiazepine-2,3,4-trione, 6,7,8-trichloro-2,3,4-trihydro-1H,5H-1,5-benzodiazepine-2,3,4-trione, 8-trifluoromethyl-2,3,4-trihydro-1H,5H-1,5-benzodiazepine-2,3,4-trione, 8-methyl-2,3,4-trihydro-1H,5H-1,5-benzodiazepine-2,3,4-trione, 8-chloro-2,3,4-trihydro-1H,5H-1,5-benzodiazepine-2,3,4-trione, and 8-fluoro-2,3,4-trihydro-1H,5 H-1,5-benzodiazepine-2,3,4-trione.

With respect to Formula XL, particularly preferred compounds are 3-[(butylamino)methylene]-2,3,4-trihydro-1H,5H-1,5-benzodiazepine-2,4-dione, 3-[(butylamino)methylene]-7,8-dichloro-6-nitro-2,3,4-trihydro-1H,5H-1,5-benzodiazepine-2,4-dione, 3-[(butylamino)methylene]-7,8-dibromo-6-nitro-2,3,4-trihydro-1H,5H-1,5-benzodiazepine-2,4-dione, 3-[(butylamino)methylene]-7,8-difluoro-6-nitro-2,3,4-trihydro-1H,5H-1,5-benzodiazepine-2,4-dione, 3-[(butylamino)methylene]-7,8-dimethyl-6-nitro-2,3,4-trihydro-1H,5H-1,5-benzodiazepine-2,4-dione, 3-[(butylamino)methylene]-6,8-bis(trifluoromethyl)-2,3,4-trihydro-1H,5H-1,5-benzodiazepine-2,4-dione, 3-[(butylamino)methylene]-6,8-dimethyl-2,3,4-trihydro-1H,5H-1,5-benzodiazepine-2,4-dione, 3-[(butylamino)methylene]-6,8-dichloro-2,3,4-trihydro-1H,5H-1,5-benzodiazepine-2,4-dione, 3-[(butylamino)methylene]-6,8-difluoro-2,3,4-trihydro-1H,5H-1,5-benzodiazepine-2,4-dione, 3-[(butylamino)methylene]-6,7,8-trichloro-2,3,4-trihydro-1H, 5H-1,5-benzodiazepine-2,4-dione, 3-[(butylamino)methylene]-8 -trifluoromethyl-2,3,4-trihydro-1H,5H-1,5-benzodiazepine-2,4-dione, 3-[(butylamino)methylene]-8-methyl-2,3,4-trihydro-1H,5H-1,5-benzodiazepine-2,4-dione, 3-[(butylamino)methylene]-8-chloro-2,3,4-trihydro-1H,5H-1,5-benzodiazepine-2,4-dione, and 3-[(butylamino)methylene]-8-fluoro-2,3,4-trihydro-1H,5H-1,5-benzodiazepine-2,4-dione.

With respect to Formula XLI, particularly preferred compounds which may be used in the practice of the present invention include, but are not limited to 3-nitro-2,3,4-trihydro-1H, 5H-1,5-benzodiazepine-2,4-dione, 7,8-dichloro-3,6-dinitro-2,3,4-trihydro-1H,5H-1,5-benzodiazepine-2,4-dione, 7,8-dibromo-3,6-dinitro-2,3,4-trihydro-1H, 5H-1,5-benzodiazepine-2,4-dione, 7,8-difluoro-3,6-dinitro-2,3,4-trihydro-1H,5H-1,5-benzodiazepine-2,4-dione, 7,8-dimethyl-3,6-dinitro-2,3,4-trihydro-1H,5H-1,5-benzodiazepine-2,4-dione, 6,8-bis(trifluoromethyl)-3-nitro-2,3,4-trihydro-1H,5H-1,5-benzodiazepine-2,4-dione, 6,8-dimethyl-3-nitro-2,3,4-trihydro-1H,5H-1,5-benzodiazepine-2,4-dione, 6,8-dichloro-3-nitro-2,3,4-trihydro-1H, 5H-1,5-benzodiazepine-2,4-dione, 6,8-difluoro-3-nitro-2,3,4-trihydro-1H,5H-1,5-benzodiazepine-2,4-dione, 6,7,8-trichloro-3-nitro-2,3,4-trihydro-1H, 5H-1,5-benzodiazepine-2,4-dione, 8-trifluoromethyl-3-nitro-2,3,4-trihydro-1H,5H-1,5-benzodiazepine-2,4-dione, 8-methyl-3-nitro-2,3,4-trihydro-1H,5H-1,5-benzodiazepine-2,4-dione, 8-chloro-3-nitro-2,3,4-trihydro-1H,5H-1,5-benzodiazepine-2,4-dione, and 8-fluoro-3-nitro-2,3,4-trihydro-1H,5H-1,5-benzodiazepine-2,4-dione.

With respect to Formula XLII, particularly preferred compounds which may be used in the practice of the present invention include, but are not limited to 2-carbamoyl-3-acetyl-1,4-dihydroquinoxaline, 6,7-dichloro-5-nitro-2-carbamoyl-3-acetyl-1,4-dihydroquinoxaline, 6,7-dibromo-5-nitro-2-carbamoyl-3-acetyl-1,4-dihydroquinoxaline, 6,7-difluoro-5-nitro-2-carbamoyl-3-acetyl-1,4-dihydroquinoxaline, 6,7-dimethyl-5-nitro-2-carbamoyl-3-acetyl-1,4-dihydroquinoxaline, 5,7-bis(trifluoromethyl)-2-carbamoyl-3-acetyl-1,4-dihydroquinoxaline, 5,7-dimethyl-2-carbamoyl-3-acetyl-1,4-dihydroquinoxaline, 5,7-dichloro-2-carbamoyl-3-acetyl-1,4-dihydroquinoxaline, 5,7-difluoro-2-carbamoyl-3-acetyl-1,4 -dihydroquinoxaline, and 5,6,7-trichloro-2-carbamoyl-3-acetyl-1,4-dihydroquinoxaline.

With respect to Formula XLIII, particularly preferred compounds are 2-carbamoyl-3-phenyl-1,4-dihydroquinoxaline, 6,7-dichloro-5-nitro-2-carbamoyl-3-phenyl-1,4-dihydroquinoxaline, 6,7-dibromo-5-nitro-2-carbamoyl-3-phenyl-1,4-dihydroquinoxaline, 6,7-difluoro-5-nitro-2-carbamoyl-3-phenyl-1,4-dihydroquinoxaline, 6,7-dimethyl-5-nitro-2-carbamoyl-3-phenyl-1,4-dihydroquinoxaline, 5,7-bis(trifluoromethyl)-2-carbamoyl-3-phenyl-1,4-dihydroquinoxaline, 5,7-dimethyl-2-carbamoyl-3-phenyl-1,4-dihydroquinoxaline, 5,7-dichloro-2-carbamoyl-3-phenyl-1,4-dihydroquinoxaline, 5,7-difluoro-2-carbamoyl-3-phenyl-1,4-dihydroquinoxaline, and 5,6,7-trichloro-2-carbamoyl-3-phenyl-1,4-dihydroquinoxaline.

With respect to Formula XLIV, particularly preferred compounds are 2,3-dicarbamoyl-1,4-dihydroquinoxaline, 6,7-dichloro-5-nitro-2,3-dicarbamoyl-1,4-dihydroquinoxaline, 6,7-dibromo-5-nitro-2,3-dicarbamoyl-1,4-dihydroquinoxaline, 6,7-difluoro-5-nitro-2,3-dicarbamoyl-1,4-dihydroquinoxaline, 6,7-dimethyl-5-nitro-2,3-dicarbamoyl-1,4-dihydroquinoxaline, 5,7-bis(trifluoromethyl)-2,3-dicarbamoyl-1,4-dihydroquinoxaline, 5,7-dimethyl-2,3-dicarbamoyl-1,4-dihydroquinoxaline, 5,7-dichloro-2,3-dicarbamoyl-1,4-dihydroquinoxaline, 5,7-difluoro-2,3-dicarbamoyl-1,4-dihydroquinoxaline, and 5,6,7-trichloro-2,3-dicarbamoyl-1,4-dihydroquinoxaline.

With respect to Formula XLV, particularly preferred compounds are 5,10-dihydro-1,4-dihydroxypyridazino[4,5-b]quinoxaline, 7,8-dichloro-6-nitro-5,10-dihydro-1,4-dihydroxypyridazino[4,5-b]quinoxaline, 7,8-dibromo-6-nitro-5,10-dihydro-1,4-dihydroxypyridazino[4,5-b]quinoxaline, 7,8-difluoro-6-nitro-5,10-dihydro-1,4-dihydroxypyridazino[4,5-b]quinoxaline, 7,8-dimethyl-6-nitro-5,10-dihydro-1,4-dihydroxypyridazino[4,5-b]quinoxaline, 6,8-bis(trifluoromethyl)-5,10-dihydro-1,4-dihydroxypyridazino[4,5-b]quinoxaline, 6,8-dimethyl-5,10-dihydro-1,4-dihydroxypyridazino[4,5-b]quinoxaline, 6,8 -dichloro-5,10-dihydro-1,4-dihydroxypyridazino[4,5-b]quinoxaline, 6,8-difluoro-5,10-dihydro-1,4-dihydroxypyridazino[4,5-b]quinoxaline, and 6,7,8-trichloro-5,10-dihydro-1,4-dihydroxypyridazino[4,5-b ]quinoxaline.

With respect to Formula XLVI, particularly preferred compounds are 3,8-dihydrocyclobuta[b ]quinoxaline-1,2-dione, 5,6-dichloro-4-nitro-3,8-dihydrocyclobuta[b]quinoxaline-1,2-dione, 5,6-dibromo-4-nitro-3,8-dihydrocyclobuta[b]quinoxaline-1,2-dione, 5,6-difluoro-4-nitro-3,8-dihydrocyclobuta[b]quinoxaline-1,2-dione, 5,6-dimethyl-4-nitro-3,8-dihydrocyclobuta[b]quinoxaline-1,2-dione, 4,6-bis(trifluoromethyl)-3,8-dihydrocyclobuta[b]quinoxaline-1,2-dione, 4,6-dimethyl-3,8-dihydrocyclobuta[b]quinoxaline-1,2-dione, 4,6-dichloro-3,8-dihydrocyclobuta[b]quinoxaline-1,2-dione, 4,6-difluoro-3,8-dihydrocyclobuta[b]quinoxaline-1,2-dione, and 4,5,6-trichloro-3,8-dihydrocyclobuta[b]quinoxaline-1,2-dione.

With respect to Formula XLVII, particularly preferred compounds are 5,10,5a, 10a-tetrahydro-1,4-dihydroxypyridazino[4,5-b]quinoxaline, 7,8-dichloro-6-nitro-5,10,5a,10a-tetrahydro-1,4-dihydroxypyridazino[4,5-b]quinoxaline, 7,8-dibromo-6-nitro-5,10,5a,10a-tetrahydro-1,4-dihydroxypyridazino[4,5-b]quinoxaline, 7,8-difluoro-6-nitro-5,10,5a, 10a-tetrahydro-1,4-dihydroxypyridazino[4,5-b]quinoxaline, 7,8-dimethyl-6-nitro-5,10,5a, 10a-tetrahydro-1,4-dihydroxypyridazino[4,5-b]quinoxaline, 6,8-bis(trifluoromethyl)-5,10,5a, 10a-tetrahydro-1,4-dihydroxypyridazino[4,5b]quinoxaline, 6,8-dimethyl-5,10,5a,10a-tetrahydro-1,4-dihydroxypyridazino[4,5-b]quinoxaline, 6,8-dichloro-5,10,5a, 10a-tetrahydro-1,4-dihydroxypyridazino[4,5-b]quinoxaline, 6,8-difluoro-5,10,5a,10a-tetrahydro-1,4-dihydroxypyridazino[4,5-b]quinoxaline, and 6,7,8-trichloro-5,10,5a, 10a-tetrahydro-1,4-dihydroxypyridazino[4,5-b]quinoxaline.

With respect to Formula XLVIII, particularly preferred compounds are 2-hydroxybenzimidazole, 5,6-dichloro-4-nitro-2-hydroxybenzimidazole, 5,6-dibromo-4-nitro-2-hydroxybenzimidazole, 5,6-difluoro-4-nitro-2-hydroxybenzimidazole, 5,6-dimethyl-4-nitro-2-hydroxybenzimidazole, 4,6-bis(trifluoromethyl)-2-hydroxybenzimidazole, 4,6-dimethyl-2-hydroxybenzimidazole, 4,6-dichloro-2-hydroxybenzimidazole, 4,6-difluoro-2-hydroxybenzimidazole, and 4,5,6-trichloro-2-hydroxybenzimidazole.

With respect to Formula XLIX, particularly preferred compounds are 3-(hydroxyimino)-1,4-dihydroquinoxaline-2-one, 6,7-dichloro-5-nitro-3-(hydroxyimino)-1,4-dihydroquinoxaline-2-one, 6,7-dibromo-5-nitro-3-(hydroxyimino)-1,4-dihydroquinoxaline-2-one, 6,7-difluoro-5-nitro-3-(hydroxyimino)-1,4-dihydroquinoxaline-2-one, 6,7-dimethyl-5-nitro-3-(hydroxyimino)-1,4-dihydroquinoxaline-2-one, 5,7-bis(trifluoromethyl)-3-(hydroxyimino)-1,4-dihydroquinoxaline-2-one, 5,7-dimethyl-3-(hydroxyimino)-1,4-dihydroquinoxaline-2-one, 5,7-dichloro-3-(hydroxyimino)-1,4-dihydroquinoxaline-2-one, 5,7-difluoro-3-(hydroxyimino)-1,4-dihydroquinoxaline-2-one, and 5,6,7-trichloro-3-(hydroxyimino)-1,4-dihydroquinoxaline-2-one.

In general, the compounds which are used for treating animals should not have $R_2$ or $R_4$=fluorine and $R_1$=an electron withdrawing group such as nitro, as such compounds are expected to be unstable. It is expected that fluorine in these positions will be readily displaced in such compounds by common biological nucleophiles.

The compounds of the present invention, especially those substituted with non-ionic groups, are expected to be highly lipophilic and able to easily cross the blood brain barrier. Thus, these compounds are expected to be particularly useful for treating or preventing conditions involving the central nervous system. These compounds are also expected to be potent anticonvulsants in animal models and will prevent ischemia-induced nerve cell death in the gerbil global ischemia model after i.p. and i.v. administration.

The compounds of the present invention are active in treating or preventing neuronal loss, neurodegenerative diseases, chronic pain, are active as anticonvulsants and inducing anesthesia. Certain of the compounds of the present invention are expected to exhibit little or no untoward side effects caused by non-selective binding with other receptors, particularly, the PCP and glutamate receptors associated with the NMDA receptor. In addition, certain of the compounds block kainate, AMPA and quisqualate receptors and are therefore useful as broad-spectrum excitatory amino acid receptor antagonists. Moreover, the compounds of the present invention are effective in treating or preventing the adverse consequences of the hyperactivity of the excitatory amino acids, e.g., those which are involved in the NMDA receptor system, by blocking the glycine receptors and preventing the ligand-gated cation channels from opening and allowing excessive influx of $Ca^{++}$ into neurons, as occurs during ischemia.

Neurodegenerative diseases which may be treated with the compounds of the present invention include those selected from the group consisting of Alzheimer's disease, amyotrophic lateral sclerosis, Huntington's disease and Down's syndrome.

The compounds of the present invention find particular utility in the treatment or prevention of neuronal loss associated with multiple strokes which give rise to dementia. After a patient has been diagnosed as suffering from a stroke, the compounds of the present invention may be administered to ameliorate the immediate ischemia and prevent further neuronal damage that may occur from recurrent strokes.

The compounds of the invention find particular utility in treating or preventing the adverse neurological consequences of surgery. For example, coronary bypass surgery requires the use of heart-lung machines which tend to introduce air bubbles into the circulatory system which may lodge in the brain. The presence of such air bubbles robs neuronal tissue of oxygen, resulting in anoxia and ischemia. Pre- or post- surgical administration of the compounds of the present invention will treat or prevent the resulting ischemia. In a preferred embodiment, the compounds of the invention are administered to patients undergoing cardiopulmonary bypass surgery or carotid endarterectomy surgery.

The compounds of the present invention also find utility in treating or preventing chronic pain. Such chronic pain may be the result of surgery, trauma, headache, arthritis, or other degenerative disease. The compounds of the present invention also find particular utility in the treatment of phantom pain that results from amputation of an extremity. In addition to treatment of pain, the compounds of the invention are also expected to be useful in inducing anesthesia, either general or local anesthesia, for example, during surgery.

The glycine and excitatory amino acid antagonists may be tested for in vivo anticonvulsant activity after intraperitoneal injection using a number of anticonvulsant tests in mice (audiogenic seizure model in DBA-2 mice, pentylenetetrazol-induced seizures in mice, NMDA-induced death and maximum electroshock-induced seizure (MES)). The compounds may also be tested in drug discrimination tests in rats trained to discriminate PCP from saline. It is expected that none of the compounds will produce a behavioral excitation in locomotor activity tests in the mouse. It is expected that such results will suggest that the glycine, AMPA, kainate and quisqualate antagonists of the present invention do not show the PCP-like behavioral side effects that are common to NMDA channel blockers such as MK-801 and PCP or to competitive NMDA antagonists such as CGS19755.

The glycine and excitatory amino acid antagonists are also expected to show potent activity in vivo after intraperitoneal injection suggesting that these compounds can penetrate the blood/brain barrier.

The compounds of the present invention may be tested for potential glycine antagonist activity by observing the inhibition of binding of 1 µM glycine-stimulated [$^3$H]-MK-801 in rat or guinea pig brain membrane homogenates. The more potent the glycine antagonist, the less [$^3$H]-MK-801 can bind since the [$^3$H]-MK801 binding site (PCP receptor) is accessible only upon opening of the ion channel by glutamate and glycine (Fletcher, E. L., et al., in *Glycine Neurotransmission*, Otterson, P., et al. (eds.), John Wiley and Sons (1990); Johnson, J. W., et al., *Nature* 325:529 (1987)).

The binding affinities of quinoxaline-2,3-diones at NMDA receptor glycine sites also were estimated by electrophysiological assay either using cloned rat NMDA receptors expressed in Xenopus oocytes, or non-NMDA receptors expressed in oocytes by whole rat brain poly(A)$^+$RNA. $K_b$ values were estimated by assuming competitive inhibition and assaying suppression of membrane current responses elicited by fixed concentrations of agonist: 1 mM glycine and 100 mM glutamate for NMDA receptors; 20 mM kainic acid for non-NMDA receptors. For NMDA receptors $K_b$S were approximated by averaging values at three subtype combinations (NR1A/NR2A, NR1A/NR2B, and NR1A/NR2C).

The 1,4-benzoxazine-2,3-diones having Formula IV may be prepared according to U.S. Pat. No. 4,307,091, which teaches that these compounds are anti-allergic agents. 1,4-Benzoxazine-2,3-dione 2 was prepared by condensation of 2-aminophenol with oxalyl chloride (eq 1) (See Loev et al., *J. Med. Chem* 28:24–27 (1985)). This compound has a $IC_{50}$ value of 167 μm, which is a potency of 1.5% of DCK. This value is similar to the unsubstituted 1,4-dihydroquinoxaline-2,3-dione (QX), which has a potency of 2% of DCK, suggesting that one of the NH groups is not essential for the binding of QX to glycine/NMDA receptor. Therefore substituted 1,4-benzoxazine-2,3-diones are a promising series of compounds as antagonists for the glycine/NMDA receptor similar to the QX series. However, when an attempt was made to prepare Cl and $NO_2$ substituted compounds such as 2b–2d, a mixture of 2b–2d with 3b–3d was obtained due to the sensitivity of 2b–2d toward hydrolysis. (Reissenweber, G., Mangold, D., *Angew. Chem. Int. Ed. Engl.* 19:22–223 (1980).) Derivatives of substituted 1,4-benoxazine-2,3-diones with nonelectron withdrawing groups such as methyl are expected to be less sensitive unless $R_1$=nitro.

Another approach for the preparation of 2 is through oxidation of isatin 4 (eq 2). (See, Mohiuddin, G. et al., *Ind. J. Chem.* 24B:905–907 (1985), Movrin et al., *Acta Pharm. Jugosl.* 35:193–202 (1985), German Patent Application No. 2,944,696 Al.) 4,6-Dichlorisatin was oxidized to give 5,7-dichloro-1,4-benzoxazine-2,3-dione 2e without any contamination of the hydrolytic product 3d. Therefore this is a more promising approach for the preparation of compounds having Formula IV.

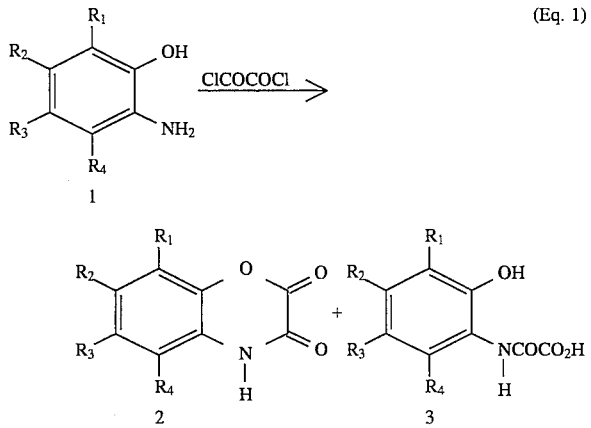

a, $R_1 = R_2 = R_3 = R_4 = H$
b, $R_2 = NO_2$, $R_1 = R_3 = R_4 = H$
c, $R_3 = NO_2$, $R_2 = Cl$, $R_1 = R_4 = H$
d, $R_1 = R_3 = Cl$, $R_2 = R_3 = H$

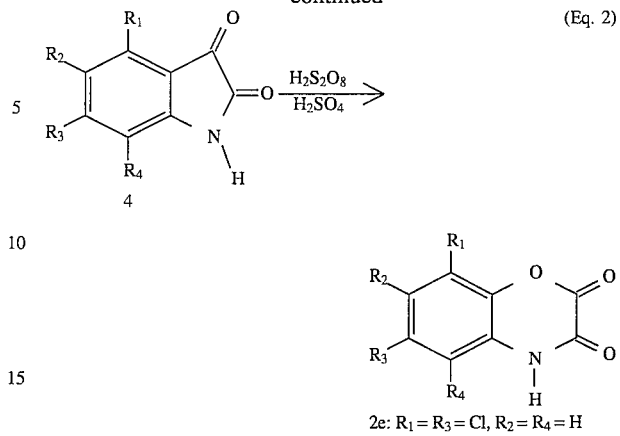

2e: $R_1 = R_3 = Cl$, $R_2 = R_4 = H$

The corresponding 1,4-benzodioxanes may be prepared according to Schmidt and Schuster, *J. Org. Chem.* 43:1823–1824 (1978), by addition of oxalyl chloride to the corresponding substituted catechol in ether and triethyl amine.

Compounds having Formula V may be prepared according to Taniguchi and Satomura, *Agr. Biol. Chem.* 36:2169–2175 (1972); Greibrokk and Undheim, *Acta Chem. Scand.* 25:2935 (1971); and Johnsen and Undheim, *Acta. Chem. Scand. ser B* b38:109–112 (1984). 2,3-Dihydroxyquinoline 5a was prepared by ring expansion of isatin with diazomethane followed by hydrolysis (eq 3) of the intermediate methyl ether 5. Compound 5a has a $IC_{50}$ of 185 μm with a potency of 1.4% of DCK, further supporting the notion that replacement of one of the NH groups in QX with other groups has little effect in the binding of the molecule to the glycine/NMDA receptor. Therefore compounds having Formula V are a promising series of compounds which are antagonists for the glycine/NMDA receptor.

The corresponding methyl ether of 5 was found to be inactive in the in vitro binding assay, implying the importance of the 3-hydroxy group in the binding of the molecule to glycine/NMDA receptor. However, such alkyl ethers may serve as lipophilic pro-drugs which easily cross the blood-brain barrier and are hydrolysed to give the active compound in the brain.

The monofluoro substituted compound 5b is found to be about as active as 5a.

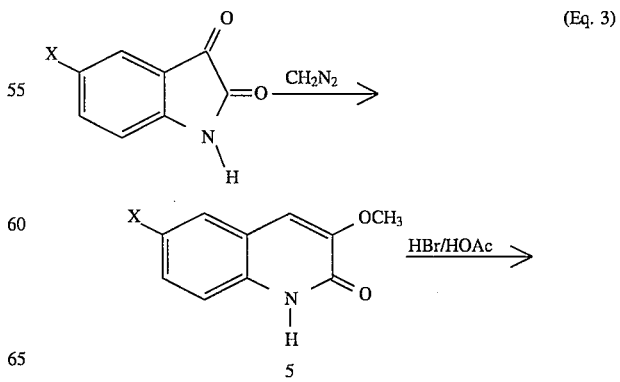

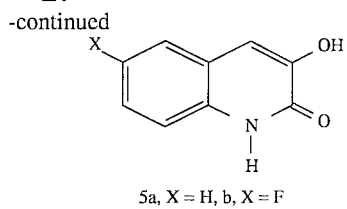

5a, X = H, b, X = F

Compounds having Formula VI may be prepared as follows. Nitration of 5a was expected to give 6a (eq 4). A precipitate was obtained after addition of water to the reaction mixture. $^1$H NMR spectrum suggested that it is the dinitro compound 6b.

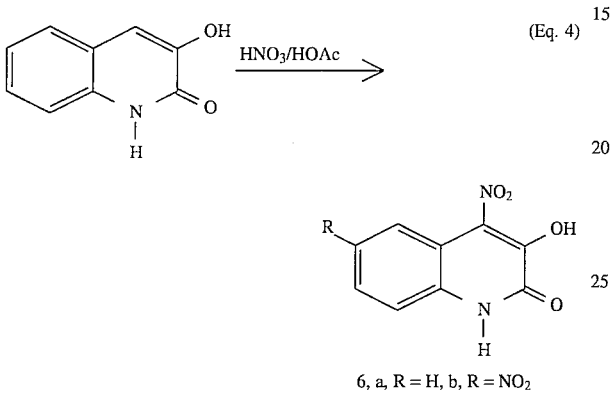

6, a, R = H, b, R = NO$_2$

Nitration under mild conditions with one equivalent of HNO$_3$ should give 6a.

Compounds having Formula VII, may be prepared according to Dahn and Donzel, *Helv. Chim. Acta* 50:1911–1917 (1967), as follows. The corresponding 3-oximequinoline-2,4-dione may be hydrogenated to give IX. For example, 2,3,4-trihydroxyquinoline 11 may be prepared by hydrogenation (Pd/H$_2$) of 3-oxime-quinoline-2,4-dione 10 (eq 10). Compound 11 was found to have IC$_{50}$ value of 60 μM with a potency of 4% of DCK.

Compounds having Formula VIII may be prepared according to Dahn and Donzel, *Helv. Chim. Acta* 50:1911–1917 (1967), as follows. The corresponding 1,2-dihydro-3,4-dihydroxyquinolin-2-one having Formula VII may be oxidized with hydrogen periodate to give VIII. For example, oxidation (KIO$_3$/H$_2$SO$_4$) of 11a (R$_1$–R$_4$=H) produces quinoline-2,3,4-trione 12 (eq 19). Compound 12 was found to have an IC$_{50}$ value of 50 μM with a potency of 5% of DCK.

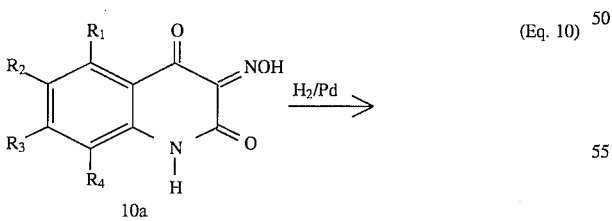

10a

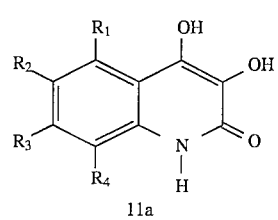

11a

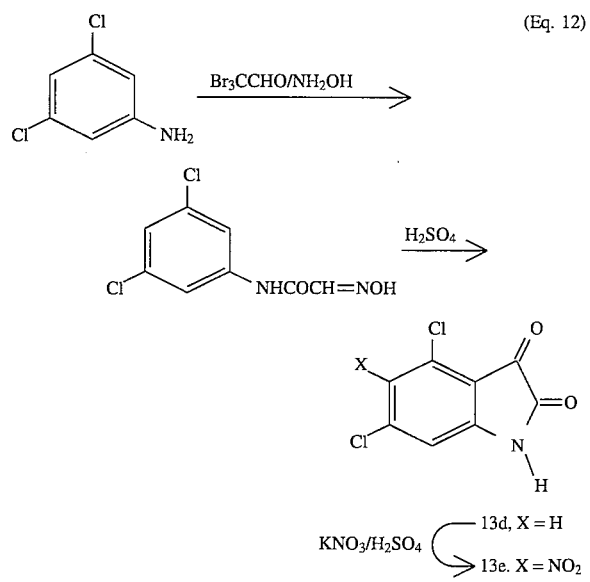

Compounds having Formula IX may be prepared according to Dahn and Donzel, *Helv. Chim. Acta* 50:1911–1917 (1967), as follows. The corresponding substituted 1,2,3,4-tetrahydroquinoline-2,3,4-trione having Formula VIII is treated with first aqueous alkali and then acid to give IX. Alternatively, 4,6-dichloroisatin 13d may be prepared by reaction of 3,5-dichloroaniline with Br$_3$CCHO and NH$_2$OH followed by cyclization in H$_2$SO$_4$ (eq 12). See, Stefanescu, *Rev. Chim. (Bucharest)* 20:353–355 (1969). Nitration of 13d gave a single mono-nitro product. Isatin 13, mono Br, F, NO$_2$ isatin 13a-c and dichloroisatin 13d were all found not to be active as antagonists for the glycine/NMDA receptor. 4,6-Dichloro-5-nitroisatin 13e has a IC$_{50}$ value of 96.5 μm with a potency of 3% of DCK.

Compounds having Formula X may be prepared according to Movrin et al., *Acta Pharm. Jugosl.* 35:193–202 (1985). 6-Bromoisatoic anhydride 14b, 5,7-dichloroisatoic anhydride 14c and 5,7-dichloro-6-nitroisatoic anhydride 14d were prepared by oxidation of the corresponding isatin with H$_2$O$_2$ under acidic conditions (eq 13). lsatoic anhydride 14a has an IC$_{50}$ value of 231 μm with a potency of 1.1% of DCK, which is comparable with that of QX. However, all the substituted isatoic anhydrides, from monosubstituted to trisubstituted, showed potency of only as high as 2.7% (for 14d). It is possible that with more electron withdrawing groups substituted in the benzene portion of the molecules, the anhydrides become more sensitive towards hydrolysis.

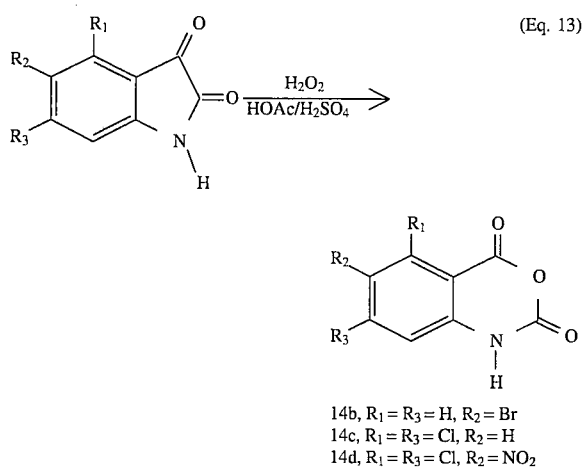

(Eq. 13)

14b, $R_1 = R_3 = H$, $R_2 = Br$
14c, $R_1 = R_3 = Cl$, $R_2 = H$
14d, $R_1 = R_3 = Cl$, $R_2 = NO_2$

Compounds having Formula XI may be prepared by oxidation of the corresponding 2-aminoquinoline 15, which can be prepared as shown in eq. 14.

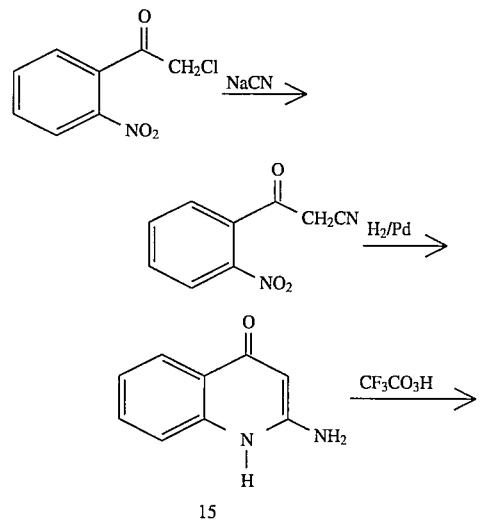

(14)

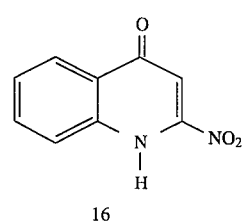

16

See, for example, Keana and Cai, *J. Org. Chem.* 55:3640 (1990).

Alternatively, compound 18 could be prepared by reaction of 2-chloroquinoline with $AgNO_2$, as shown in eq. 15.

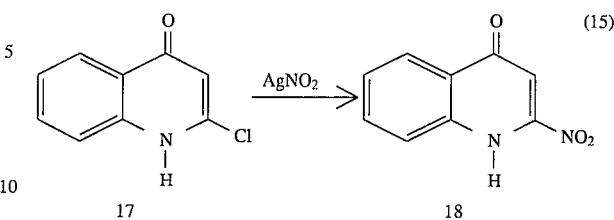

(15)

See, Iijima, *Yakugaka Zasshi* 109:18 (1989).

Compounds related to 19 may be prepared according to U.S. Pat. No. 3,816,470 (1974), which reports that these compounds have high vitamin P activity. Compound 19 was found to be only partially active as an antagonist for the glycine/NMDA receptor. Therefore the NH group in kynurenic acid 20 appears to be essential for the binding of the molecule to the glycine/NMDA receptor.

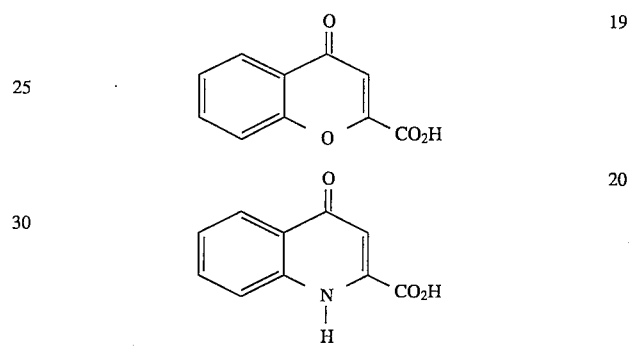

Compounds having Formula XII may be prepared by cyclization of isocyanate 21 with amine $NH_2R$ as shown in eq. 16.

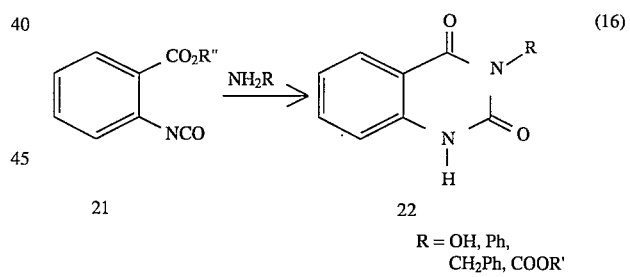

(16)

R = OH, Ph,
CH$_2$Ph, COOR'

Alternatively, they may be prepared by reaction of anthranilate with isocyanate as shown in eq. 17.

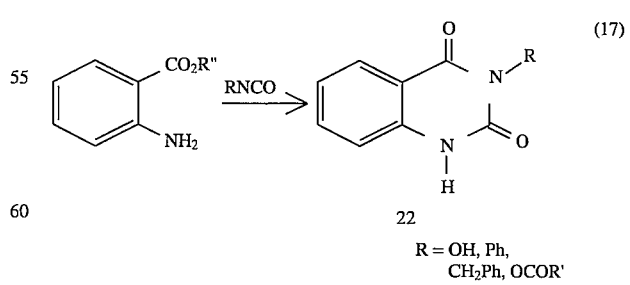

(17)

R = OH, Ph,
CH$_2$Ph, OCOR'

Substituents may be added by an electrophilic substitution reaction as follows:

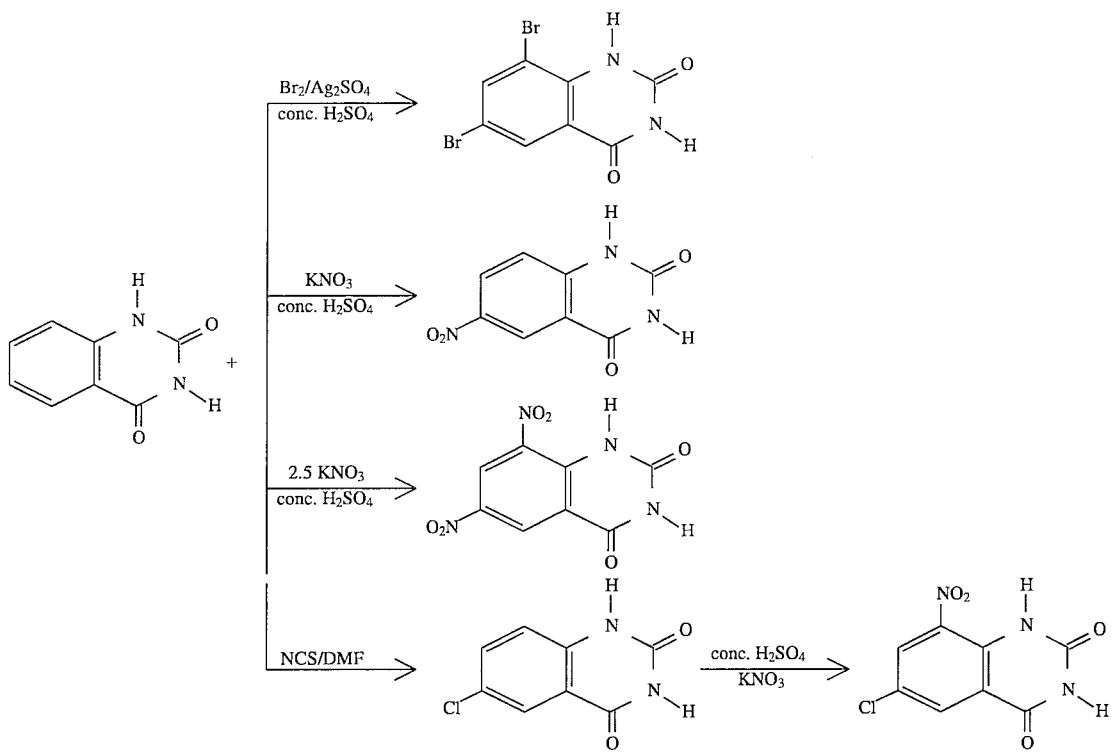

Compounds having Formula XX may be prepared as follows. The amine obtained by reduction of the nitro group in 23 may be added to the alkyne to produce 24 (eq. 18).

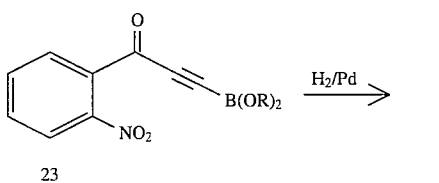

(R = i-Pr or H).

Compound 23 can be prepared as shown in eq. 19 or eq. 20.

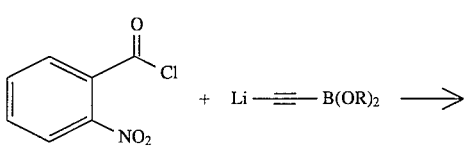

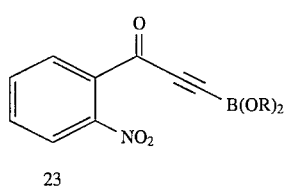

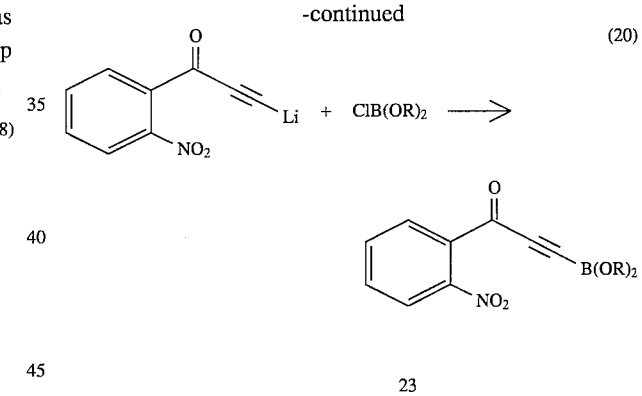

Compounds having Formula XXI may be prepared by cyclization of 2-aminophenylboronic acid with isocyanate (eq. 21) to give 25, or as shown for the preparation of compounds 25a and 25b (eqs. 22–23).

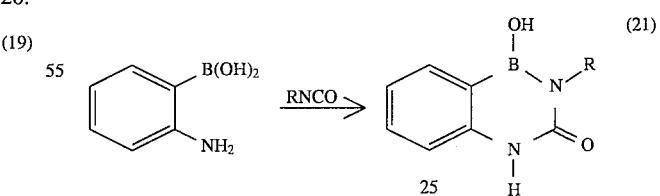

R = H, Me, Ph, CH₂Ph

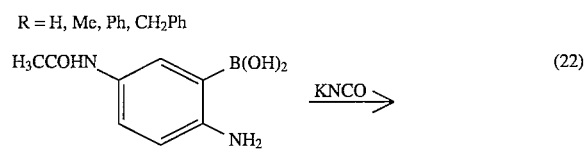

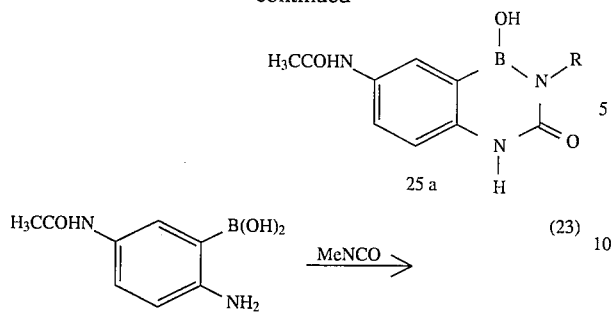

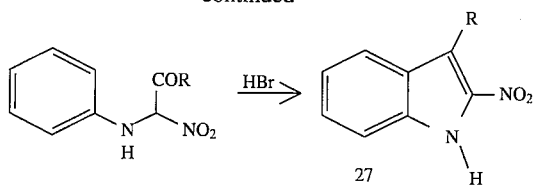

R = CH$_2$NO$_2$, R = CH$_2$COR'
R' = NH$_2$, OMe, OH.

Compounds having Formula XXIV and other related compounds may be prepared following the method of Bischler synthesis of indoles as shown in eq. 27.

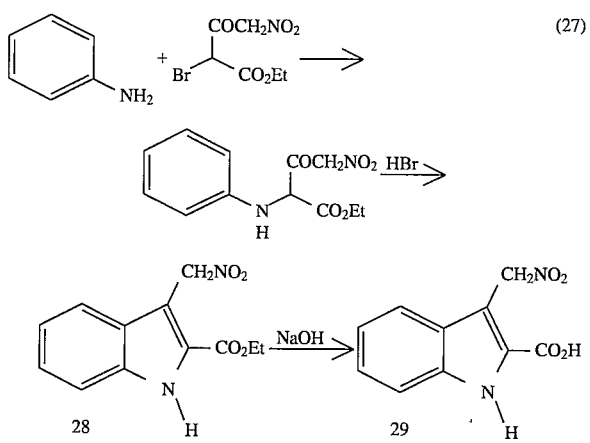

(27)

The starting materials may be prepared as shown in eq. 28.

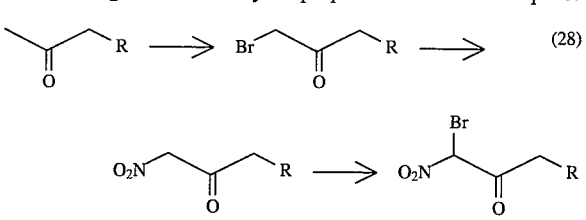

(28)

R = NO$_2$, CONH$_2$, CO$_2$Et

Related compounds having Formula XV may be prepared as shown in eq. 29.

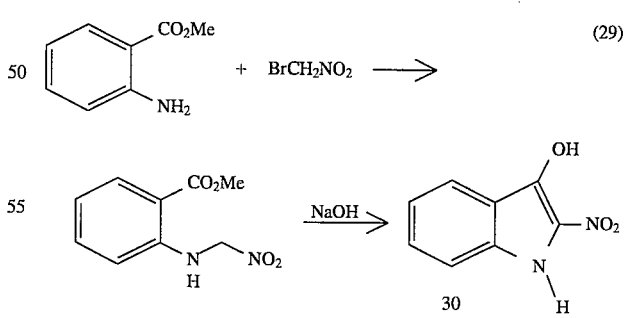

(29)

Compounds having Formula XIV may be prepared as shown in eq. 30 according to (*J. Med. Chem.* 36:2459 (1993)).

See, Cai, S. X.; Keana, J. F. W. "Synthesis, Structure and Properties of New Boron-Containing Heterocycles," 13th International Congress of Heterocyclic Chemistry, Corvallis, Oreg., August 1991.

Compounds having Formula XXII may be prepared by cyclization of 2-aminophenylboronic acid with N,N-disubstituted carbamyl chloride (eq 24) to give 26, such as shown for the preparation of compound 26a (eq. 25).

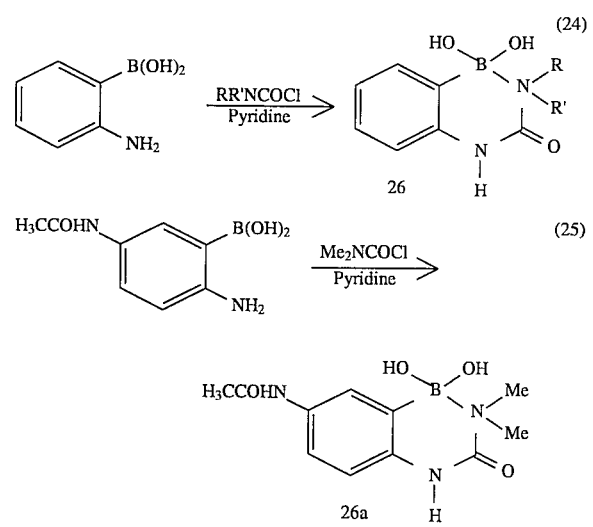

See, Soloway, A. H., *J. Am. Chem. Soc.* 82:2442 (1960) and Dewar, M. J. S., *Advances in Chemistry Series, No. 42*, Niedenzu, K. Ed. American Chemical Society, Washington, D.C. p 241. (1964).

Compounds having Formulae XIV, XXIII and XXV and other related compounds may be prepared following the method of Bischler synthesis for indoles (Paquette, L. Principles of Modern Heterocyclic Chemistry, W. A. Benjamin, Inc., New York, 1968, pp 159–160) as shown in eq. 26.

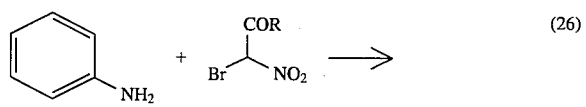

(26)

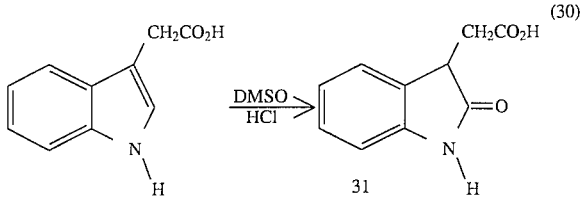
(30)

Compounds having Formula XLVIII may be prepared as shown in eq. 31 for compound 58a.

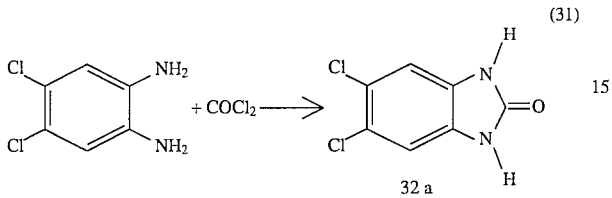
(31)

Compounds having Formula XXVII may be prepared by condensation of ethyl 2-bromo-2-nitroacetate with 1,2-diaminobenzenes. For example, condensation of ethyl 2-bromo-2-nitroacetate with 4,5-dichloro-1,2-diaminobenzene gave 33. It was found by $^1$H NMR that 33 is present in the enol form 33a in DMSO-$d_6$. Compound 33 was found to have a Ki value of 0.22 μm, which is similar to the corresponding 6,7-dichloroquinoxaline-2,3-dione.

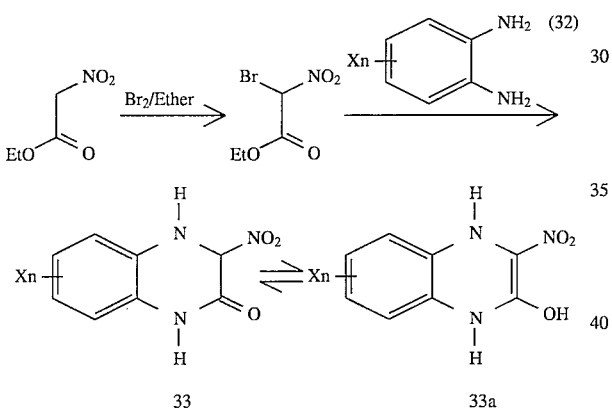
(32)

Xn = 6,7-Cl$_2$

Compounds having Formula XXVI may be prepared by oxidation of the corresponding compound 33.

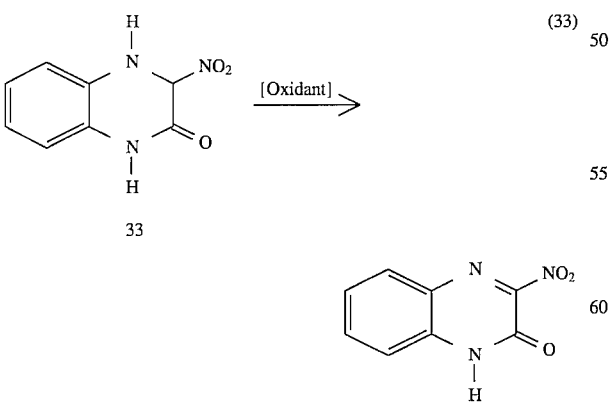
(33)

Examples of such oxidants include SeO$_2$.

Alternatively, they may be prepared by oxidation of the corresponding amine 35.

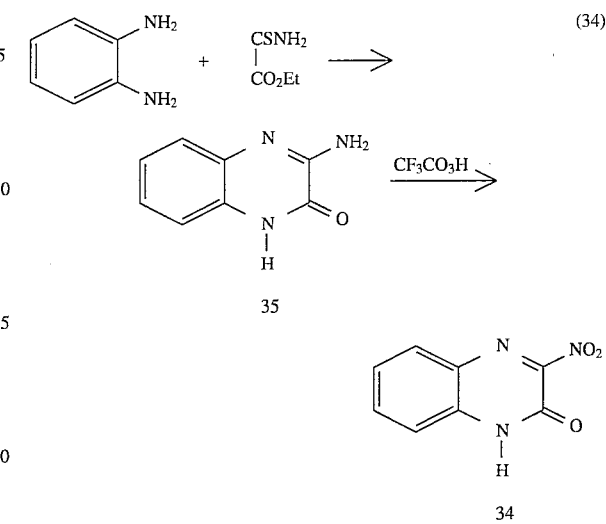
(34)

See, Keana & Cai, *J. Org. Chem.* 55:3640 (1990) and Burrell et al., *J. Chem. Soc. Perkin I.* 2707 (1973).

Related compounds having Formula XLIX may be prepared by replacing the amino group in 35 with hydroxylamine. For example, 3-amino-6,7-dichloroquinoxaline-3-one (36) was reacted with hydroxylamine to give 6,7-dichloro-3-oximequinoxaline-2-one 37 (eq. 35). Compound 37 was found to have a Ki value of 0.3 μM, which is similar to the corresponding 6,7-dichloroquinoxaline-2,3-dione.

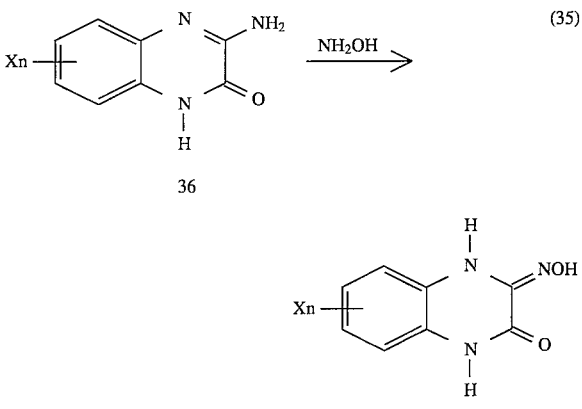
(35)

Xn = 6,7-Cl$_2$

Alternatively, compounds having Formula XLIX may be prepared by reduction of 3-nitro compounds 38.

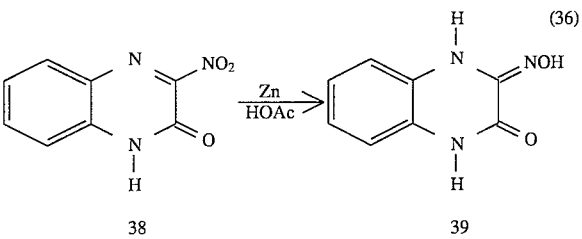
(36)

Another related compound having Formula XIII may be prepared by condensation of a 1,2-diaminobenzene with benzoylformic acid (eq. 37).

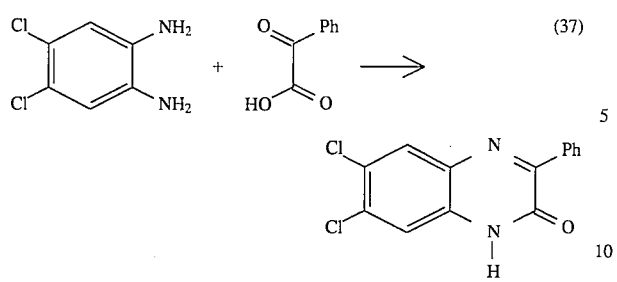

(37)

Compounds having Formula XVI may be prepared by nitrosation of the corresponding benzazepine 40 to give 41.

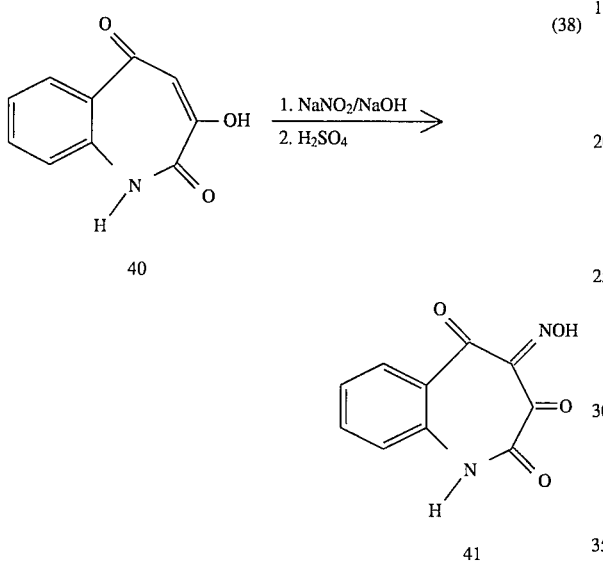

(38)

Compounds having Formula XXVIII may be prepared by reaction of sodium azide and sulfuric acid with 1,4-naphthoquinone according to Jones, G., *J. Chem. Soc.* 1808 (1967) and Rickards and Smith, *Tet. Lett.* 22:2361 (1966). See also, U.S. Pat. No. 4,477,446, which teaches that these compounds are useful as anti-allergic agents; European Application 130,538, published Jan. 9, 1985; Eicher and Kruse, *Synthesis No.* 6–7:612–619 (1985). For example, benzazepine-2,5-dione 42, may be prepared by ring expansion of naphthaquinone with $NaN_3$ in concentrated $H_2SO_4$ (eq 39). The product isolated from the reaction mixture is mainly 42 (about 80%) contaminated with unknown impurities. When excess $NaN_3$ (2 times) was used in the reaction, a product was isolated which was identified to be 43 by NMR and MS (eq 40). Compound 43 was found to be inactive as an antagonist for the glycine/NMDA receptor.

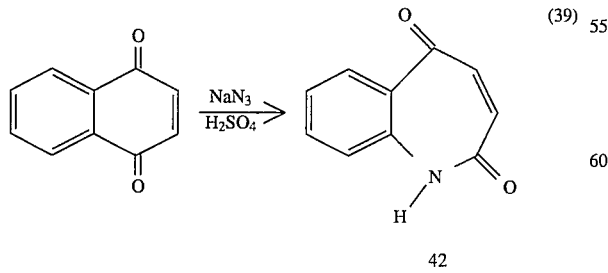

(39)

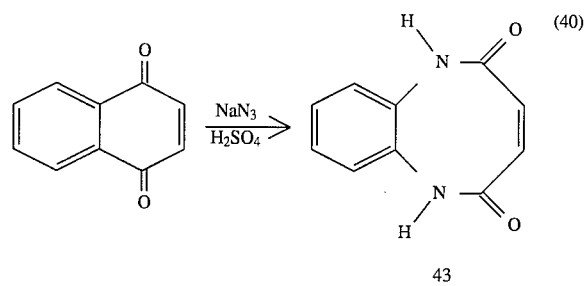

(40)

Compounds having Formula XVII may be prepared by nitration of the corresponding benzazepine 44 to give 45.

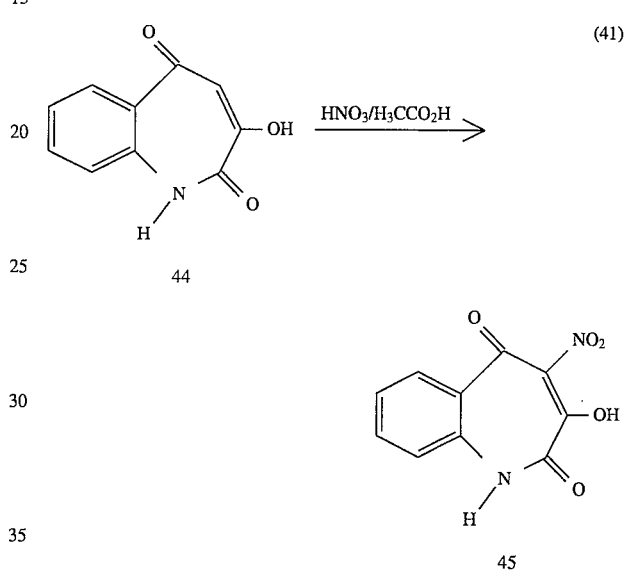

(41)

See, Buckle et al., *J. Med. Chem.* 18:726 (1975) who disclose the nitration of a structurally related 6-member ring compound.

Related compounds having Formulae XVIII and XIX may be prepared by nitrosation and nitration of the corresponding benzazepine to give 46 and 47, respectively.

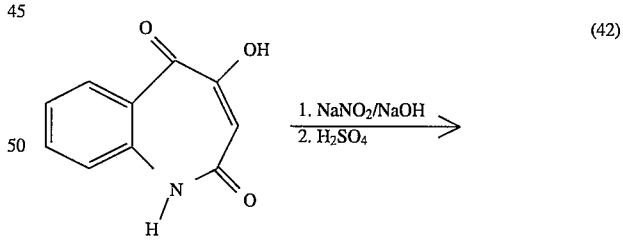

(42)

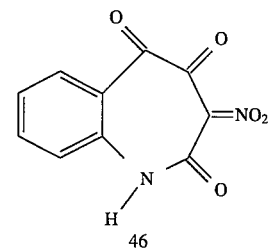

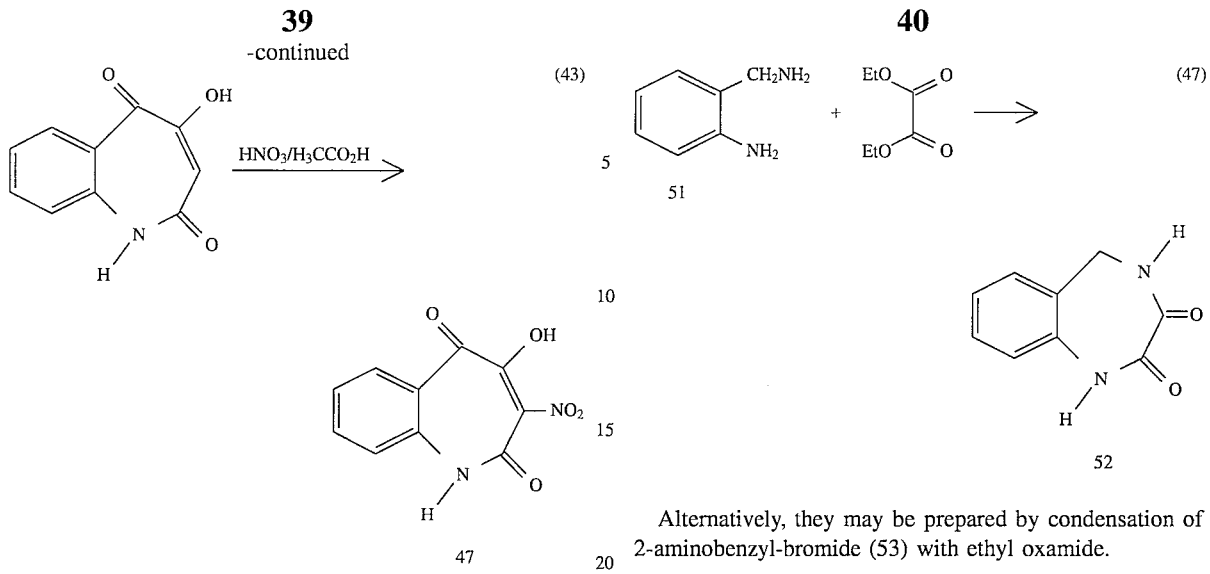

See, Buckle et al., *J. Med. Chem.* 20:1059 (1977).

Alternatively, compounds with Formula XXXII, e.g., compound 48, may be prepared from 2,5-dihydro-1H-benazepine-2,5-dione as reported by Eicher and Kruse, *Synthesis No.* 6–7:612–619 (1985) (eq. 45).

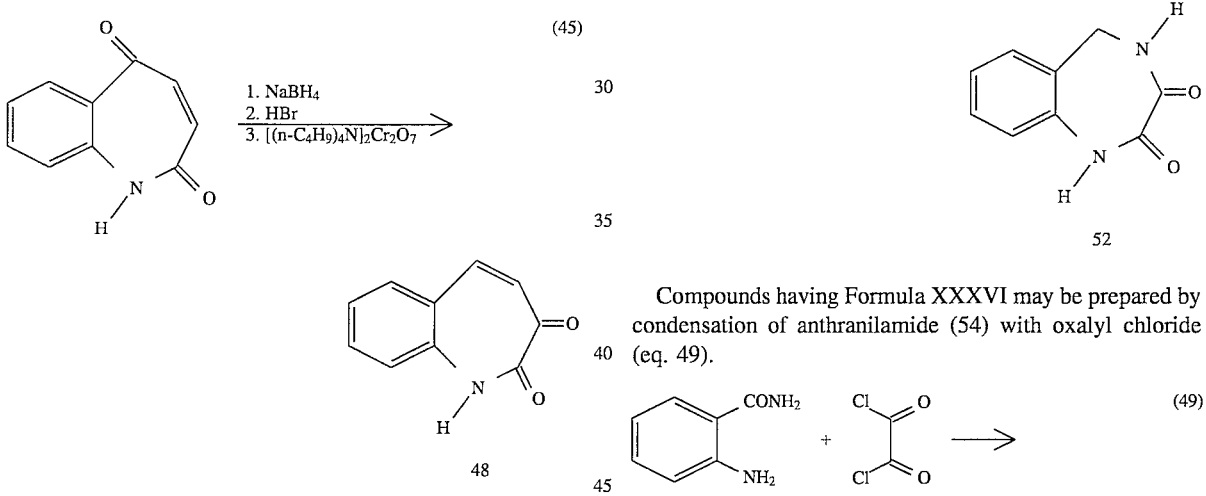

Compounds having Formula XXXIII may be prepared according to U.S. Pat. No. 4,307,091, which teaches that these compounds are useful as anti-allergic agents.

Compounds having Formula XXXIV may be prepared as follows. The corresponding substituted 1,2,3,4-tetrahydro-quinoline-2,3,4-trione (49) may be treated with diazomethane to give the ring expanded product 50 (eq. 46).

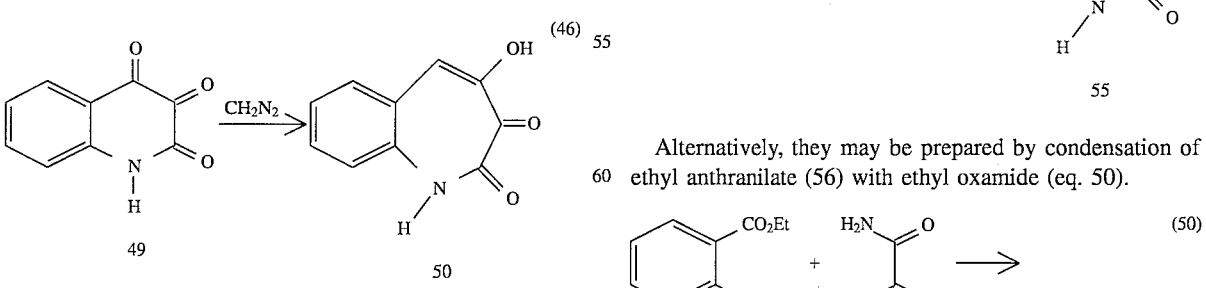

Compounds having Formula XXXV may be prepared by condensation of 2-aminobenzylamine (51) with diethyl oxalate or oxalylchloride (eq. 47) to give 52.

Alternatively, they may be prepared by condensation of 2-aminobenzyl-bromide (53) with ethyl oxamide.

Compounds having Formula XXXVI may be prepared by condensation of anthranilamide (54) with oxalyl chloride (eq. 49).

Alternatively, they may be prepared by condensation of ethyl anthranilate (56) with ethyl oxamide (eq. 50).

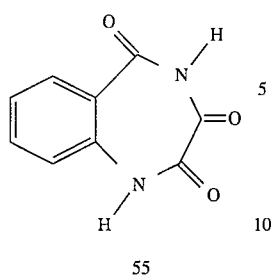

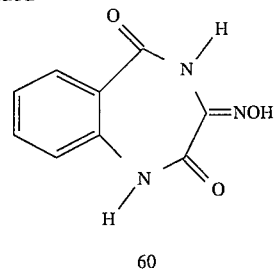

They also may be prepared by oxidation of compound 57.

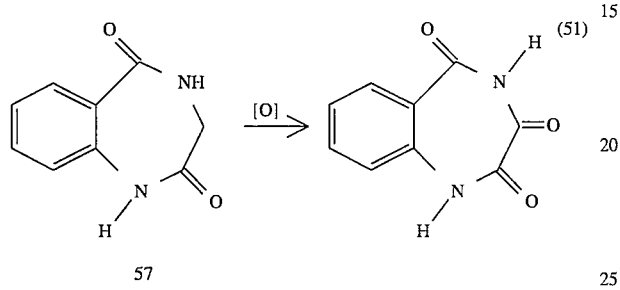

Related compounds having Formula XXX may be prepared as shown in eq. 52.

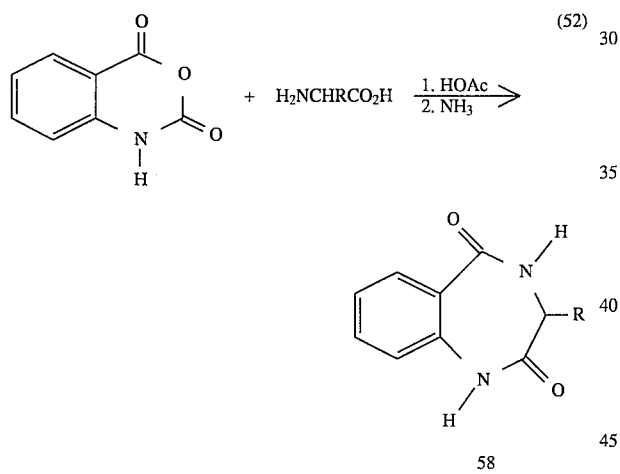

R = Ph, CH$_2$Ph

See, Mohiuddin et al., *Ind. J. Chem.* 24B:905 (1985).

Compounds having Formula XXIX may be prepared by nitrosation of 59 to give 60 (eq. 53).

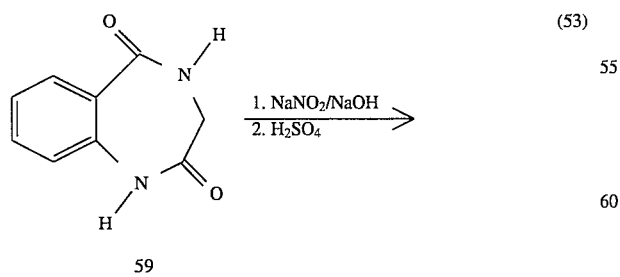

Compounds having Formula XXXI may be prepared, for example, by bromination of 61 in the 3-position followed by displacement with sodium or silver nitrate to give 62 (eq. 54).

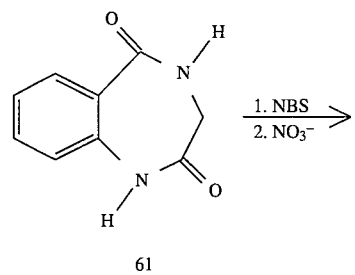

See, Kornblum, N., *Organic Reactions* 12:101–156 (1962).

Compounds having Formula XLIV may be prepared from the diacid 63 (*Ann. Chim* (*Rome*) 51:1102 (1961); Chem. Abst. 57:11194 (1962)) to diamide 64 (eq. 55).

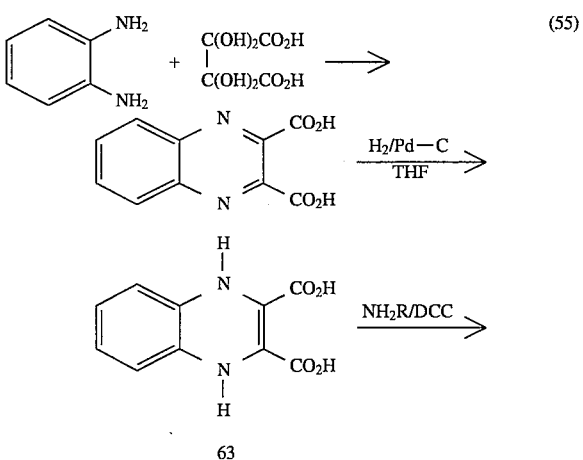

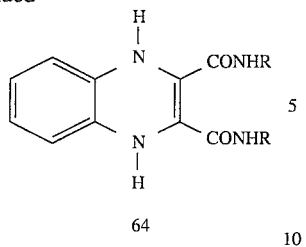

64

R = H, alkyl

Related compounds 65 and 66 (Formula XLIII) may be prepared similarly such as shown in eq. 56.

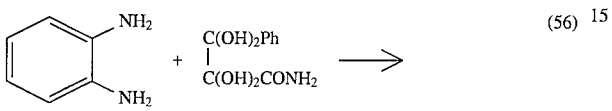  (56)

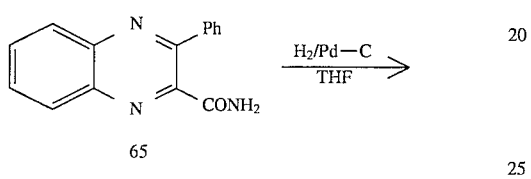

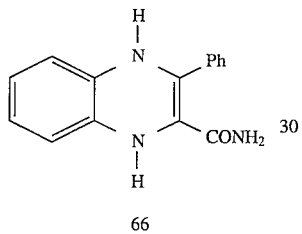

66

Reaction of diacid 67 with hydrazine results in cyclization to give tricyclic compound 68 of Formula XLV (eq. 57).

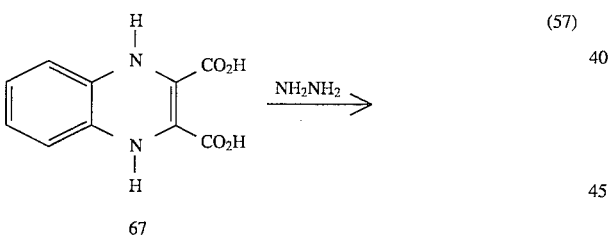  (57)

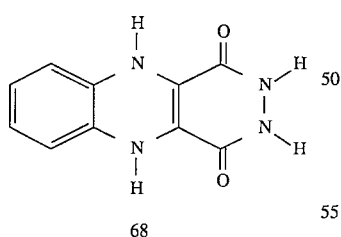

68

Related compounds having Formula XLII (e.g., compound 70) may be prepared by cyclization of the diacid 69 (*Chem. Abst.* 57:5914 (1962)).

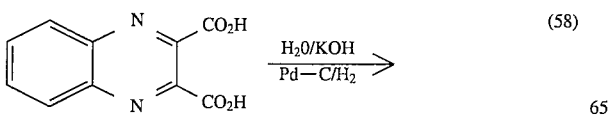  (58)

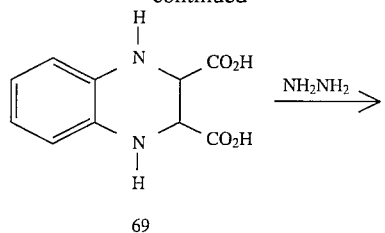

69

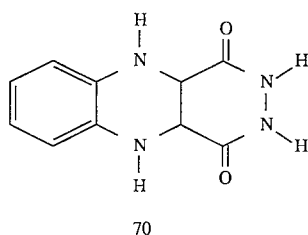

70

Compounds having Formula XLVI may be prepared by cyclization of 1,2-diaminobenzenes with diethyl squarate, such as shown for the synthesis of 71a (eq. 59) according to the methods disclosed by Ehrhardt, et al., *Ber.* 110:2506 (1977):

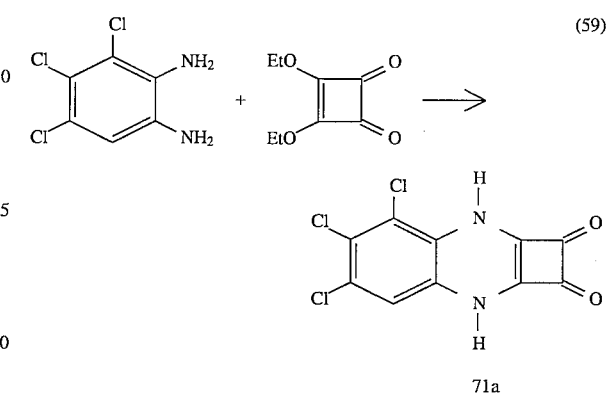  (59)

71a

Ethanol is employed as the solvent and it is distilled from the reaction mixture in an effort to drive the reaction to completion. After purification, crystallization yielded 25% (on average) of the desired products as orange needles. Examples of such compounds have the following formulae:

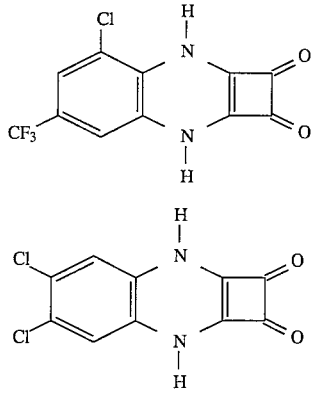

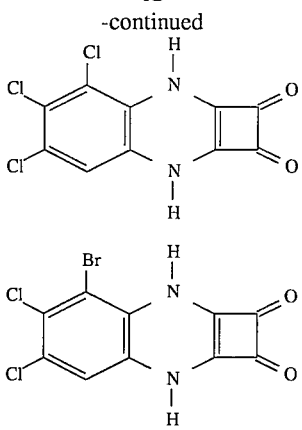

Phenylenediamines which were not commercially available (3-bromo-4,5-dichlorophenylene-1,2-diamine and 3,4,5-trichlorophenylene-1,2-diamine) were prepared from 4,5-dichloro-2-nitroaniline by chlorination or bromination (NCS and NBS, respectively) and reduction of the nitro group with stannous chloride.

Compounds having Formula XXXVII may be prepared according to Takahashi et at., *Nippon Kgaku Kaishi* 8:1259–1263 (1973) from an appropriately substituted isotoic anhydride. See also, Mohiuddin et al., *Ind. J. Chem.* 24B:905–907 (1985); Akssira et al., *Tetrahedron Lett.* 33:1887–1888 (1992). [1,4]-Benzodiazepine-2,5-dione 73a was prepared by reaction of isatoic anhydride (72) with glycine (eq. 60). Compound 73a was found to have an $IC_{50}$ value of 300 μm with a potency of 1.0% of DCK. Therefore preparation of substituted 73 from substituted isatoic anhydride has been explored. 7-Chloro-[1,4]-benzodiazepine-2,5-dione 73b and 6,8-dichloro-[1,4]-benzodiazepine-2,5-dione 73c were prepared from the corresponding isatoic anhydride.

21-130

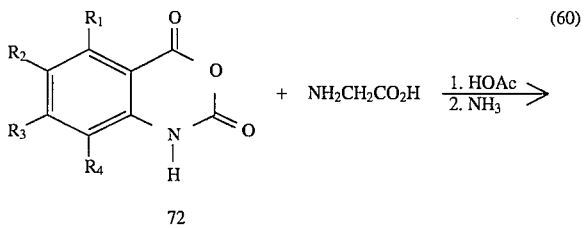

a: $R_1 = R_2 = R_3 = R_4 = H$
b: $R_2 = Cl, R_1 = R_3 = R_4 = H$
c: $R_1 = R_3 = Cl, R_2 = R_4 = H$

Compounds having Formula XXXIX and XL may be prepared as shown in eq 61. Cyclization of 1,2-phenylenediamine with malonic acid gives benzodiazepine 74 (Essassi et al., *Bull. Soc. Chim. Belg.* 100:277 (1991)). Compound 74 was converted to alkene 75 which was oxidized to produce trione 76 (Dolenz and Kollenz, *Chem. Ber.* 115:593 (1982)). Compound 76 was found to be in the hydrate form by $^1H$ NMR spectroscopy.

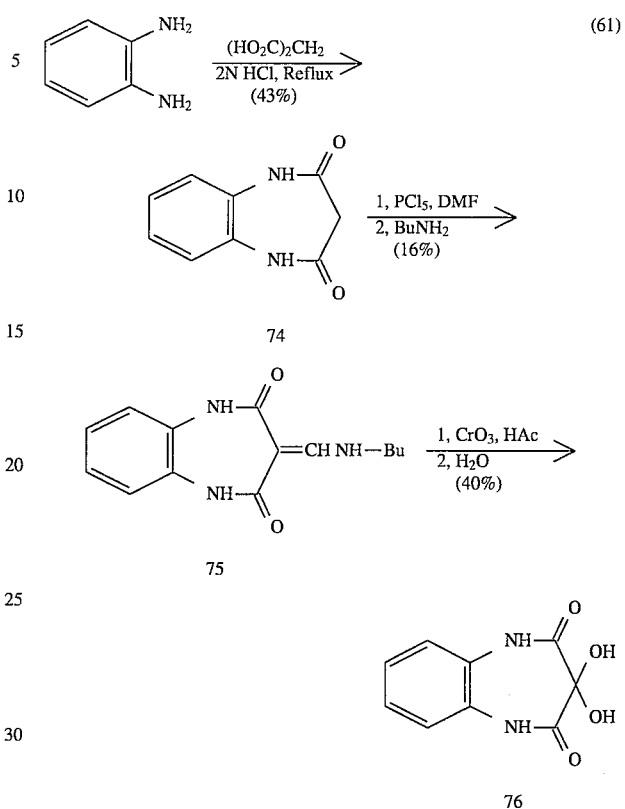

Compounds having Formula XLI may be prepared according to U.K. Patent No. 1,460,936, which reports that these compounds are anti-allergic agents.

Thus, the present invention is directed to compounds having high binding to the glycine receptor and low binding to the kainate and AMPA sites. Particular compounds of the invention may have high antagonist potency at the kainate, AMPA and quisqualate receptors in addition to the glycine receptor. According to the present invention, those compounds having high binding to the glycine receptor exhibit a glycine binding affinity ($K_i$) of about 100 μM or less in a glycine binding assay. Preferably, the compounds of the present invention exhibit a $K_i$ of 10 μM or less. Most preferably, the compounds of the present invention exhibit a $K_i$ of 1 μM or less. The compounds exhibit high binding to the kainate and AMPA sites if they exhibit a $K_i$ of about 10 μM or less, especially, 1 μM or less in a kainate or AMPA binding assay.

The glycine antagonist potency in vitro may be determined using a 1 μM glycine-stimulated $[^3H]$-MK801 binding assay. This assay takes advantage of the fact that the binding of $[^3H]$-MK801 to the PCP receptor inside the pore of the NMDA channel is dependent on the presence of both glutamate and glycine. In the absence of glycine but in the presence of glutamate, $[^3H]$-MK801 cannot bind effectively to the PCP receptor, because the NMDA channel remains closed and access of $[^3H]$-MK801 to the PCP receptor inside the closed channel pore is severely restricted.

The assay is conducted using rat brain membrane homogenates which are enriched in NMDA receptors. The membranes are prepared as follows. Frozen rat brains (obtained from Pel-Freez, Rogers, Ark.) are homogenized in 15 volumes (w/v) of ice cold 0.32M sucrose. The homogenate is spun at 1,000×g for ten minutes. The supernatant is collected and spun for 20 minutes at 44,000×g. The pellet is suspended in 15 volumes of water (relative to original brain weight). The homogenate is again spun at 44,000×g for twenty minutes. The pellet is resuspended in 5 volumes of water and the suspension is freeze-thawed 2 times. After the final thaw cycle, the suspension is brought to 15 volumes with water and spun at 44,000×g for twenty minutes. The pellet is resuspended in 5 volumes of ice-cold 10 μmM HEPES, and is titrated to pH 7.4 with KOH containing 0.04% Triton X-100. Membranes are incubated with the Triton/HEPES buffer at 37° C. for 15 minutes. The volume is then brought to 15 with ice-cold 10 mM HEPES, pH 7.4, and spun/washed three times with spins of 44,000×g between washes. The final pellet is suspended in three volumes of 50 mM HEPES, pH 7.4 and the protein concentration is determined with a standard dye-binding protein assay (Bio-Rad, Richmond, Calif.). The suspension is stored at −80° C. until used. Only HPLC grade water is used for all buffers and suspensions/washings. The extensive washings are necessary to remove as much endogenous glycine from the membrane preparation as possible.

On the day of the assay, the previously prepared membranes are thawed and 5 mM Tris/HCl buffer, pH 7.4, is added to yield a final protein concentration of 0.156 mg/mL. For binding assays, 0.8 mL of membranes are pipetted into polypropylene tubes followed by 0.033 mL of 15.1 μM 5,7-dichlorokynurenic acid (DCK), 0.033 mL of 30.3 μM glycine in buffer (or buffer alone), 0.033 mL of 303 μM glutamate in buffer (or for controls, 0.1 mL 1 mM PCP instead of DCK/gly/glu), 0.033 mL glycine antagonist in buffer (or buffer alone) and 0.1 mL buffer containing 200,000 cpm [$^3$H]-MK801. Nonspecific binding is defined as the difference in binding that occurs in the absence or presence of PCP (final concentration: 100 μM). To determine the effect of 1 μM glycine on the binding of [$^3$H]-MK801, bound radioactivity in the presence of 10 μM glutamate alone (final concentration) is subtracted from the bound radioactivity in the presence of both 10 μM glutamate and 1 μM glycine (final concentration). A 500 nM concentration (final) of 5,7-dichlorokynurenic (DCK) acid is added to all assay tubes. This concentration of the glycine antagonist DCK "buffers" most of the residual endogenous glycine that is not removed by the extensive washing steps that are carried out during the membrane preparation procedure. The 500 nM DCK does not interfere with the stimulation of [$^3$H]-MK801 binding that is effected by the addition of 1 μM exogenous glycine.

The assays are incubated for 120 minutes at room temperature after which time the membrane-bound radioactivity is isolated from the free radioactivity by vacuum filtration through Whatman glass fiber filters that had been pretreated with 0.3% polyethyleneimine. Filtration is accomplished using a Brandel 48 well cell harvester. Filtered membranes are washed three times with 3 mL each of ice cold buffer. Filters are transferred to scintillation vials and 5 mL of scintillation cocktail is added. The vials are shaken overnight and the radioactivity is counted by liquid scintillation spectroscopy. The assays are done in triplicate and all experiments are conducted at least three times.

Inhibition dose response curves are constructed using increasing concentrations of glycine antagonists from 5 nM to 330 μM. IC$_{50}$ values are determined for compounds active in inhibiting 1 μM glycine-stimulated [$^3$H]-MK801 binding by computer-assisted plotting of the inhibition curves and interpolation. When compounds are found to inhibit glycine-stimulated [$^3$H]-MK801 binding, experiments are conducted to determine whether the inhibition of the glycine-stimulated [$^3$H]-MK801 binding is indeed mediated at the glycine binding site of the NMDA receptor. In these experiments, a fixed concentration of antagonist sufficient to produce a >95% inhibition of the 1 μM glycine-stimulated [$^3$H]-MK801 binding is incubated with the membranes without any additional glycine (above 1 μM) and in the presence of increasing concentrations of additional glycine (2 μM to 1 μM). If the inhibition of [$^3$H]-MK801 binding by the drug in the presence of 1 μM glycine is fully reversed by adding increasing concentrations of glycine, then the inhibition of [$^3$H]-MK801 binding is mediated by the drug acting as an antagonist at the glycine binding site of the NMDA receptor.

After constructing inhibition dose response curves and determination of glycine reversibility, K$_i$ values for the glycine antagonists are calculated using the Cheng and Prusoff equation employing the experimentally determined IC$_{50}$ values, the known concentration of glycine in the assay (1 μM) and the known affinity of glycine for the glycine binding site of the NMDA receptor (100 nM).

The same rat brain membrane homogenates used for the 1 μM glycine-stimulated [$^3$H]-MK801 binding assay are used for the [$^3$H]-AMPA radioligand binding assay. On the day of the assay the frozen membranes (prepared as described above) are thawed and diluted with 30 mM Tris/HCl buffer containing 2.5 mM CaCl$_2$ and 100 mM KSCN, pH 7.4, to yield a final membrane concentration of 1.25 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-AMPA. The assay is incubated for 30 minutes on ice. Bound radioactivity is separated from free radioactivity by filtration over Whatman glass fiber filters (pretreated with 0.3% polyethyleneimine) using a Brandel 48 well cell harvester.

Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 10 nM to 100 μM.

The same membrane preparation as that used for the [$^3$H]-AMPA binding assay may be used for the [$^3$H]-Kainate radioligand binding assay. On the day of the assay the frozen rat brain membranes are thawed and 5 mM Tris/HCl buffer, pH 7.4, is added to yield a final concentration of 0.5 mg/mL membrane protein. For the binding assay, 0.8 mL of membrane homogenate is added to polypropylene tubes followed by 0.033 mL drug and 0.067 mL buffer (or for controls by 0.1 mL buffer alone) and 0.1 mL buffer containing 200,000 cpm of [$^3$H]-kainate. The assay is incubated for 2 hours on ice. Bound radioactivity is separated from free radioactivity by filtration over Whatman glass fiber filters (pretreated with 0.3% polyethyleneimine) using a Brandel 48 well cell harvester. Filtered membranes are washed three times with 3 mL each of ice cold buffer. The filters are transferred to scintillation vials and 5 mL of scintillation cocktail is added. The vials are shaken overnight and radioactivity is counted by liquid scintillation spectroscopy. Nonspecific binding is determined by the radioactivity that remains bound to the membranes in the presence 10 mM glutamate. Inhibition dose response curves are constructed by adding increasing concentrations of drug from 250 nM to 330 μM.

The binding affinities of quinoxaline-2,3-diones at NMDA receptor glycine sites also were estimated by electrophysiological assay either using cloned rat NMDA receptors expressed in Xenopus oocytes, or non-NMDA receptors expressed in oocytes by whole rat brain poly(A)+RNA. See, U.S. application Ser. No. 08/148,259 now U.S. Pat. No. 5,519,680. $K_b$ values were estimated by assuming competitive inhibition and assaying suppression of membrane current responses elicited by fixed concentrations of agonist: 1 mM glycine and 100 mM glutamate for NMDA receptors; 20 mM kainic acid for non-NMDA receptors. For NMDA receptors, $K_b$s were approximated by averaging values at three subtype combinations (NR1A/NR2A, NR1A/NR2B, and NR1A/NR2C).

The anxiolytic activity of any particular compound of the present invention may be determined by use of any of the recognized animal models for anxiety. A preferred model is described by Jones, B. J. et al., *Br. J. Pharmacol.* 93:985–993 (1988). This model involves administering the compound in question to mice which have a high basal level of anxiety. The test is based on the finding that such mice find it aversive when taken from a dark home environment in a dark testing room and placed in an area which is painted white and brightly lit. The test box has two compartments, one white and brightly illuminated and one black and non-illuminated. The mouse has access to both compartments via an opening at floor level in the divider between the two compartments. The mice are placed in the center of the brightly illuminated area. After locating the opening to the dark area, the mice are free to pass back and forth between the two compartments. Control mice tend to spend a larger proportion of time in the dark compartment. When given an anxiolytic agent, the mice spend more time exploring the more novel brightly lit compartment and exhibit a delayed latency to move to the dark compartment. Moreover, the mice treated with the anxiolytic agent exhibit more behavior in the white compartment, as measured by exploratory rearings and line crossings. Since the mice can habituate to the test situation, naive mice should always be used in the test. Five parameters may be measured: the latency to entry into the dark compartment, the time spent in each area, the number of transitions between compartments, the number of lines crossed in each compartment, and the number of rears in each compartment. The administration of the compounds of the present invention is expected to result in the mice spending more time in the larger, brightly lit area of the test chamber.

In the light/dark exploration model, the anxiolytic activity of a putative agent can be identified by the increase of the numbers of line crossings and rears in the light compartment at the expense of the numbers of line crossings and rears in the dark compartment, in comparison with control mice.

A second preferred animal model is the rat social interaction test described by Jones, B. J. et al., supra, wherein the time that two mice spend in social interaction is quantified. The anxiolytic activity of a putative agent can be identified by the increase in the time that pairs of male rats spend in active social interaction (90% of the behaviors are investigatory in nature). Both the familiarity and the light level of the test arena may be manipulated. Undrugged rats show the highest level of social interaction when the test arena is familiar and is lit by low light. Social interaction declines if the arena is unfamiliar to the rats or is lit by bright light. Anxiolytic agents prevent this decline. The overall level of motor activity may also be measured to allow detection of drug effects specific to social behaviors.

The efficacy of the glycine and excitatory amino acid antagonists to inhibit glutamate neurotoxicity in rat brain cortex neuron cell culture system may be determined as follows. An excitotoxicity model modeled after that developed by Choi (Choi, D. W., *J. Neuroscience* 7:357 (1987)) may be used to test anti-excitotoxic efficacy of the glycine and excitatory amino acid antagonists. Fetuses from rat embryonic day 19 are removed from time-mated pregnant rats. The brains are removed from the fetuses and the cerebral cortex is dissected. Cells from the dissected cortex are dissociated by a combination of mechanical agitation and enzymatic digestion according to the method of Landon and Robbins (*Methods in Enzymology* 124:412 (1986)). The dissociated cells are passed through a 80 micron nitex screen and the viability of the cells are assessed by Trypan Blue. The cells are plated on poly-D-lysine coated plates and incubated at 37° C. in an atmosphere containing 91% $O_2$/9% $CO_2$. Six days later, fluoro-d-uracil is added for two days to suppress non-neural cell growth. At culture day 12, the primary neuron cultures are exposed to 100 μM glutamate for 5 minutes with or without increasing doses of glycine and excitatory amino acid antagonist or other drugs. After 5 minutes the cultures are washed and incubated for 24 hours at 37° C. Neuronal cell damage is quantitated by measuring lactate dehydrogenase (LDH) activity that is released into the culture medium. The LDH activity is measured according to the method of Decker et al. (Decker et al., *J. Immunol. Methods* 15:16 (1988)).

The anticonvulsant activity of the glycine and excitatory amino acid antagonists may be assessed in the audiogenic seizure model in DBA-2 mice as follows. DBA-2 mice may be obtained from Jackson Laboratories, Bar Harbor, Me. These mice at an age of <27 days develop a tonic seizure within 5–10 seconds and die when they are exposed to a sound of 14 kHz (sinus wave) at 110 dB (Lonsdale, D., *Dev. Pharmacol. Ther.* 4:28 (1982)). Seizure protection is defined when animals injected with drug 30 minutes prior to sound exposure do not develop a seizure and do not die during a 1 minute exposure to the sound. 21 day old DBA-2 mice are used for all experiments. Compounds are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant efficacy of the glycine receptor antagonists may be assessed in the pentylenetetrazol (PTZ)-induced seizure test as follows. Swiss/Webster mice, when injected with 50 mg/kg PTZ (i.p.) develop a minimal clonic seizure of approximately 5 seconds in length within 5–15 minutes after drug injection. Anticonvulsant efficacy of a glycine/excitatory amino acid antagonist (or other) drug is defined as the absence of a seizure when a drug is given 30 minutes prior to PTZ application and a seizure does not develop for up to 45 minutes following PTZ administration. Glycine/excitatory amino acid antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The efficacy of glycine/excitatory amino acid antagonists to protect mice from NMDA-induced death may be assessed as follows. When mice are injected with 200 mg/kg N-methyl-D-aspartate (NMDA) i.p., the animals will develop seizures followed by death within 5–10 minutes. Glycine/excitatory amino acid antagonists are tested for their ability to prevent NMDA-induced death by giving the drugs i.p. 30 minutes prior to the NMDA application. Glycine/excitatory amino acid antagonist or other drugs are given intraperitoneally in either saline, DMSO or polyethyleneglycol-400. Appropriate solvent controls are included in each experiment. Dose response curves are constructed by giving increasing doses of drug from 1 mg/kg to 100 mg/kg. Each dose group (or solvent control) consists of at least six animals.

The anticonvulsant activity of the glycine antagonists may be assessed in the maximum electroshock-induced seizure (MES) assays in mice. Electroshock is applied to male Swiss/Webster mice (20–30 g, Simonsen) through corneal electrodes (Swinyard, E. A. in *Anticonvulsant drugs*, Mercier J. Ed. Pergamon Press, Oxford (1973) pp. 47–65). The seizure stimulus parameters were: 50 mA, 60 Hz, rectangular pulse, width 0.8 msec, duration 200 msec. Tonic hind limb extension observed after application of the electrical stimulus is recorded as occurrence of seizure. The drug may be applied i.v. as an aqueous basic solution.

A series of different evaluations may be conducted on doses of the glycine/excitatory amino acid antagonists of the invention to determine the biological activity of the compounds both in normal gerbils and in animals exposed to 5 minutes of bilateral carotid occlusion. See Scheme I.

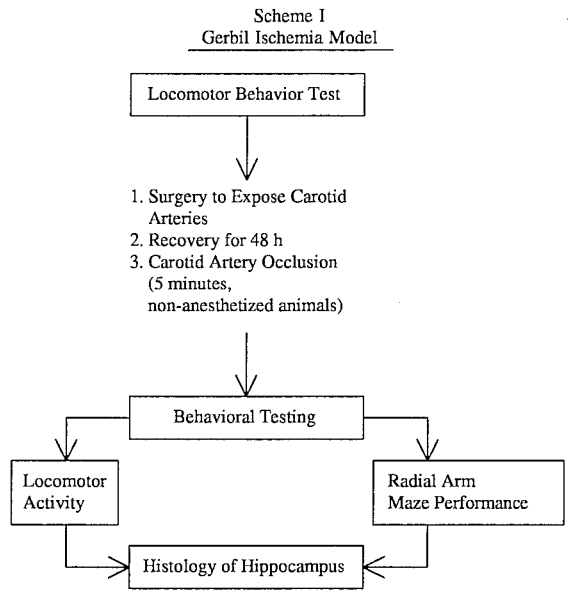

Scheme I
Gerbil Ischemia Model

These studies are conducted in animals who are conscious and have no other pharmacological agents administered to them. Gerbils are preinstrumented 48-hours prior to ischemia to allow for the complete elimination of the pentobarbital anesthetic which is employed. When tested with drugs, animals are given IP injections of the glycine/excitatory amino acid antagonist or vehicle. In the case of multiple injections, animals are given IP injections 2 hours apart and the final injection is given 30 minutes prior to the ischemic period or in the case of post treatment, the animals are given injections at 30 minutes, 2 hours, 4 hours and 6 hours post-ischemic reperfusion.

In order to assess the direct pharmacological activity or potential activity of the glycine/excitatory amino acid antagonists, naive gerbils are injected with either saline or differing doses of the antagonist. The behavioral changes are assessed using a photobeam locomotor activity chamber which is a two foot circular diameter arena with photobeam detection. Animals are individually placed in the 2 foot diameter chambers. The chambers are housed in a cabinet which is closed and noise is abated using both a background white noise generator and a fan. Animals are placed in these chambers in the case of the initial pharmacological evaluation for a period of 6 hours and the total activity during each successive hour is accumulated using the computer control systems.

Saline results in an initial high rate of activity, with the control animals showing a first hour activity level of about 1600 counts. This level of control activity is typical for the gerbil under these experimental conditions. As the session progressed, animals decrease their exploratory activity and at the terminal period the activity declines to about 250 counts per hour. It is expected that the glycine/excitatory amino acid antagonists of the present invention will have no significant effect on either the initial exploratory rate or the terminal rate of exploration.

In a next phase of the evaluation of the glycine/excitatory amino acid antagonists, gerbils are pretreated with varying doses of the antagonists and then exposed to a five minute period of bilateral carotid occlusion. Following the initiation of reperfusion, animals are placed into the circular locomotor activity testing apparatus and the activity at the beginning of the first hour following reperfusion is monitored for the subsequent four hours.

Control animals not exposed to ischemia and given injections of saline prior to being placed in the locomotor activity chamber show a characteristic pattern of activity which in the first hour of locomotor activity is substantially higher than during all other hours and progressively declined over the four hours to a very low value. In contrast to the progressive decline in activity over the four hour testing period, control animals that are exposed to five minutes of cortical ischemia demonstrate a completely different pattern of locomotor activity. During the first hour there is a significant decline in activity which is followed by a progressive increase in which the activity during the fourth hour is ten-fold higher than that demonstrated by animals not exposed to carotid occlusion. These results are typical and are a reliable result of the alterations caused by five minutes of bilateral carotid occlusion in the gerbil.

Separate groups of gerbils are pretreated with the glycine/excitatory amino acid antagonists of the invention 30 minutes before the onset of carotid occlusion and then placed into the locomotor activity following one hour of reperfusion. It is expected that pretreatment of the gerbils with the glycine/excitatory amino acid antagonists of the invention will prevent both the post-ischemic decrease and increase in activity. Post-ischemic decreases in activity are expected to be near zero during the first hour following reperfusion. Pretreatment with the glycine/excitatory amino acid antagonists of the invention is expected to reduce or prevent this early depression of behavior. In addition, the glycine/excitatory amino acid antagonists of the invention are expected to prevent the post-ischemic stimulation of behavior.

Subsequent to completion of the single dose pretreatment evaluations, gerbils are also evaluated with multiple injections of the glycine/excitatory amino acid antagonists of the invention. Doses are administered I.P. at 6 hours, 4 hours, 2 hours and 30 minutes prior to the onset of 5 minutes of ischemia.

At 24 hours all animals are evaluated for differences in patrolling behavior using a 8-arm radial maze. In this procedure, animals are placed into the center start chamber of the maze, the barrier removed and the amount of time and the number of times the animal makes an error recorded prior to completion of exploration in all 8 arms of the maze.

An error is defined as the revisiting of an arm by entering to the extent of the entire body without including tail by the animal. If the animal perseveres or fails to leave the arm for longer than five minutes, the session is terminated. In the control population of the animals, the number of errors and exploration of the maze with no prior experience (naive) is approximately 6 errors. This is an average value for an N of 28 gerbils. Following 5 minutes of bilateral carotid occlusion and testing at 24 hours, gerbils make an average number of errors of 21. When animals are pretreated with the glycine/excitatory amino acid antagonists of the invention, there is expected to be a significant reduction in the number of errors made. There is also expected to be a significant sparing of the behavioral changes that are induced in the radial arm maze performance.

It is also expected that post treatment the glycine/excitatory amino acid antagonists of the invention will reduce the short term memory impairment 24 hours post ischemic/reperfusion.

The effects of 5 minutes of bilateral carotid occlusion on neuronal cell death in the dorsal hippocampus may be evaluated in animals 7 days after ischemia reperfusion injury. Previous studies have demonstrated that neuronal degeneration begins to occur around 3 days following cerebral ischemia. By 7 days those neurons which have been affected and will undergo cytolysis and have either completed degeneration or are readily apparent as dark nuclei and displaced nuclei with eosinophilic cytoplasm with pycnotic nuclei. The lesion with 5 minutes of ischemia is essentially restricted within the hippocampus to the CA1 region of the dorsal hippocampus. The intermedial lateral zone of the horn is unaffected and the dentate gyrus and/or in CA3 do not show pathology. Gerbils are anesthetized on day 7 following ischemia with 60 mg/kg of pentobarbital. Brains are perfused transcardiac with ice-cold saline followed by buffered paraformaldehyde (10%). Brains are removed, imbedded and sections made. Sections are stained with hematoxylin-eosin and neuronal cell counts are determined in terms of number of neuronal nuclei/100 micrometers. Normal control animals (not exposed to ischemia reperfusion injury) will not demonstrate any significant change in normal density nuclei within this region. Exposure to five minutes of bilateral carotid occlusion results in a significant reduction in the number of nuclei present in the CA1 region. In general, this lesion results in a patchy necrosis instead of a confluent necrosis which is seen if 10 minutes of ischemia is employed. Pretreatment with the glycine receptor antagonists of the invention are expected to produce a significant protection of hippocampal neuronal degeneration.

It is known that NMDA receptors are critically involved in the development of persistent pain following nerve and tissue injury. Tissue injury such as that caused by injecting a small amount of formalin subcutaneously into the hindpaw of a test animal has been shown to produce an immediate increase of glutamate and aspartate in the spinal cord (Skilling, S. R., et al., *J. Neurosci.* 10:1309–1318 (1990)). Administration of NMDA receptor blockers reduces the response of spinal cord dorsal horn neurons following formalin injection (Dickenson and Aydar, *Neuroscience Lett.* 121:263–266 (1991); Haley, J. E., et al., *Brain Res.* 518:218–226 (1990)). These dorsal horn neurons are critical in carrying the pain signal from the spinal cord to the brain and a reduced response of these neurons is indicative of a reduction in pain perceived by the test animal to which pain has been inflicted by subcutaneous formalin injection.

Because of the observation that NMDA receptor antagonists can block dorsal horn neuron response induced by subcutaneous formalin injection, NMDA receptor antagonists have potential for the treatment of chronic pain such as pain which is caused by surgery or by amputation (phantom pain) or by infliction of other wounds (wound pain). However, the use of conventional NMDA antagonists such as MK801 or CGS 19755, in preventing or treating chronic pain, is severely limited by the adverse PCP-like behavioral side effects that are caused by these drugs. It is expected that the glycine receptor antagonists that are the subject of this invention will be highly effective in preventing chronic pain in mice induced by injecting formalin subcutaneously into the hindpaw of the animals. Because the glycine/excitatory amino acid antagonists of this invention are expected to be free of PCP-like side effects, these drugs are highly useful in preventing or treating chronic pain without causing PCP-like adverse behavioral side effects.

The effects of the glycine receptor antagonists of the present invention on chronic pain may be evaluated as follows. Male Swiss/Webster mice weighing 25–35 grams are housed five to a cage with free access to food and water and are maintained on a 12 hour light cycle (light onset at 0800 h). The glycine receptor antagonist is dissolved in DMSO at a concentration of 1–40 and 5–40 mg/mL, respectively. DMSO is used as vehicle control. All drugs are injected intraperitoneally (1 µl/g). The formalin test is performed as described (Dubuisson and Dennis, *Pain* 4:H161–174 (1977)). Mice are observed in a plexiglass cylinder, 25 cm in diameter and 30 cm in height. The plantar surface of one hindpaw is injected subcutaneously with 20 µl of 5% formalin. The degree of pain is determined by measuring the amount of time the animal spends licking the formalin-injected paw during the following time intervals: 0–5' (early phase); 5'–10', 10'–15' and 15'–50' (late phase). To test whether the glycine/excitatory amino acid antagonists prevent chronic pain in the test animals, vehicle (DMSO) or drugs dissolved in vehicle at doses of 1 mg/kg to 40 mg/kg are injected intraperitoneally 30 minutes prior to the formalin injection. For each dose of drug or vehicle control at least six animals are used.

Compared to vehicle control, it is expected that the intraperitoneal injection of the glycine receptor antagonists 30 minutes prior to formalin injection into the hindpaw will significantly inhibit formalin-induced chronic pain in a dose-dependent manner as determined by the reduction of the time spent licking by the mouse of the formalin injected hindpaw caused by increasing doses of glycine/excitatory amino acid antagonist.

Compositions within the scope of this invention include all compositions wherein the compounds of the present invention are contained in an amount which is effective to achieve its intended purpose. While individual needs vary, determination of optimal ranges of effective amounts of each component is with the skill of the art. Typically, the compounds may be administered to mammals, e.g., humans, orally at a dose of 0.0025 to 50 mg/kg, or an equivalent amount of the pharmaceutically acceptable salt thereof, per day of the body weight of the mammal being treated for anxiety disorders, e.g., generalized anxiety disorder, phobic disorders, obsessional compulsive disorder, panic disorder, and post traumatic stress disorders. Preferably, about 0.01 to about 10 mg/kg is orally administered to treat or prevent such disorders. For intramuscular injection, the dose is generally about one-half of the oral dose. For example, for treatment or prevention of anxiety, a suitable intramuscular dose would be about 0.0025 to about 15 mg/kg, and most preferably, from about 0.01 to about 10 mg/kg.

In the method of treatment or prevention of neuronal loss in ischemia, brain and spinal cord trauma, hypoxia, hypoglycemia, and surgery, as well as for the treatment of Alzheimer's disease, amyotrophic lateral sclerosis, Huntington's disease and Down's Syndrome, or in a method of treating a disease in which the pathophysiology of the disorder involves hyperactivity of the excitatory amino acids or NMDA receptor-ion channel related neurotoxicity, the pharmaceutical compositions of the invention may comprise the compounds of the present invention at a unit dose level of about 0.01 to about 50 mg/kg of body weight, or an equivalent amount of the pharmaceutically acceptable salt thereof, on a regimen of 1–4 times per day. When used to treat chronic pain or to induce anesthesia, the compounds of the invention may be administered at a unit dosage level of from about 0.01 to about 50 mg/kg of body weight, or an equivalent amount of the pharmaceutically acceptable salt thereof, on a regimen of 1–4 times per day. Of course, it is understood that the exact treatment level will depend upon the case history of the animal, e.g., human being, that is treated. The precise treatment level can be determined by one of ordinary skill in the art without undue experimentation.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compounds as raw chemicals, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the nontoxic pharmaceutically acceptable salts of the compounds of the present invention. Basic salts are formed by mixing a solution of the particular compound the present invention with a solution of a pharmaceutically acceptable non-toxic base such as sodium hydroxide, potassium hydroxide, choline hydroxide, sodium bicarbonate, sodium carbonate, Tris and the like.

The pharmaceutical compositions of the invention may be administered to any animal which may experience the beneficial effects of the compounds of the invention. Foremost among such animals are humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal or ocular routes. Alternatively, or concurrently, administration may be by the oral route. The dosage administered will be dependent upon the age, health, and weight of the recipient, kind of concurrent treatment, if any, frequency of treatment, and the nature of the effect desired.

When the compositions of the invention are administered ocularly, one may achieve either local or systemic administration. For example, the compositions of the present invention may be administered in the form of eye drops which are substantially isotonic with tear fluid to achieve systemic administration. Preferably, such compositions will also comprise a permeation-enhancing agent which aids the systemic absorption of the compounds of the present invention. See, U.S. Pat. No. 5,182,258. Alternatively, the compositions of the invention may be administered ocularly to treat or prevent optic nerve degeneration. In this embodiment, the compounds of the present invention are administered in the form of eye drops, as disclosed above, or may be injected into the vicinity of the optic nerve. In the alternative, thin ocular implants may be employed which slowly release the compounds of the present invention.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, are present at a concentration of from about 0.01 to 99 percent, together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, crosslinked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The characterization of glycine binding sites in vitro has been difficult because of the lack of selective drug ligands. Thus, the glycine ligands of the present invention may be used to characterize the glycine binding site. Particularly preferred compounds which may be used for this purpose are isotopically labelled, e.g., radiolabelled derivatives, e.g., where one or more of the atoms are replaced with $^{3}H$, $^{11}C$, $^{14}C$, $^{15}N$, or $^{18}F$.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

Example 1

Preparation of 4,1-Benzoxazine;2,3-dione (2a).

To a mixture of 2.29 g (21.0 mmol) of o-aminophenol in 25 mL of dry toluene was added portion wise 11 mL of 2N oxalyl chloride/$CH_2Cl_2$ (22.0 mmol) solution. The mixture was refluxed for 4 h, cooled to room temperature, filtered and the solid was washed with xylene and water, and dried to leave 3.10 g (90%) of 2a as pale-green solid. The analytical sample was obtained by crystallization from acetone, mp 263°–264° C. (lit, 264°–266° C.; Bernard et al, *J. Med. Chem.* 28:240 (1985)). $^{1}H$ NMR (CDCl$_3$+DMSO-d$_6$), 6.932 (m, 4), 11.970 (m, 1).

Example 2

Preparation of 7-Chloro-4,1-benzoxazine-2,3-dione (2d).

Compound 2d was prepared similar to 2a. From 2.88 g (20.0 mmol) of 2-amino-4-chlorophenol and 10 mL of 2N oxalyl chloride/$CH_2Cl_2$ (22.0 mmol) solution there was obtained 3.50 g of pale green solid. The analytical sample was obtained by crystallization from chlorobenzene, mp 280°–281° C. (lit, 289°–292° C.; Bernard et al, *J. Med. Chem.* 28:240 (1985)). $^{1}H$ NMR (CDCl$_3$+DMSO-d$_6$), 6.826 (dd, 1, J=2.1, 8.7), 6.910 (d, 1, J=8.7), 6.933 (d, 1, J=2.1), 12.056 (sb, 1).

Example 3

Preparation of 5,7-Dichloro-4,1-benzoxazine-2,3-dione(2e).

To a solution of 387 mg (1.43 mmol) of $K_2S_2O_8$ in 1 mL of $H_2SO_4$ (96%) in ice-bath was added in one portion 222 mg (1.02 mmol) of 4,6-dichloroisatin and the mixture was stirred in ice-bath for 5 min to become an almost colorless solution. To the solution was added 2 mL of ice-water and the mixture was stirred for 5 min. The mixture was filtered, washed by icewater, and dried to leave almost colorless solid 227 mg (95%), mp>250° C. $^{1}H$ NMR (CDCl$_3$+DMSO-d$_6$), 6.837 (d, 1, J=1.9), 6.900 (d, 1, J=1.9), 12.17 (mb, 1). MS, 231 (40, M$^+$), 203 (100), 147 (40), 112 (60). High resolution MS, Calcd for $C_8H_3NO_3$ 230.9487, found 230.9489.

Example 4

Preparation of 2,3-Dihydroxyquinoline (5a).

3-Methoxy-2-quinolone (5). To a mixture of 1.05 g (7.1 mmol) of isatin in 15 mL of ether in ice-bath was added dropwise a solution of diazomethane in ether (prepared from 4.4 g (20 mmol) of Diazald according to *Aldrichimica Acta* 16:3 (1983)). The resulting solution was stirred in ice-bath for 3 h then room temperature overnight. The mixture was filtered and dried to leave white solid 0.684 g (52%), mp 188°–189° C. (lit. 191° C.; Greibrokk and Undheim, *Acta Chem. Scand.* 25:2935 (1971)). $^{1}H$ NMR (CDCl$_3$) 3.977 (s, 3), 7.014 (s, 1), 7.21 (m, 1), 7.39 (m, 2), 7.509 (d, 1, J=7.8), 11.429 (s, 1).

2,3-Dihydroxyquinoline (5a). A solution of 301 mg of 3-methoxy-2-quinolone (1.71 mmol) in 1 mL of acetic acid and 1 mL of HBr (48%) was refluxed for 2 days and cooled to room temperature. The mixture was diluted by 2 mL of water, filtered and washed by water, and dried to leave almost colorless solid (281 mg). The solid was dissolved in 2 mL of aqueous 2N NaOH and the solution was acidified by 1N HCl to pH=6. The white precipitate was filtered and washed by water, dried to leave white solid (250 mg), mp 261°–262° C. (lit, 266° C.; Greibrokk and Undheim, *Acta Chem. Scand.* 25:2935 (1971)). $^{1}H$ NMR (CDCl$_3$+DMSO-d$_6$) 6.618 (s, 1), 6.698 (t, 1, J=7.5), 6.809–6.901 (m, 2), 6.985 (d, 1, J=7.8), 8.061 (s, 1), 11.448 (s, 1).

Example 5

Preparation of 6-Fluoro-2,3-dihydroxyquinoline (5b).

Compound 5b was prepared similar to 5a. From 1.15 g (7.0 mmol) of 5-fluoroisatin and diazomethane (prepared from 13 mmol of Diazald) there was obtained 1.01 g (75%) of pale brown solid. From 524 mg of this solid and 2.5 mL of acetic acid and 2.5 mL of HBr (48%) there was obtained 422 mg of brown solid. The solid was purified by aqueous NaOH/HCl to leave yellow solid 312 mg (64%), mp 273°–275° C. $^{1}H$ NMR (CDCl$_3$+DMSO-d$_6$) 6.728 (s, 1), 6.691–6.747 (m, 1), 6.824 (dd, 1, J=2.1, 9.0), 7.027 (dd, 1, J=4.8, 8.7), 8.09 (mb, 1), 11.64 (mb, 1). MS, 179 (100, M$^+$), 161 (20), 151 (22), 133 (30). High resolution MS, Calcd for $C_9H_6FNO_2$ 179.0380, found 179.0370.

Example 6

Preparation of 3-Oximinoquinolin-2,4-dione (10a).

To a mixture of 3.21 g (19.9 mmol) of 2,4-dihydroxyquinoline and 1.87 g (27.1 mmol) of $NaNO_2$ in 60 mL of 0.2N NaOH in an ice-bath was added dropwise 40 mL of aqueous 2N $H_2SO_4$. The mixture was stirred in an ice bath for 1 h after addition of $H_2SO_4$, filtered and dried to leave 3.41 g of orange solid which was crystallized by boiling with 150 mL of ethanol (95%) and filtered. The filtrate was cooled to and kept at room temperature for 5 h. The crystalline precipitate was filtered and dried to leave 1.88 g (50%) of 10a as a red solid, mp 206° C. (decomposed, lit 208° C., dec.). $^1$H NMR ($CDCl_3$+DMSO-$d_6$), 6.65–6.78 (m, 2), 7.15 (m, 1), 7.556 (d, 0.30, J=8.1), 7.605 (d, 0.70, J=8.1), 10.887 (s, 0.3), 11.346 (s, 0.7). MS, 190 (100, M$^+$), 173 (25), 146 (55). High resolution MS, Calcd for $C_9H_6N_2O_3$, 190.0375, found 190.0400.

Example 7

Preparation of 2,3,4-Trihydroxyquinoline (11a).

A mixture of 1.10 g (5.78 mmol) of 10a and 110 mg of 30% Pd/C in 100 mL of aqueous 1N HCl was hydrogenated at 50 psi for 7 h. Crystalline colorless solid was observed in the reaction mixture. The mixture was filtered and the solid was stirred with 50 mL of acetone/methanol (1:1) and filtered to remove the black catalyst. The acetone/methanol solution was added into the HCl aqueous solution to give crystalline solid. It was filtered, washed with water, and dried to leave 820 mg (80%) of 11a as a white crystalline solid, mp>250° C. $^1$H NMR (DMSO-$d_6$), 7.394 (t, 1, J=7.2), 7.490 (d, 1, J=7.8), 7.587 (t, 1, J=7.8), 7.964 (d, 1, J=7.8), 8.995 (s, 1), 10.317 (s, 1), 11.858 (s, 1). MS, 117 (100, M$^+$), 148 (5), 103 (35). High resolution MS, Calcd for $C_9H_7NO_3$ 177.0423, found 177.0439.

Example 8

Preparation of 5,7-Dichloro-2,3,4-trihydroxyquinoline (11b).

5,7-Dichloro-2,4-quinolinediol. A solution of 11.6 g (71.6 mmol) of 3,5-dichloroaniline and 26.3 g (164 mmol) of diethyl malonate was heated at 180° C. for 6 h and the ethanol produced was collected (~3.5 mL). The solution was cooled to room temperature and precipitate was observed. The mixture was filtered and washed by methanol (40 mL). The filtrate was mixed with 26 g of $Na_2CO_3$ and 200 mL of water and refluxed for 1 h. The solution was acidified by aqueous 2N HCl in an ice-bath to pH=1. The mixture was filtered and washed with water, and dried to leave white solid (13.9 g). The solid was mixed with 150 mL of polyphosphoric acid and heated at 140° C. for 3 h. The solution was cooled to room temperature and diluted with 200 mL of aqueous 1N HCl. The mixture was stirred for 4 h, then neutralized with aqueous 20% NaOH to pH=4. It was filtered, washed with water, and dried to leave 12.3 g (74%) of 5,7-dichloro-2,4-quinolinediol as white solid, mp 360°–361° C. (decomposed). $^1$H NMR ($CDCl_3$+DMSO-$d_6$), 5.447 (s, 1), 6.620 (d, 1, J=1.84) 6.804 (d, 1, J=1.86), 10.915 (sb, 1)). MS, 299 (100, M$^+$), 187 (80), 160 (30), 124 (20).

High resolution MS, Calcd for $C_9H_5{}^{35}Cl_2NO_2$ 228.9694, found 228.9709.

5,7-Dichloro-3-oximinoquinoline-2,4-dione (10b). To a mixture of 147 mg (0.616 mmol) of 5,7-dichloro-2,4-quinolinediol and 126 mg (1.82 mmol) of $NaNO_2$ in 3 mL of 0.2N NaOH in ice-bath was added dropwise 2 mL of aqueous 2N $H_2SO_4$. The mixture was stirred in ice-bath for 4 h after addition of $H_2SO_4$, filtered and dried to leave an orange solid. The solid was crystallized by boiling with 10 mL of ethanol (95% ). The solution was cooled to room temperature, filtered and dried to leave 132 mg (83%) of 5,7-dichloro-3-oximequinoline-2,4-dione as a yellow solid, mp 244°–245° C. (decomposed). $^1$H NMR ($CDCl_3$+DMSO-$d_6$), 7.011 (d, 0.44, J=1.8) 7.080 (m, 1.54), 11.567 (sb, 0.35), 11.821 (s, 0.46). MS, 258 (100, M$^+$), 241 (60), 214 (80), 187 (20), 160 (30). High resolution MS, Calcd for $C_9H_4{}^{35}Cl_2N_2O_3$, 257.9595, found 257.9598.

5,7-Dichloro-2,3,4-trihydroxyquinoline (11b). Compound 11b was prepared from 10b similar to 11a. mp 270°–273° C. $^1$H NMR (DMSO-$d_6$), 7.257 (s, 2) 9.306 (mb, 1), 9.998 (s, 1), 11.919 (s, 1).

Example 9

Preparation of Quinoline-2,3,4-trione (12a).

To a mixture of 335 mg (1.89 mmol) of 11a in 4 mL of aqueous 0.1N $H_2SO_4$ was added dropwise 10 mL of aqueous 0.2M $KIO_4$ (2 mmol) at 25° C. The mixture was stirred at 25° C. for 2 h, filtered and washed with water, dried to leave 222 mg (67%) of 12a as an almost colorless solid, mp>250° C. $^1$H NMR (DMSO-$d_6$), 7.043 (d, 1, J=8.4), 7.089 (t, 1, J=7.8), 7.232 (s, 2), 7.577 (t, 1, J=7.8), 7.735 (d, 1, J=7.5), 10.735 (s, 1). $^1$H NMR (DMSO-$d_6$+$D_2O$), 7.043 (d, 1), 7.098 (t, 1), 7.577 (t, 1), 7.735 (d, 1). MS, 175 (20, M$^+$), 147 (20), 119 (100), 92 (60). High resolution MS, Calcd for $C_9H_5NO_3$ 175.0267, found 175.0275.

Example 10

Preparation of 5,7-Dichloroquinolin-2,3,4-trione (12b).

Compound 12b was prepared from 11b similar to 12a as pale-yellow solid, mp 240° C. (dec.). $^1$H NMR (DMSO-$d_6$), 7.042 (d, 1, J=1.8), 7.312 (d, 1, J=1.8), 7.421 (s, 2), 10.918 (s, 1). $^1$H NMR (DMSO-$d_6$+$D_2O$), 7.054 (s, 1), 7.302 (s, 1).

Example 11

Preparation of 4,6-Dichloro-5(7)-nitroisatin (13e).

4,6-Dichloroisatin (13d). To a solution of 6.8 g (24 mmol) of tribromoacetaldehyde in 60 mL of water and 2 mL of 1N HCl was added successively 6.2 g (43 mmol) of sodium sulfate, a solution of 3.4 g (21 mmol) of 3,5-dichloroaniline in 40 mL of 1N HCl and a solution of 5.5 g (79 mmol) of hydroxylamine hydrochloride in 25 mL of water. The mixture was heated to vigorous boiling and kept boiling for 10 min, then cooled in ice-bath to room temperature. It was filtered, washed by water, and dried to leave pale-yellow solid (7.0 g). The solid was added portionwise into 50 mL of $H_2SO_4$ (96%) kept at 50° C. After the addition, the solution was heated to 80° C. and kept at 80° C. for 15 min. It was cooled to room temperature, and added into 450 mL of ice-water. After standing for 0.5 h, it was filtered, washed by water, and dried to 6.0 g of yellow solid. The solid was boiled with 180 mL of ethyl acetate, filtered and cooled to room temperature. The crystalline solid was collected and dried to give 2.40 g of yellow solid. A second collection of solid from the mother solution give 0.42 g of solid, total yield 2.82 g (60%), mp 244°–245° C. $^1$H NMR (CDCl$_3$+ DMSO-d$_6$), 6.559 (d, 1, J=1.0), 6.696 (d, 1, J=1.0), 10.978 (m, 1).

4,6-Dichloro-5(7)-nitroisatin (13e). A solution of 634 mg (2.93 mmol) of 13d and 322 mg (3.18 mmol) of KNO$_3$ in 4 mL of H$_2$SO$_4$ (96%) was stirred in ice-bath for 5 min and at room temperature overnight. The solution was added into 20 mL of ice-water, stirred, filtered and dried to leave yellow solid 715 mg (93%), mp 254°–255° C. $^1$H NMR (CDCl$_3$+ DMSO-d$_6$), 6.939 (s, 1), 11.288 (s, 1). MS, 260 (50, M$^+$), 243 (52), 213 (100), 185 (70). High resolution MS, Calcd for C$_8$H$_2$$^{35}$Cl$_2$N$_2$O$_4$ 259.9388, found 259.9390.

Example 12

Preparation of 4,5-Dichloro-7-nitroisatin (13h) and 5,6-Dichloro-7-nitroisatin (13i).

3,4-Dichloroanilinyl isonitrosoacetamide. To a solution of tribromoacetaldehyde (5.5mL, 50 mmol) in 0.5N aq. HCl (40 mL) was added successively sodium sulfate (13 g), a warm solution of 3,4-dichloroaniline (6.90 g, 42.6 mmol) in 200 mL of 1N HCl and a solution of NH$_2$OH.HCl (11.20 g, 165 mmol). The mixture was heated till vigorous boiling commenced. The boiling was allowed to continue for 30 min. The contents of the flask were cooled under running water to 22° C. The precipitate was filtered, washed with cold water (3×25 mL), dried to afford 6.40 g (64.6%) of orange-yellow powder, mp 165°–7° C. IR 1663, 1623, 1596, 1543, 1477, 1404 cm$^{-1}$; $^1$H NMR δ 12.294 (s, 1H, OH, D$_2$O exchange, fast), 10.459 (s, 1H, NH, D$_2$O exchange, slow), 8.060 (s, 1H), 7.617 (m, 3H); HRMS Calcd for C$_8$H$_6$Cl$_2$N$_2$O$_2$: 231.9806; Found: 231.9816.

4,5-Dichloroisatin (13f) and 5,6-dichloroisatin (13g). 5.50 g (23.7 mmol) of the amide obtained above was added in small portions to a stirred warm (50° C.) conc H$_2$SO$_4$ (100 mL) so as to keep the temperature between 60°–70° C. After the addition was over, the solution was heated at 110° C. with stirring for 1 h, then cooled to 22° C. and poured over crushed ice (500 g). After stirring for half an hour, the precipitate was collected on a sintered glass funnel, washed with cold water (3×50 mL), dried to afford 4.33 g (85%) of the isomeric mixture (by NMR) of 13f and 13g as a deep red powder. The mixture was dissolved in 200 mL of 0.5N aq. NaOH. The turbid solution was acidified first with conc HCl with vigorous stirring to about pH 6 (measured using a digital pH meter), then with 0.5N HCl to pH 4, the precipitate was removed by vacuum filtration. The clear filtrate was acidified with 0.5N HCl with vigorous stirring to pH 3, the precipitate was filtered, washed with pH 3 H$_2$O-HCl (3×5mL), and dried to afford 4.742 g (76%) of 4,5-dichloroisatin (13f) as a red powder. The analytical sample was obtained by crystallization from ethyl acetate as a red scales, mp 239°–40° C. (Lit. 250° C., Zieler & Hanus. *Monatsh. Chem.* 96:411 (1965); *Chem. Abstr.* 63:5635 (1965)). IR 1765, 1747, 1719, 1611 cm$^{-1}$; $^1$H NMR δ 11.278 (bs, 1H), 7.765 (d, J=8.4 Hz, 1H), 8.867 (d, J=8.4 Hz, 1H); HRMS Calcd for C$_8$H$_3$Cl$_2$NO$_2$: 214.9541; Found: 214.9547. The filtrate obtained after removing 13f was further acidified with 0.5N HCl to pH 1 with vigorous stirring. The precipitate was filtered, washed with pH 2 H$_2$O-HCl (3×5 mL), and dried to afford 218 mg (3.5%) of 5,6-dichloroisatin (13g) as an orange-yellow powder. The analytical sample was obtained by crystallization from ethyl acetate as a red needles, mp 271°–2° C. (Lit. 273°–5° C., Zieler & Hanus. *Monatsh. Chem.* 96:411 (1965); *Chem. Abstr.* 63:5635 (1965)). IR 1770, 1737, 1726, 1611 cm$^{-1}$; $^1$H NMR δ 11.253 (bs, 1H), 7.786 (s, 1H ), 7.117 (s, 1H); HRMS Calcd for C$_8$H$_3$Cl$_2$NO: 214.9541; Found: 214.9540.

4,5-Dichloro-7-nitroisatin (13h). To a solution of 4,5-dichloroisatin (13f, 430 mg, 2.0 mmol) in conc H$_2$SO$_4$ (5 mL) was added powdered KNO$_3$ (300 mg, 2.5 mmol) at 0° C. in portions with stirring. The mixture was stirred at 22° C. for 16 h, poured into ice-H$_2$O (50 mL). The precipitate was filtered, washed with H$_2$O (5×10 mL) and dried to give 295 mg (54%) of 13 h as a yellow powder. The analytical sample was obtained by crystallization from benzene, mp 204°–5° C. IR 1776, 1768, 1749, 1614, 1473, 1340, 1227 cm$^{-1}$; $^1$H NMR δ 11.932 (s, 1H), 8.535 (s, 1H). HRMS Calcd for C$_8$H$_2$Cl$_2$N$_2$O$_4$: 259.9391; Found: 259.9389.

5,6-Dichloro-7-nitroisatin (13i) was obtained in 51% yield from 5,6-dichloroisatin (13g) by using a similar procedure as that for 13h. Mp 200°–201° C.; IR: 1784, 1759, 1743, 1626, 1547, 1442, 1332 cm$^{-1}$; $^1$H NMR δ 11.934 (s, 1H), 8.125 (s, 1H); HRMS Calcd for C$_8$H$_2$Cl$_2$N$_2$O$_4$: 259.9391; Found: 259.9384.

Example 13

Preparation of 6-Chloro-5-nitroisatin (13j)

The title compound was obtained in 66% yield from 6-chloroisatin by using a similar procedure as that for 13h. Mp 205°–6° C.; IR 1761, 1744, 1624, 1528, 1339, 1324, 1210, 1013 cm$^{-1}$. $^1$H NMR δ 11.640 (s, 1H), 8.213 (s, 1H), 7.159 (s, 1H); HRMS Calcd, for C$_8$H$_3$ClN$_2$O$_4$: 225.9781; Found: 225.9764.

Example 14

Preparation of 5,7-Dichloroisatoic anhydride (14c).

To a mixture of 223 mg (10.3 mmol) of 13d in 2 mL of acetic acid with a drop of H$_2$SO$_4$ (96%) was added dropwise 0.2 mL of H$_2$O$_2$ (30%). The mixture was heated at 70°–80° C. for 2 h and cooled to room temperature. It was filtered, washed by water, and dried to leave a yellow crystalline solid (198 mg), mp 250°–251° C. $^1$H NMR (CDCl$_3$+DMSO-d$_6$), 6.868 (d, 1), 6.938 (d, 1) 11.68 (mb, 1). MS, 231 (30, M$^+$), 187 (100), 160 (50). High resolution MS, Calcd for C$_8$H$_3$$^{35}$Cl$_2$NO$_3$ 230.9487, found 230.9489.

Example 15

Preparation of 5,7-Dichloro-6(8)-nitroisatoic anhydride (14d).

Compound 14d was prepared similar to 14c. From 212 mg (0.812 mmol) of 13e there was obtained 153 mg (68%) of 14d, mp 289°–290° C. $^1$H NMR (CDCl$_3$+DMSO-d$_6$), 7.102 (s, 1), 12.15 (s, 1). MS, 276 (20, M$^+$), 232 (100), 202 (30). High resolution MS, Calcd for C$_8$H$_2$$^{35}$Cl$_2$N$_2$O$_5$ 275.9337, found 275.9334.

Example 16

Preparation of 6-Bromoisatoic anhydride (14b).

Compound 14b was prepared similar to 14c. From 2.26 g (10 mmol) of 5-bromoisatin and 15 mL of acetic acid, 0.1 mL of H$_2$SO$_4$ (96%) and 1.7 mL of H$_2$O$_2$ (30%) there was obtained 1.87 g (77%) of yellow solid. The analytical sample was obtained by crystallization from ethyl acetate as a yellow solid, mp 272°–276° C. (lit. 270–275; Reissenweber and Mangold, *Angew. Chem. Int. Ed. Eng.* 19:222 (1980)). $^1$H NMR (CDCl$_3$+DMSO-d$_6$), 6.87 (d, 1), 7.47 (dd, 1) 7.87 (d, 1), 11.5 (s, 1).

Example 17

Preparation of 5,6-Dichloroisatoic anhydride (14e).

To a suspension of 4,5-dichloroisatin (13f, 216 mg, 1.0 mmol) in glacial acetic acid (5 mL) and 2 drops (about 0.02 mL) of conc H$_2$SO$_4$ was added 0.34 mL (about 3 mmol) of 30% H$_2$O$_2$. The mixture was stirred at 70° C. (bath) for 2.5 h (the mixture turned into a solution, then formed a precipitate), allowed to cool to 22° C. and cold water (10 mL) was added. The precipitate was filtered, washed with water (6×10 mL), dried to give 208 mg (90%) of 14e as an orange-yellow powder, mp 267°–9° C. (dec). IR, 1810, 1779, 1762, 1711, 1600, 1335, 1254, 1041, 1024 cm$^{-1}$; $^1$H NMR δ 11.952 (bs, 1H), 7.928 (d, J=8.7 Hz, 1H), 7.110 (d, J=8.7Hz, 1H); HRMS Calcd for C$_8$H$_3$Cl$_2$NO$_3$: 230.9490; Found: 230.9489.

Example 18

Preparation of 6,7-Dichloroisatoic anhydride (14f).

6,7-Dichloroisatoic anhydride was obtained from 5,6-dichloroisatin (13g) in 83% yield by using a similar procedure as above, mp 263–5 (dec). IR 1784, 1771, 1702, 1486, 1398, 1316, 1037 cm$^{-1}$; $^1$H NMR δ 11,947 (bs, 1H), 8.085 (s, 1H), 7.300 (s, 1H); HRMS Calcd for C$_8$H$_3$Cl$_2$NO$_3$: 230.9490; Found: 230.9503.

Example 19

Preparation of 2,3,5-trihydro-1H,4H-1,4-Benzodiazepine-2,5-dione (73a).

A solution of 1.63 g (10 mmol) of isatoic anhydride, 750 mg (10 mmol) of glycine and 25 mL of acetic acid was refluxed for 4 h and cooled to room temperature. It was neutralized by addition portionwise of 10 g of sodium bicarbonate, followed by 10 mL of 30% ammonium hydroxide and allowed to stand overnight. The mixture was filtered, washed by water, and dried to leave a solid (762 mg) which is about 60% pure by $^1$H NMR. More solid was observed in the mother solution after standing at room temperature for 2 days. It was filtered, washed by water, and dried to leave a solid (360 mg, 20%), mp 319°–320° C. (lit. 327° C.; Mohiuddin et al., *Ind. J. Chem.* 24B:905 (1985)). $^1$H NMR (CDCl$_3$+DMSO-d$_6$) δ 3.19 (d, 2, J=6.0), 6.640 (d, 1, J=8.1), 6.705 (t, 1, J=7.5), 6.959 (t, 1, J=7.8), 7.360 (d, 1, J=7.8), 7.88 (mb, 1), 9.740 (s, 1).

Example 20

Preparation of 7-chloro-2,3,5-trihydro-1H,4H-1,4-benzodiazepine-2,5-dione (73b).

A solution of 1.98 g (10.0 mmol) of 6-chloroisatoic anhydride and 761 mg (10.1 mmol) of glycine in 25 mL of acetic acid was refluxed for 4 h. It was cooled to room temperature, added into 50 mL of ice-water, filtered, washed by water, and dried to leave a yellow solid (1.60 g, 76%). The analytical sample was obtained by crystallization (DMF/H$_2$O=4:1), mp>250° C. $^1$H NMR (CDCl$_3$+DMSO-d$_6$), 3.176 (d, 2, J=5.7), 6.615 (d, 1, J=8.4), 6.887 (dd, 1, J=2.4, 8.6), 7.302 (d, 1, J=2.4), 8.025 (mb, 1) 9.849 (s, 1). MS, 210 (100, M$^+$), 181 (95), 153 (90). High resolution MS, Calcd for C$_9$H$_7^{35}$ClN$_2$O$_2$ 210.0192, found 210.0180.

Example 21

Preparation of 6,8-Dichloro-2,3,5-trihydro-1H,4H-1,4-benzodiazepine-2,5-dione (73c).

Compound 39c was prepared in a manner similar to 39a. From 139 mg (0.598 mmol) of 21c and 45.7 mg (0.608 mmol) of glycine there was obtained 64 mg of pale yellow solid, mp 250° C. $^1$H NMR (CDCl$_3$+DMSO-d$_6$) 3.3 (mb, 2) 6.790 (d, 1, J=1.6), 6.911 (d, 1, J=1.6), 8.22 (mb, 1), 10.021 (s, 1). MS, 244 (80, M$^+$), 215 (78), 187 (100), 160 (70). High resolution MS, Calcd for C$_9$H$_6^{35}$Cl$_2$N$_2$O$_2$ 243.9802, found 243.9790.

Example 22

Preparation of (R)-3-Benzyl-2,3,5-trihydro-1H, 4H-1,4-benzodiazepine-2,5-dione (58a).

Compound 58a was prepared in a manner similar to 73b. From 1.63 g (10.0 mmol) of isatoic anhydride and 1.65 g (10.0 mmol) of D-phenylalanine there was obtained after purification 240 mg (9%) of white solid, mp 248° C. $^1$H NMR (DMSO-d$_6$), 2.837 (dd, 1, J=14.1, 9.6), 3.115 (dd, 1, J=14.4, 4.8), 3.878 (m, 1), 7.087 (d, 1, J=8.1), 7.168–7.317 (m, 6), 7.498 (t, 1, J=7.5), 7.650 (d, 1, J=8.4), 8.510 (d, 1, J=6.0), 10.415 (s, 1).

Example 23

Preparation of (S)-3-Benzyl-2,3,5-trihydro-1H,4H-1,4-benzodiazepine-2,5-dione (58b).

Compound 67b was prepared in a manner similar to 39a. From 1.63 g (10.0 mmol) of isatoic anhydride and 1.65 g (10.0 mmol) of L-phenylalanine there was obtained after purification 250 mg (9%) of white solid. $^1$H NMR (DMSO-d$_6$), 2.836 (dd, 1, J=13.8, 9.3) 3.115 (dd, 1, J=13.8, 9.3), 3.679 (m, 1), 7.086 (d, 1, J=8.1), 7.168–7.317 (m, 6), 7.489 (t, 1, J=7.5), 7.650 (d, 1, J=7.5), 8.511 (d, 1, J=60), 10.415 (s, 1).

Example 24

Preparation of 6-Acetamido-4-hydroxy-4,3-boraza-2-quinolone (25a).

To a stirring mixture of 158 mg (0.754 mmol) of 5-acetamido-2-aminophenylboronic acid in 2 mL of acetic acid and 2 mL of ethanol under N: was added a solution of 150 mg (1.85 mmol) of KOCN in 1 mL of water. The mixture became a clear solution in one min and it was stirred for 5 h to produce a white precipitate. It was filtered, the solid was washed by water (3×1 mL), and dried to leave 104 mg of white solid. The filtrate was concentrated to less than 4 mL to give more precipitate which was filtered and dried to provide 46 mg (combined yield 150 mg, 92%) of 25a as a white solid. $^1$H NMR (DMSO-d$_6$), 1.996 (s, 3), 6.933 (d, 1, J=8.62), 7.512 (dd, 1, J=1.95, 8.78), 7.668 (s, 1), 7.912 (d, 1, J=1.72), 8,631 (s, 1), 9.773 (s, 1), 9.953 (s, 1). The analytical sample was obtained by crystallization (DMSO/

Example 25

Preparation of 6-Acetamido-4-hydroxy-3-methyl-4,3-boraza-2-quinolone (25b).

A solution of 40.5 mg (0.227 mmol) of 5-acetamido-2-aminophenylboronic acid and 0.1 mL of methyl isocyanate in 10 mL of dioxane was stirred at 25° C. for 6 h. The resulting precipitate was filtered, washed by dioxane (1 mL) and dried to leave 40.2 mg (76%) of 25b as an almost colorless solid. $^1$H NMR (DMSO-$d_6$), 2.000 (s, 3), 2.973 (s, 3), 6.942 (d, 1, J=8.6), 7.472 (dd, 1, J=1.8, 8.6), 7.993 (d, 1, J=1.8), 9.188 (s, 1), 9.759 (s, 1), 10.170 (s, 1). The analytical sample was obtained by crystallization (DMSO/$H_2O$) to give needles, mp>250° C. Anal. Calcd for $C_{10}H_{12}BN_3O_3$ 0.2 $H_2O$: C, 50.76; H, 5.28; N, 17.75. Found, C, 50.88; H, 5.29; N, 17.66. The structure was determined by X-ray crystallography.

Example 26

Preparation of 6-Acetamido-4-hydroxy-3-benzyl-4,3-boraza-2-quinolone (25c).

Compound 25c was prepared in a manner similar to compound 25b. From 43 mg (0.20 mmol) of 5-acetamido-2-aminophenylboronic acid and 0.1 mL of benzyl isocyanate in 8 mL of dioxane there was obtained 29 mg (46%) of 25c as an almost colorless solid, mp>250° C. $^1$H NMR (DMSO-$d_6$), 2.010 (s, 3), 4.769 (s, 2), 6.975 (d, 1, J=8.7), 7.179–7.299 (m, 5) 7.487 (dd, 1, J=1.5, 8.7), 8.040 (s, 1), 9.632 (s, 1), 9.784 (s, 1), 10.225 (s, 1).

Example 27

Preparation of 6-Acetamido-4,4-dihydroxy-3,3-dimethyl-4,3-boraza-2-quinolone (26a).

To a solution of 82 mg of 5-acetamido-2-aminophenylboronic acid in 2 mL of dry pyridine was added 0.3 mL of N,N-dimethylcarbamyl chloride. The solution was stirred at 25° C. overnight, then 0.1 mL of water was added and it was stirred for 2 h. The solution was evaporated to leave a red oil which was further dried under vacuum (0.05 mm) for 2 days. To the residue oil was added 0.5 mL of water followed by 2 mL of isopropanol to produce a precipitate. The mixture was filtered, the solid was washed by isopropanol (4×2.5 mL) and dried to leave 89 mg (87%) of 26a as a pale-yellow solid. $^1$H NMR ($D_2O$), 2.164 (s, 3), 3.138 (s, 3), 7.031 (d, 1, J=8.98), 7.324 (m, 2). The analytical sample was obtained by crystallization ($H_2O$/isopropanol) to give an almost colorless solid, mp>250° C. Anal. Calcd for $C_{11}H_{16}BN_3O_4$ $H_2O$: C, 46.67; H, 6.40; N, 14.48. Found, C, 46.45; H, 6.40; N, 14.55.

Example 28

Preparation of 2,3,4,5-tetrahydro-1H-Benzazepine-2,5-dione (42).

To 10 mL of $H_2SO_4$ (97%) cooled in an ice-bath was added portionwise 1.08 g (6.86 mmol) of 1,4-naphthoquinone and it was stirred to become a solution. To the red solution was added portionwise 0.454 g (6.98 mmol) of $NaN_3$. The mixture was stirred in ice bath for 2 h, then at room temperature for 2 days. It was added dropwise into 100 mL of ice-water and stirred for 1 h and allowed to stand overnight. The mixture was filtered and washed thoroughly by water, dried to leave brown solid 1.02 g. $^1$H NMR ($CDCl_3$+DMSO-$d_6$) shows it is more than 80% pure. Portion of the solid was crystallized (DMSO/$H_2O$) to give 32 as a brown solid, mp 225°–226° C. $^1$H NMR ($CDCl_3$+DMSO-$d_6$) 6.544 (d, 1, J=12.9), 6.657 (d, 1, J=12.9), 6.978 (t, 1, J=7.5), 7.152 (d, 1, J=8.4), 7.323 (t, 1, J=7.5), 7.812 (d, 1, J=8.1), 10.55 (bs, 1).

Example 29

Preparation of 1H-6H-1,6-Benzodiazocine-2,5-dione (43).

To 75 mL of $H_2SO_4$ (97%) cooled ice-bath was added portionwise 10 g (63.3 mmol) of 1,4-naphthoquinone and it was stirred for 10 min, followed by addition portionwise of 6.4 g (98.5 mmol) of $NaN_3$. The mixture was stirred in an ice bath for 4 h, then at room temperature for 2 days. It was added dropwise into 1000 mL of ice-water and allowed to stand overnight. The mixture was filtered, washed thoroughly by water, and dried to leave brown solid (9.2 g). A portion of the solid was crystallized by ethanol to give a solid, mp 245°–246° C. (dec.). $^1$H NMR ($CDCl_3$+DMSO-$d_6$), 5.761 (s, 2), 6.9 (m, 4), 9.268 (s, 2). MS, 188 (35, M$^+$), 170 (70), 144 (100), 119 (75). High resolution MS, Calcd for $C_{10}H_8N_2O_2$ 188.0581, found 188.0582.

Example 30

Preparation of 2,3,4,5-tetrahydro-1H-4-Oximino-benzazepine-2,3,5-trione (41).

A mixture of 188 mg (1.00 mmol) of 2,5-dihydro-2,5-dioxo-3-hydroxy-1H-benzazepine with 182 mg (2.63 mmol) of $NaNO_2$ in 6 mL of 0.1N NaOH was stirred for 1 h. To the mixture was added dropwise 2 mL of 2M $H_2SO_4$ and the mixture was stirred for 3 h. To the mixture was added a solution of 181 mg of $NaNO_2$ in 2 mL of water and it was stirred overnight. The mixture was treated with a solution of 100 mg of $NaNO_2$ in 0.5 mL of water once everyday for a week. It was filtered, washed by water, and dried to leave a solid (149 mg), mp 196°–197° C. (dec.). $^1$H NMR (DMSO-$d_6$), 7.16–7.23 (m, 4), 7.551 (t, 1, J=7.5), 7.956 (d, 1, J=7.8), 10.487 (s, 1) 12.004 (s, 1 ). $^1$H NMR (DMSO-d6+D2O), 7.168–7.216 (m, 2), 7.546 (t, 1, J=7.5), 7.953 (d, 1, J=8.1). MS, 218 (20, M$^+$), 173 (30), 146 (100), 119 (40). High resolution MS, Calcd for $C_{10}H_6N_2O_4$ 218.0327, found 218.0330.

Example 31

Preparation of 6,7-Dichloro-3-phenylquinoxaline-2-one.

A mixture of 528 mg (2.98 mmol) of 4,5-dichloro-1,2-phenylenediamine and 448 mg (2.98 mmol) of benzoylformic acid in 8 mL of ethanol was refluxed overnight. It was filtered, washed by water, and dried to leave 760 mg (87%) of solid. $^1$H NMR (DMSO-d$_6$), 7.465–7.536 (m, 4), 8.088 (s, 1), 8.256–8.282 (m, 2) 12.683 (s, 1).

Example 32

Preparation of 2,3-Dihydroindole-2-one-3-acetic acid (31).

To a solution of 1.77 g (10.1 mmol) of indole-3-acetic acid in 7 mL of DMSO was added dropwise 16 mL of concentrated HCl (10 min.). The solution was stirred at room temperature for 30 min after addition of the HCl and poured into 100 mL of water. It was extracted by ethyl acetate (5×50 mL) and the extract was dried and evaporated to leave a mixture of solid and liquid. The mixture was stirred with 10 mL of ethyl acetate and 30 mL of ether, filtered, washed by ether, and dried to leave 680 mg (36%) of pale-red solid. $^1$H NMR (DMSO-d$_6$), 2.682 (dd, 1, J=16.8, 7.0), 2.883 (dd, 1, J=16.8, 4.5), 3.603 (m, 1), 6.793 (d, 1, J=7.8), 6.904 (t, 1, J=7.5), 7.134 (d, 1, J=7.4), 7.191 (t, 1, J=7.2), 10.354 (s, 1), 12.12 (bm, 1).

Example 33

Preparation of 6-Nitrobenzoyleneurea

6-Nitrobenzoyleneurea was prepared using an adaptation of the method of Cheeseman, G. W. H., *J. Chem. Soc.* 1171 (1962). To a solution of benzoyleneurea (0.201 g, 1.24 mmol) in 3.0 mL concentrated H$_2$SO$_4$ at 0° C. was added KNO$_3$ (0.139 g, 1.37 mmol) in one portion. The reaction mixture was allowed to warm to room temperature then stirred overnight. The resulting yellow solution was poured onto 10 mL of ice giving a pale yellow precipitate. The precipitate was isolated on a Hirsch funnel and washed with 35 mL of deionized water. The solid was suspended in 25 mL deionized water, refiltered via Hirsch funnel and allowed to dry on the filter under vacuum for 30 minutes affording 0.155 g (60%) title compound as a pale yellow powder. An analytical sample was obtained by recrystallization from 50% glacial acetic acid as a pale brown microcrystalline solid: mp 327°–328° C. (lit., Varma and Singh; *Ind. J. Chem.* 296:578–81 (1990): 315°–316° C. dec.). FT-IR (cm$^{-1}$) 3020, 2850, 1713, 1684, 1631, 1602, 1538, 1491, 1444, 1385, 1332, 1303, 1239, 1157. $^1$H NMR (DMSO-d$_6$ at δ2.49): δ7.30 (d, J$_{8,7}$=9 Hz, 1 H, H8); 8.44 (dd, J$_{7,8}$=9 Hz, J$_{7,5}$=2.4 Hz, 1H, H7); 8.57 (d, J$_{5,7}$=2.7 Hz, 1H, H5); 11.71 (s, 1H, NH); 11.76 (s, 1H, NH). EIMS m/z 207 (M$^+$, bp), 164 (43%), 134 (18%), 106 (22%), 90 (29%), 63 (27%). EIHRMS calc. for C$_8$H$_5$N$_3$O$_4$ 207.02799, found 207.02910.

Example 34

Preparation of 6,8-Dinitrobenzoyleneurea 6,8-Dinitrobenzoyleneurea was prepared using an adaptation of the method of Cheeseman, G. W. H. *J. Chem. Soc.* 1171 (1962). To a solution of benzoyleneurea (0.205 g, 1.27 mmol) in 2.0 mL concentrated H$_2$SO$_4$ at 0° C. was added KNO$_3$ (0.324 g, 3.20 mmol) in one portion. The reaction mixture was allowed to warm to room temperature then stirred overnight. The resulting yellow solution was poured onto 10 mL ice giving a white precipitate. The precipitate was isolated on a Hirsch funnel and washed with 50 mL of deionized water. The solid was suspended in 50 mL of fresh deionized water and the precipitate was isolated again on a Hirsch funnel and dried in a drying pistol over refluxing ethanol [0.005 mmHg] for 1.5 hrs affording 0.285 g (89%) of the title compound as a white powder: mp 262°–264° C. (lit., Varma and Singh; *Ind. J. Chem.* 296:578–81 (1990): 263°–265° C.). FT-IR (cm$^{-1}$): 3458, 3311, 3179, 3097, 1736, 1701, 1630, 1604, 1548, 1503, 1472, 1401, 1350, 1310, 1274, 1173. $^1$H NMR (DMSO-d$_6$ at δ2.49): δ 8.82 (d, J$_{5,7}$=2.4 Hz, 1H, H5); 9.03 (d, J$_{7,5}$=2.7 Hz, 1H, H7); 10.98 (s, NH); 12.23 (s, NH). EIMS m/z 252 (M$^+$, bp) 222 (7%), 209 (14%), 179 (7%), 62 (7%), 45 (7%). EIHRMS calc. for C$_8$H$_4$N$_4$O$_6$, 252.01306 found 252.01300.

Example 35

Preparation of 6-Chlorobenzoyleneurea.

6-Chlorobenzoyleneurea was prepared using an adaptation of the method of Mitchell, et al., *J. Org. Chem.* 44:4733 (1979). To a mixture of benzoyleneurea (0.225 g, 1.39 mmol) in 5.0 mL DMF was added NCS (0.187 g, 1.40 mmol) in one portion. A clear colorless solution resulted after 30 minutes of magnetic stirring, and this solution was allowed to stir at room temperature overnight. The resulting clear colorless reaction solution was poured into 30 mL water rendering a white solid precipitate. The white solid was isolated on a Hirsch funnel and washed with 40 mL water. The white powder was twice recrystallized from glacial acetic acid. The resulting white prisms were suspended in 50 mL water, isolated on a Hirsch funnel, washed with water and then dried in a drying pistol over refluxing ethanol [0.001 mmHg] affording 0.061 g (22%) of title compound: mp 309°–320° C. subl. FT-IR (cm$^{-1}$) 3431, 3188, 1750, 1706, 1669, 1619, 1488, 1400, 1375, 1288, 1144. $^1$H NMR (DMSO-d$_6$ at δ 7.17 (d, J$_{8,7}$=8.7 Hz, 1H, H8); 7.68 (dd, J$_{7,8}$=9 Hz, J$_{7,5}$=2.4 Hz, 1H, H7); 7.80 (d, 1H, H5); 11.28 (s, 1H, NH); 11.44 (s, 1H, NH). EIMS m/z 196 (M$^+$, bp) 155 (75%), 125 (26%), 63 (23%). EIHRMS calc. for C$_8$H$_5$ClN$_2$O$_2$ 196.00395, found 196.00500.

Example 36

Preparation of 6-Chloro-8-nitrobenzoyleneurea.

6-Chloro-8-nitrobenzoyleneurea was prepared using an adaptation of the method of Cheeseman, G. W. H. *J. Chem. Soc.* 1171 (1962). To a clear colorless solution of 6-chlorobenzoyleneurea (0.029 g, 0.147 mmol) in 0.30 mL concentrated H$_2$SO$_4$ at 0° C. was added KNO$_3$ (0.018 g, 0.176 mmol) in one portion. The yellow solution was stirred at 0° C. for 20 minutes and then allowed to warm to room temperature and stirred overnight. The resulting yellow reaction solution was poured onto 2.5 g ice giving a light yellow solid precipitate. The solid was isolated on a Hirsch funnel and washed with 20 mL of deionized water. The solid was recrystallized from glacial acetic acid and the resulting light yellow powder was dried in a drying pistol over refluxing ethanol [0.01 mmHg] for 2 h affording 0.021 g (60%) of the title compound: mp 234°–236° C. FT-IR (cm$^{-1}$) 3323, 3190, 3090, 1756, 1709, 1696, 1629, 1536, 1490, 1463, 1344, 1284. $^1$H NMR (DMSO-d$_6$ at δ 2.49): δ 8.24 (d, J$_{5,7}$=2.4 Hz, 1H, H5); 8.52 (d, J$_{7,5}$=2.4 Hz, 1H, H7); 10.4–10.6 (br s, NH); 11.8–12.1 (bs, NH). EIMS m/z 241

($M^+$, bp) 198 (44%), 154 (23%), 124 (25%), 96 (45%), 87 (24%), 62 (15%). EIHRMS calc. for $C_8H_4ClN_3O_4$ 240.989021, found 240.989000.

Example 37

Preparation of 6,8-Dibromobenzoyleneurea 6,8-Dibromobenzoyleneurea was prepared using an adaptation of the method of Cheeseman, G. W. H. *J. Chem. Soc.* 1171 (1962). To a mixture of benzoyleneurea (0.227 g, 1.397 mmol); $Ag_2SO_4$ (0.439 g, 1.407 mmol) and 5.60 mL concentrated $H_2SO_4$ was added dropwise liquid $Br_2$ (0.20 mL, 0.620 g, 3.88 mmol). The resulting milky emulsion was allowed to magnetically stir at room temperature overnight. The reaction mixture was poured into 50 mL ice and the grey solid isolated on a Hirsch funnel. The solid was suspended in 25 mL boiling glacial acetic acid and its insoluble portion removed via a hot filtration. The hot filtrate was collected and the glacial acetic acid boiled away to give a white powdery solid. The white solid was four times recrystallized from glacial acetic acid and the resulting white prisms dried in a vacuum oven at 60° C. for 96 h affording 0.024 g (5%) of the title compound: mp 289°–291° C. FT-IR (cm$^{-1}$) 3444, 3169, 3119, 3063, 1719, 1681, 1606, 1488, 1406, 1363, 1306. $^1$H NMR (DMSO-$d_6$ at δ 2.49): δ 7.96 (d, $J_{5,7}$=2.1 Hz, 1H, H5); 8.17 (d, $J_{7,5}$=2.1 Hz, 1H, H7); 10.49 (s, NH); 11.61 (s, NH).

In the following Examples 38–40, all reactions were run under a nitrogen atmosphere. Reagents were used as received unless otherwise indicated. Melting points were determined in open capillary tubes on a Mel-Temp apparatus and are uncorrected. A preheated block was employed to minimize decomposition when the melting points were greater than 250° C. DMF was dried over molecular sieves and all other solvents were reagent grade unless otherwise stated.

$^1$H NMR spectra were recorded on a 300 MHz General Electric QE-300 and chemical shifts are reported in ppm (δ) relative to the residual proton signals of the deuterated solvents (CHCl$_3$, δ7.26; CD$_2$HSOCD$_3$, δ2). $^{13}$C NMR spectra were run at 75 MHz. IR spectra were recorded as absorbance in wavenumbers (cm$^{-1}$) with a Nicolet 5DXB FT-IR spectrometer using KBr pellets. UV spectra were recorded on a Perkin Elmer Lambda 6 UV/VIS spectrophotometer. MS were recorded on a VG ZAB-2-HF mass spectrometer with a VG-11-250 data system, in the electron ionization mode (70 eV) unless otherwise indicated.

Example 38

Preparation of 4-Bromo-5,6-dichloro-3,8-Dihydrocyclobuta[b]quinoxaline-1,2-dione.

3-Bromo-4,5-dichloro-2-nitroaniline. The procedure of Mitchell and Williams, *J. Org. Chem.* 44:4733 (1979) was modified to obtain the title compound. A mixture of 4,5-dichloro-2-nitroaniline (1.59 g, 7.68 mmol, Aldrich), DMF (30 mL, dist. at reduced pressure) and NBS (1.51 g, 8.48 mmol, Aldrich) was stirred at room temperature (25° C.) for two days. The dark brown solution was poured into deionized water (200 mL) and allowed to set for 30 minuets in. The mixture was filtered and the solids washed with deionized water giving 1.81 g (82.4%) of the crude bromide as a yellow powder. The powder was crystallized from ethanol/water (5:1) giving 1.74 g (79.2%) of the title compound as bright yellow needles, mp. 132°–4° C., pure by $^1$H NMR. $^1$H NMR (CDCl$_3$) 6.82 (s, 2H), 8.32 (s, 1H).

3-Bromo-4,5-dichloro-o-phenylenediamine. The procedure of Bellamy and Ou, *Tetrahedron Lett.* 25:839 (1984), was modified to obtain the title compound. A mixture of the nitroaniline (1.69 g, 5.91 mmol), absolute ethanol (35 mL) and SnCl$_2$.H2O (6.79 g, 30.1 mmol, Baker) were refluxed for 30 min. After cooling to room temperature, the reaction was poured into ice (30 g) and saturated NaHCO$_3$ was added to adjust the pH to 8 (70 mL). The mixture was extracted with ethyl acetate (3×50 mL) and the combined extracts were washed with saturated NaCl (2×25 mL). The orange organic fraction was dried (MgSO$_4$), mixed with activated charcoal and the mixture was filtered through a bed of celite. The solids were washed with ethyl acetate (2×10 mL) and the combined light yellow filtrates were evaporated giving 1.36 g (89.9%) of a light yellow powder. The powder was crystallized from ethanol/water (3:4) giving 1.29 g (85.3%) of the title compound as creamy white needles, top. 128°–9° C., pure by $^1$H NMR. $^1$H NMR (CDCl$_3$, d) 3.49 (s, broad, 2H), 3.96 (s, broad, 2H), 6.78 (s, 1H).

5,6-Dichloro-3,8-dihydrocyclobuta[b]quinoxaline-1,2-dione. The procedure of Ehrhardt et al., *Chem. Bet.* 110:2506 (1977) was adapted to synthesize the title compound. Diethyl squarate (0.441 mL, 2.98 mmol, Aldrich) was dissolved in absolute ethanol (3 mL) and the solution was added via a drop funnel to a refluxing solution of 4,5-dichloro-o-phenylenediamine (480 mg, 2.71 mmol, Pfaltz & Bauer, 98%) in absolute ethanol (25 mL). The dark brown solution was refluxed (90°–100° C. oil bath) for three hours. The dark brown mixture was allowed to cool to room temperature and it was filtered giving 494 mg (71.5%) of a dark brown powder. The powder was triturated in boiling 1N NaOH, mixed with activated charcoal and filtered though a bed of celite. The brownish red filtrate was made acidic (pH 3) with 6N HCl (8.4 mL) causing a flocculent yellow precipitate to form. The mixture was centrifuged and the liquid decanted. The solids were mixed with 30 mL of deionized water, centrifuged and the liquid was decanted giving 54.5 mg (7.88%) of the crude product as a yellowish orange powder. The powder was crystallized from DMSO giving 26.2 mg (3.28%) of the title compound as fine light orange needles, mp>360° C., pure by $^1$H NMR. IR (KBr, cm$^{-1}$) 3148 (NH), 1792 (CO), 1685 (CO), 1675 (C=C), 1607 (NH). $^1$H NMR (DMSO-$d_6$, δ) 6.35 (s, 2H), 10.19 (s, 2H). $^{13}$C NMR (DMSO-$d_6$, δ) 116.85, 125.87, 132.62, 174.31, 178.42 (CO). UV (DMSO) $\lambda_{max}$ 225 nm, ε 35,000. HRMS calcd. for $C_{10}H_4N_2O_2Cl_2$ 253.9650, found 253.9655.

4-Bromo-5,6-dichloro-3,8-dihydrocyclobuta[b]quinoxaline-1,2-dione. The procedure of Ehrhardt et al., *Chem. Ber.* 110:2506 (1977) was adapted to synthesize the title compound. A solution of diethyl squarate (351 mg, 2.06 mmol, Aldrich), and 4-Bromo-5,6-dichlorophenylene-1,2-diamine (520 mg, 2.03 mmol) in absolute ethanol (15 mL) was stirred for one day at room temperature (25° C.). The ethanol was distilled (105° C. oil bath) from the mixture and the dark brown residue was triturated in boiling ethanol (15 mL). After cooling to room temperature, the mixture was filtered giving 460 mg (67.9%) of a green powder. The crude cyclobutaquinoxalinedione was triturated in hot 1N NaOH (20 mL), mixed with activated charcoal and the mixture was filtered though a bed of celite. The solids were washed with 1N NaOH (5 mL) and the combined filtrates (intense red) were acidified to pH 3 (6N HCl, 2.5 mL). The resulting precipitate was filtered, washed with deionized water (2×5 mL) and dried giving 365 mg (53.8%) of an orange powder.

The powder was crystallized from DMSO/deionized water (5:3) giving 272 mg (40.1%) of 3 as brownish orange needles, mp>360° C., pure by $^1$H NMR. IR (KBr, cm$^{-1}$) 3137 (NH), 1795 (CO), 1696 (CO), 1590 (NH), 723 (CCl). $^1$H NMR (DMSO-d$_6$, δ): 6.38 (s, 1H), 9.75 (s, 1H), 10.34 (s, 1H). $^{13}$C NMR (DMSO-d$_6$, δ) 111.5, 115.4, 126.7, 126.8, 132.3, 133.8, 174.5, 175.0, 177.8, 179.2 (CO). HRMS calcd. for C$_{10}$H$_3$N$_2$O$_2$BrCl$_2$ 331.8755, found 331.8749.

Example 39

Preparation of
3,8-Dihydro-4,5,6-trichlorocyclobuta[b]quinoxaline-1,2-dione.

2-Nitro-3,4,5-trichloroaniline. The procedure of Mitchell and Williams, *J. Org. Chem.* 44:4733 (1979) was modified to obtain this compound. A mixture of 4,5-dichloro-2-nitroaniline (1.36 g, 6.57 mmol, Aldrich), DMF (30 mL, dist. at reduced pressure) and NBS (967 mg, 7.24 mmol, Eastman) was stirred at room temperature (25° C.) for two days. The dark brown solution was poured into deionized water (150 mL) and allowed to set for 30 min. The mixture was filtered and the solids washed with deionized water giving 1.51 g (95.1%) of the crude bromide as a yellow powder. The powder was crystallized from ethanol/water (5:1) giving 1.42 g (89.4%) of the title compound as bright yellow needles, top. 135°–6° C., pure by $^1$H NMR. 1H NMR (CDCl3, d) 6.71 (s, broad, 2H), 8.27 (s, 1H).

3,4,5-Trichloro-o-phenylenediamine. The procedure of Bellamy and Ou, *Tetrahedron Lett.* 25:839 (1984) was modified to obtain the title compound. A mixture of the nitroaniline (1.37 g, 5.67 mmol), absolute ethanol (35 mL) and SnCl$_2$.H$_2$O (6.42 g, 28.5 mmol, Baker) were refluxed for 30 min. After cooling to room temperature, the reaction was poured into ice (20 g) and saturated NaHCO$_3$ was added to adjust the pH to 8 (65 mL). The mixture was extracted with ethyl acetate (3×50 mL) and the combined extracts were washed with saturated NaCl (2×20 mL). The orange organic fraction was dried (MgSO$_4$), mixed with activated charcoal and the mixture was filtered through a bed of celite. The solids were washed with ethyl acetate (2×10 mL) and the combined light yellow filtrates were evaporated giving 1.16 g (96.7%) of a creamy white powder. The powder was crystallized from ethanol/water (2:3) giving 1.09 g (90.9%) of the title compound as creamy white needles, mp. 109°–11° C., pure by $^1$H NMR. $^1$H NMR (CDCl$_3$, δ) 3.48 (s, broad, 2H), 3.87 (s, broad, 2H), 6.74 (s, 1H).

3,8-Dihydro-4,5,6-trichlorocyclobuta[b]quinoxaline-1,2-dione. The procedure of Ehrhardt et al., *Chem. Ber.* 110:2506 (1977), was adapted to synthesize the title compound. A solution of diethyl squarate (411 mg, 2.41 mmol, Aldrich), and 4,5,6-trichlorophenylene-1,2-diamine (492 mg, 2.33 mmol) in absolute ethanol (15 mL) was stirred for one day at room temperature (25° C.). The ethanol was distilled (105° C. oil bath) from the mixture and the dark brown residue was triturated in boiling ethanol (15 mL). After cooling to room temperature, the mixture was filtered giving 434 mg (64.3%) of a dark green powder. The crude cyclobutaquinoxalinedione was triturated in hot 1N NaOH (20 mL), mixed with activated charcoal and the mixture was filtered though a bed of celite. The solids were washed with 1N NaOH (5 mL) and the combined filtrates (deep red) were acidified to pH 3 (6N HCl, 2.5 mL). The resulting precipitate was filtered, washed with deionized water and dried giving 263 mg (39.0%) of a yellow powder. The powder was crystallized from DMSO/deionized water (3:1) giving 224 mg (33.3%) of the title compound as fine yellow microneedles, mp>360° C., pure by $^1$H NMR. IR (KBr, cm$^{-1}$) 3143 (NH), 1801 (CO), 1690 (CO), 1602 (NH). $^1$H NMR (DMSO-d$_6$, δ): 6.29 (s, 1H), 10.00 (s, 1H), 10.37 (s, 1H). $^{13}$C NMR (DMSO-d$_6$, δ): 114.9, 120.1, 125.2, 127.2, 131.1, 133.7, 174.7, 174.9, 178.0, 179.3 (CO).

Example 40

Preparation of
4-Chloro-3,8-dihydro-6-trifluoromethylcyclobuta[b]quinoxaline-1,2-dione.

The procedure of Ehrhardt et al., *Chem. Ber.* 110:2506 (1977) was adapted to synthesize the title compound. A solution of diethyl squarate (430 mg, 2.53 mmol, Aldrich), and 3-chloro-5-trifluoromethyl-1,2-phenylenediamine (530 mg, 2.52 mmol, Maybridge) in absolute ethanol (7.5 mL) was stirred for two days at room temperature (25° C.). The ethanol was distilled (120° C. oil bath) from the mixture and the dark brown residue was triturated in boiling ethanol (15 mL). After cooling to room temperature, the mixture was filtered giving 338 mg (45.5%) of dark green crystals. The crude cyclobutaquinoxalinedione was dissolved in DMSO (15 mL), mixed with activated charcoal and filtered though a bed of celite giving an orange solution. Deionized water was added to the filtrate (15 mL) and the resulting orange precipitate was redissolved by heating. The resulting crystals were recrystallized from DMSO/deionized water (1:1) giving 173 mg (23.8%) of the title compound as fine orange prisms, mp 335°–7° C., pure by $^1$H NMR. IR (KBr, cm$^{-1}$) 3155 (NH), 1807 (CO), 1696 (CO), 1672 (C=C), 1619 (NH), 676 (CCl). $^1$H NMR (DMSO-d$_6$, δ): 6.33 (s, 1H), 7.06 (s, 1H), 10.01 (s, 1H), 10.33 (s, 1H). $^{13}$C NMR (DMSO-d$_6$, δ): 110.4, 120.5, 122.9, 125.2, 125.6, 134.1, 135.6, 175.3, 175.5, 177.9, 179.6 (CO). UV (DMSO) λ=261 nm, ε=27,000.HRMS calcd. for C$_{11}$H$_4$N$_2$O$_2$ClF$_3$ 287.9913, found 287.9921.

Example 41

Preparation of 4,6-dimethylisatin.

The procedure of Varma and Singh, Ind. *J. Chem.* 296:578–81 (1990), was adapted. To a solution of tribromoacetaldehyde CBr$_3$CHO (6.80 g, 24 mmol, Aldrich) in water (60 mL) and 1N HCl (2 mL) was added successively sodium sulfate (6.20 g, 43 mmol), a solution of 3,5-dimethylaniline (2.54 g, 21 mmol) in 1N HCl (40 mL), and a solution of hydroxyamine hydrochloride (5.50 g, 79 mmol) in water (25 mL). The mixture was heated to vigorous boiling and kept boiling for 10 min then cooled in ice bath to room temperature. It was filtered, washed by water, dried to leave pale yellow solid. The solid was added portionwise into concentrated H$_2$SO$_4$ (50 mL) kept at 50° C. After the addition, the solution was heated to 80° C. for 15 min. It was cooled to room temperature, and added into ice water (450 mL). After standing for 0.5 h, it was filtered and washed with water and dried to leave a yellow solid. The solid was boiled with ethyl acetate (180 mL), filtered and cooled to room temperature. The crystalline solid was collected and dried to give the title compound (752 mg, 20%) containing a 2% impurity by NMR. Recrystallization from DMSO/H$_2$O afforded pure title compound as needles: mp 220°–2° C. IR (KBr, cm$^{-1}$) 3439, 3211, 1762, 1729, 1628. $^1$H NMR (DMSO-d$_6$): δ2.821 (s, 3H); 2.380 (s, 3H); 6.517 (s, 1H); 6.673 (s, 1H); 10.931 (s, 1H). LRMS: calcd for C$_{10}$H$_9$NO$_2$ m/z: 175; found: 175. Purity: >97.4% by HPLC.

Example 42

Synthesis of 4,6-dimethyl-5-nitroisatin.

The method of Cheesman, G. W. H.; *J. Chem. Soc.* 1170 (1962), was adapted. 4,6-Dimethylisatin (89 mg, 0.50 mmol) was dissolved in concentrated $H_2SO_4$ (1.0 mL) at 0° C. for 30 min with stirring, then $KNO_3$ (55 mg, 0.55 mmol, Baker) was added to this solution. The mixture was stirred at 25° C. for 24 h. It was then poured into ice water (5 g). The resulting precipitate was collected by filtration. The precipitate was dissolved in 1N KOH (5 mL) and the small amount of solid was removed by filtration, then the filtrate was acidified to pH 2 with 4N HCl (~1 mL) to give a yellow precipitate. The solid was collected by filtration and was washed with water (2×1 mL), then it was dried in the air at 50° C. for 4 h affording pure (by NMR) title compound (85 mg, 77%) as a yellow powder. Crystallization from acetone/water gave crystals. Mp 278°–80° C. (dec.). IR (KBr, $cm^{-1}$): 3452, 3225, 2931, 1780, 1742, 1635, 1608, 1535. $^1H$ NMR (DMSO-$d_6$): δ 11.357 (s, 1H), 6.771 (s, 1H), 2.389 (s, 3H), 2.305 (s, 3H). Purity >97.5% by HPLC.

Example 43

Synthesis of 5,7-Dimethyl-2,3,4-trihydroxyquinoline.

The procedure of Baker and Almaula, *J. Org. Chem.* 27:4672–74 (1962), was adapted. A mixture of 5,7-dimethylquinoline-2,3,4-trione-3-oxime (45 mg, 0.21 mmol) and 30% Pd/C (10 mg) in DMF (2 mL) and 4N HCl (2 mL) was hydrogenated at 50 psi for 12 h. A crystalline colorless solid was observed in the reaction mixture. The mixture was filtered and the solid was stirred with acetone/methanol (1:1) and filtered to remove the black catalyst. The acetone/methanol solution was added into the 1N HCl solution (10 mL) to give white crystals. It was filtered and washed with water (1×1 mL), and dried to leave 21 mg of the title compound (50%), which is pure by NMR. mp 280°–2° C. IR (KBr, $cm^{-1}$): 3452, 3178, 3108, 1663, 1621, 1585. $^1H$ NMR (DMSO-$d_6$): δ 2.248 (s, 3H); 2.638 (s, 3H); 6.704 (s, 1H); 6.876 (s, 1H); 8.595 (s, 1H); 9.542 (s, 1H); 11.424 (s, 1H). HRMS: calcd for $C_{11}H_{11}NO_3$ m/z: 205.0738; found: 205.0729. Purity:>99% by HPLC (tautomers 71.5% and 28.4%).

Example 44

Synthesis of 5,7-dimethyl-4,1-benzoxazine-2,3-dione.

The method of Mohiuddin et al. *Ind. J. Chem.* 24B:905–7 (1985), was adapted. To a solution of $K_2S_2O_8$ (270 mg, 1 mmol, Aldrich) in $H_2SO_4$ (98%, 1 mL) in ice bath was added in one portion 4,6-dimethylisatan (120 mg, 0.68 mmol). The mixture was stirred in ice bath for 10 min to become a solution. To the solution was added ice water (1 mL) and the mixture was stirred for 10 min. The mixture was filtered, washed by ice water, and dried to leave brown solid (87 mg, 67%) of reasonable quality but with a 5% impurity by NMR. Recrystallization from DMSO/water gave 46 mg of pure title compound: mp 222°–4° C. IR (KBr, $cm^{-1}$) 3438, 3200, 1754, 1733, 1628, 1277. $^1H$ NMR (DMSO-$d_6$): δ 2.285 (s, 3H); 2.381 (s, 3H); 6.518 (s, 1H); 6.674 (s, 1H); 10.924 (s, 1H). HRMS: calcd for $C_{10}H_9NO_3$ m/z: 191.0582; found: 191.0589.

Example 45

Synthesis of 5,7-dimethylisatoic anhydride.

To a mixture of 4,6-dimethylisatan (175 mg, 1 mmol) in acetic acid (2 mL) with one drop $H_2SO_4$ was added dropwise 30% $H_2O_2$ (0.2 mL). The mixture was heated at 70°–80° C. for 2 h with stirring and cooled to room temperature and crystals came out. It was filtered and washed by water and dried to leave the title compound (37 mg, 20%) as yellow crystals: mp 270°–72° C. IR (KBr, $cm^{-1}$): 3459, 3165, 1768, 1719, 1375. $^1H$ NMR (DMSO-$d_6$): δ 11.810 (s, 1H), 6.793 (s, 1H), 6.703 (s, 1H), 2.490 (s, 3H), 2.229 (s, 3H). HRMS: calcd. for $C_{10}H_9NO_3$ m/z: 191.0582, found: 191.0597.

In the following examples 46–51, reagents were used as received unless otherwise indicated. Melting points were taken on a Mel-Temp melting point apparatus and are uncorrected. Samples were placed in the block when the temperature was >250° C. in order to minimize decompositon prior to melting. Column chromatography was performed in the flash mode on Davisil silica gel (200–425 mesh), unless otherwise indicated. Analytical thin layer chromatography was performed on aluminum-backed silica gel 60 F254 plates and visualization was effected with an ultraviolet lamp. $^1H$ NMR spectra were recorded on a 300 MHz General Electric QE-300; chemical shifts are reported in delta units referenced to residual proton signals of the deuterated solvents ($CHCl_3$, δ 7.26; $CHD_2OD$, δ 3.30; $CH_3SOCH_2D$, δ 2.49; $CH_3COCH_2D$, δ 2.04. $^{13}C$ NMR spectra were run at 75 MHz. Infrared spectra were obtained on a Nicolet 5DXB FT-IR spectrometer. Absorptions recorded in wavenumbers ($cm^{-1}$) and the intensity of the absorptions are indicated by the letters s (strong), m (medium), and w (weak). Mass spectra were recorded on a VG ZAB-2-HF mass spectrometer with a VG-11-250 data system, in the electron ionization mode (70 eV) unless otherwise indicated. Microanalyses were performed by Desert Analytics of Tuscon, Ariz.

Example 46

Preparation of 5-chloro-6-fluoro-2-mercaptobenzimidazole.

The procedure of Van Allan and Deacon, *Org. Synth. Coll. Vol. IV*, 569, was adapted. A mixture of 1,2-diamino-4-chloro-5-fluorobenzene (528 mg, 3.29 mmol, Aldrich), potassium hydroxide (202 mg, 0.36 mmol), carbon disulfide (280 mg, 0.36 mmol), 95% ethanol (3 mL) and water (0.45 mL) was heated under reflux for 3 h. Activated charcoal (120 mg) was then added cautiously, and after the mixture has been heated at the refluxing temperature for 10 min the activated charcoal was removed by filtration. The filtrate was heated to 60°–70° C., warm water (3 mL) was added, and then acetic acid (0.25 mL) in water (0.5 mL) was added with good stirring for 4 h. The mixture was placed in a refrigerator overnight to give a mixture of brown and white crystals. The brown crystals were removed by washing with chloroform (5 mL). Recrystallization from hot EtOH/$H_2O$ gave pure title compound (420 mg, 63.5%, purity >99.57% by HPLC) as a white cubic crystals; top: 294°–6° C. (sub. from 250° C.). IR (KBr, $cm^{-1}$): 3443, 3131, 3075, 1618, 1506, 1487, 1462. $^1H$ NMR (DMSO-$d_6$): δ 7.169 (d, J=9 Hz, 1H); 7.245 (d, J=6.6 Hz, 1H); 12.758 (s, 2H). HRMS: calcd for $C_7H_4ClFN_2S$ ($M^+$) m/z: 201.9766, Found: 201.9779.

Example 47

Preparation of 5-bromo-2-hydroxybenzimidazole

The procedure of Mitchell et at., *J. Org. Chem.* 44(25):4733 (1979) was adapted. To a stirred suspension of 2-hydroxybenzimidazole (134 mg, 1.00 mmol, Aldrich) in dry DMF (3 mL) was added dropwise a solution of N-bromosuccinimide (187 mg, 1.05 mmol, Aldrich) in dry DMF (1 mL) and then it was stirred at 25° C. for 0.5 h resulting a light yellow solution. The solution was allowed to stand at 25° C. for 24 h to give a brown yellow solution which was poured into 20 mL ice water and collected by filtration and washed with distilled water (2×1 mL) followed by 95% ethanol (2×1 mL), affording 188 mg (88%) of crude title compound containing 5% dibromo-2-hydroxybenzimidazole by NMR. A 188 mg sample of crude product was dissolved into 1N NaOH (5 ml) and then acidified to pH=2 with 4N HCl giving a white creamy precipitate. It was collected by filtration and washed with distilled water (2×1 mL) followed by 95% ethanol (2×1 mL) and dried in the air at 50° C. for 8 h, giving 180 mg of title compound (containing 4% di-bromo-2-hydroxybenzimidazole by NMR) as a white powder. Crystallization from hot methanol gave white microcrystals of purer title compound (containing 3% di-bromo-2-hydroxy-benzimidazole by NMR). Mp: 305°–7° C.; IR (KBr, cm$^{-1}$): 3425, 3181, 3012, 1756, 1693, 1481. $^1$H NMR (DMSO-d$_6$): δ 6.854 (d, J=8.1 Hz, 1H); 7.038–7.082 (m, 2H); 10.768 (s, 2H). HRMS: calcd for C$_7$H$_5$BrN$_2$O (M$^+$) m/z: 211.9584 found: 211.9591. Potency relative to DCK: 1%.

Example 48

Preparation of 5,6-dibromo-2-hydroxybenzimidazole

The procedure of Mitchell et al., *J. Org. Chem.* 44(25):4733 (1979), was adapted. To a stirred suspension of 2-hydroxybenzimidazole (134 mg, 1.00 mmol, Aldrich) in dry DMF (3 mL) was added dropwise a solution of N-bromosuccinimide (374 mg, 2.10 mmol, Aldrich) in dry DMF (1 mL) and stirred at 25° C. for 0.5 h resulting in a light yellow solution. The reaction was carried continually at 35° C. for 24 h to give a white precipitate which was collected by filtration then washed with distilled water (2×1 mL) followed by 95% ethanol (2×1 mL) affording 84 mg of pure title compound (by NMR) as a white powder. The filtrate was poured into 20 mL ice water and the precipitate was collected by filtration, then washed with distilled water (2×1 mL) followed by 95% ethanol (2×1 mL) affording 187 mg of title compound (with 1% impurity by NMR) which was dissolved into 1N NaOH (5 mL) and then acidified to pH=2 with 4N HCl giving a white creamy precipitate. It was collected by filtration and washed with distilled water (2×1 mL) followed by 95% ethanol (2×1 mL) and dried in the air at 50° C. for 8 h, giving 177 mg (total yield ~89%) of pure title compound (by NMR) as a white powder. Mp: sublimed from 320° C.; decomposed from 345° C., melted to brown liquid at 355°–8° C. IR (KBr, cm$^{-1}$): 3425, 3068, 2993, 1700, 1481. $^1$H NMR (DMSO-d$_6$): δ 7.218 (s, 2H), 10.901 (s, 2H). Purity:>97.17% by HPLC. Mass: calcd for C$_7$H$_4$Br$_2$N$_2$O (M$^+$) m/z: 289.8687 found: 289.8693. Potency relative to DCK: 1.30%

Example 49

Preparation of 5-nitro-6-bromo-2-hydroxybenzimidazole

The procedure of Cheesman, G. W. H., *J. Chem. Soc.* 1170 (1962), was adapted. To a stirred suspension of 5-bromo-2-hydroxybenzimidazole (105 mg, 0.49 mmol) in concentrated H$_2$SO$_4$ (1 mL) at 0° C. for 30 min was added KNO$_3$ (58.5 mg, 0.58 mmol, Baker) in one portion. The mixture was stirred at 0° C. for 3 h then at room temperature for one day. The mixture became a red solution. Then it was poured into ice (30 g) resulting in the separation of a brown precipitate, which was collected by filtration and washed with distilled water (2×1 mL) followed by ethanol (2×1 mL) to give 141 mg of crude title compound (contains minor impurities by NMR). Crystallization from DMSO/H$_2$O gave 103 mg of pure title compound (80.5%) as bright yellow needles: mp 290°–4° C. (dec.), changed color from 200° C. IR (KBr, cm$^{-1}$): 3406, 3181, 1712, 1537. $^1$H NMR (DMSO-d$_6$): δ 7.244 (s, 1H), 7.558 (s, 1H), 11.227 (s, 1H), 11.321 (s, 1H). HRMS: calcd for C$_7$H$_4$N$_3$O$_3$Br (M$^+$) m/z 256.9433; found: 256.9439.

Example 50

Preparation of 4-Nitro-5,6-dibromo-2-hydroxybenzimidazole

The procedure of Cheesman, G. W. H., *J. Chem. Soc.* 1170 (1962), was adapted. To a stirred suspension of 5,6-dibromo-2-hydroxybenzimidazole (140 mg, 0.48 mmol) in concentrated H$_2$SO$_4$ (1 mL) at 0° C. was added KNO$_3$ (58.5 mg, 0.56 mmol, Baker) in one portion. The mixture was stirred at 0° C. for 3 h then at room temperature for one day. The mixture became a blue solution. Then it was poured into ice (30 g) resulting in the separation of a bright yellow precipitate which was collected by filtration and washed with distilled water (2×1 mL) followed by ethanol (2×1 mL) to give 150 mg of crude title compound (90%) (contains minor impurities by NMR). Crystallization from DMSO/H$_2$O gave pure title compound as bright yellow microcrystals, mp 305°–308° C. (dec.). IR (KBr, cm$^{-1}$): 3412, 3143, 1712, 1537. $^1$H NMR (DMSO-d$_6$): δ 7.430 (s, 1H), 11.455 (s, 1H), 11.715 (s, 1H). HRMS: calcd for C$_7$H$_3$N$_3$O$_3$Br$_2$ (M$^+$) m/z: 334.8538; found 334.8540. Potency relative to DCK: inactive.

In the following Examples 51–55, all reactions were run under a nitrogen atmosphere. Reagents were used as received unless otherwise indicated. Melting points were taken on a Mel-Temp melting point apparatus and are uncorrected. Samples were placed in the preheated block in order to minimize decomposition prior to melting. Tetrahydrofuran (THF) was distilled from blue sodium benzophenone ketyl solution. Dimethylformamide (DMF) was distilled under reduced pressure (50 mmHg) and kept over molecular sieves. $^1$H NMR spectra were recorded on a 300 MHz General Electric QE-300; chemical shifts are reported in delta units referenced to residual proton signals of the deuterated solvents (CDCl$_3$, δ 7.260; DMSO-d$_6$, δ 2.490). $^{13}$C NMR spectra were run at 75 MHz. Infrared spectra were obtained on a Nicolet 5DXB FT-IR spectrometer. Mass spectra were recorded on a VG ZAB-2-HF mass spectrometer with a VG-11-250 data system in the electron ionization mode (70 ev) unless otherwise indicated.

Example 51

Preparation of 3-(Hydroxyimino)-1,4-dihydroquinoxalin-2-one

3-Aminoquinoxalin-2(1H)-one. An adaptation of the method of Burrell et al., *J. Chem. Soc. Perkin I.* 2707 (1973), was used. A mixture of 1,2-phenylenediamine (324 mg, 3.00 mmol; Aldrich Co.) and ethyl thiooxamate (400 mg, 3.00 mmol; Aldrich Co.) in 7.5 mL of ethanol was heated to reflux. The resulting solution was stirred under reflux for 3 h. The resulting suspension was cool to 25° C. A pale yellow precipitate appeared. The mixture was vacuum filtered and the solid was washed with EtOH (5×2 mL) and dried in vacuum at 60° C. overnight to yield 85 mg (18%) of 3-aminoquinoxalin-2(1H)-one as a pale yellow solid (McKillop et al., *Tetrahedron Lett.* 23:3357 (1982)): mp dec.>320° C. $^1$H NMR (300 MHz, DMSO-$d_6$) $\delta$ 7.261–7.075 (m, 4H, H-5+H-6+H-7+H-8). LRMS: 161 (M$^+$, 100%), 133 (50%).

3-(Hydroxyimino)-1,4-dihydroquinoxalin-2-one. An adaptation of the method of Harsanyi et al., *Liebigs Ann. Chem.* 190 (1973), was used. A mixture of 3-aminoquinoxalin-2(1H)-one (1) (100 mg, 0.620 mmol) and hydroxylamine hydrochloride (94 mg, 1.3 mmol; Aldrich Co.) in 5 mL of 1-butanol was heated to reflux. The resulting suspension was stirred under reflux for 12 h. The resulting suspension was cool to 25° C. A pale yellow precipitate appeared. The mixture was vacuum filtered and the solid was washed with EtOH (5×2 mL) and dried in vacuum at 60° C. overnight to yield 5 mg (42%) of 3-(hydroxyimino)-1,4-dihydroquinoxalin-2-one as a pale yellow solid mp dec.>330° C. $^1$H NMR (300 MHz, DMSO-$d_6$) $\delta$ 11.156 (br s, 1H, NOH), 10.776 (br s, 1H, NH), 9.878 (br s, 1H, NH), 7.258–6.813 (m, H, H-5+H-6+H-7+H-8). LRMS: 177 (M$^+$, 78%), 161 (100%).

Example 52

Preparation of 5-Chloro-7-trifluoromethyl-3-(hydroxyimino)-1,4-dihydroquinoxalin-2-one 5-Chloro-7-trifluoromethyl-3-aminoquinoxalin-2(1H)-one. An adaptation of the method of Burrell et al., *J. Chem. Soc. Perkin I.* 2707 (1973), was used. A mixture of 3-chloro-5-trifluoromethyl-1,2-phenylenediamine (420 mg, 2.00 mmol; Maybridge Co.) and ethyl thiooxamate (293 mg, 2.20 mmol; Aldrich Co.) in 4 mL of 1-butanol was heated to reflux. The resulting solution was stirred under reflux for 6 h. The resulting suspension was cool to 25° C. A pale yellow precipitate appeared. The mixture was vacuum filtered and the solid was washed with EtOH (5×2 mL) and dried in vacuum at 60° C. overnight to yield 50 mg (9.5%) of 5-chloro-7-trifluoromethyl-3-aminoquinoxalin-2(1H)-one (tentatively named as this since the regiochemistry is not sure) as a pale yellow solid: mp 270°–272° C. $^1$H NMR (300 MHz, DMSO-$d_6$) $\delta$ 12.043 (br s, 1H, NH), 7.561 (s, 1H, H-7), 7.463 (s, 1H, H-5). LRMS: 263 (M$^+$, 100%), 235 (50%).

5-Chloro-7-trifluoromethyl-3-(hydroxyimino)-1,4-dihydroquinoxalin-2-one. An adaptation of the method of Harsanyi et al., *Liebigs Ann. Chem.* 190 (1973), was used. A mixture of 5-chloro-7-trifluoromethyl-3-aminoquinoxalin-2(1H)-one (35 mg, 0.13 mmol) and hydroxylamine hydrochloride (20 mg, 0.29 mmol; Aldrich Co.) in 2 mL of 1-butanol was heated to reflux. The resulting suspension was stirred under reflux for 12 h. The resulting suspension was cool to 25° C., and added H$_2$O (5 mL). A pale yellow precipitate appeared. The mixture was vacuum filtered and the solid was washed with EtOH (5×2 mL) and dried in vacuum at 60° C. overnight to yield 25 mg (69%) of 5-chloro-7-trifluoromethyl-3-(hydroxyimino)-1,4-dihydroquinoxalin-2-one (tentatively named as this since the regiochemistry is not sure) as a pale yellow solid of a new compound: mp dec.>235° C. $^1$H NMR (300 MHz, DMSO-$d_6$) $\delta$ 11.199 (br s, 1H, NH), 10.932 (br s, 1H, NOH), 10.411 (br s, 1H, NH), 7.604 (s, 1H, H-7), 7.317 (s, 1H, H-5). LRMS: 279 (M$^+$, 100%), 249 (50%).

Example 53

Preparation of 5-Bromo-7-trifluoromethyl-3-(hydroxyimino)-1,4-dihydroquinoxalin-2-one 5-Bromo-7-trifluoromethyl-3-aminoquinoxalin-2(1H)-one. An adaptation of the method of Burrell et al., *J. Chem. Soc. Perkin I.* 2707 (1973), was used. A mixture of 3-bromo-5-trifluoromethyl-1,2-phenylenediamine (384 mg, 1.50 mmol; Maybridge Co.) and ethyl thiooxamate (220 mg, 1.70 mmol; Aldrich Co.) in 4 mL of 1-butanol was heated to reflux. The resulting solution was stirred under reflux for 6 h. The resulting suspension was cooled to 25 ° C. A pale yellow precipitate appeared. The mixture was vacuum filtered and the solid was washed with EtOH (5×2 mL) and dried in vacuum at 60° C. overnight to yield 125 mg (27.1%) of 5-bromo-7-trifluoromethyl-3-aminoquinoxalin-2(1H)-one (tentatively named as this since the regiochemistry is not sure) as a pale yellow solid of a new compound: mp dec.>267° C. $^1$H NMR (300 MHz, DMSO-d$^6$) $\delta$ 7.680 (s, 1H, H-7), 7.495 (s, 1H, H-5). LRMS: 307 (M$^+$, 100%), 280 (50%).

5-Bromo-7-trifluoromethyl-3-(hydroxyimino)-1,4-dihydroquinoxalin-2-one. An adaptation of the method of Harsanyi et al., *Liebigs Ann. Chem.* 190 (1973) was used. A mixture of 5-bromo-7-trifluoromethyl-3-aminoquinoxalin-2(1H)-one (75 mg, 0.24 mmol) and hydroxylamine hydrochloride (38 mg, 0.54 mmol; Aldrich Co.) in 3 mL of 1-butanol was heated to reflux. The resulting suspension was stirred under reflux for 12 h. The resulting suspension was cooled to 25° C., and H$_2$O was added (6 mL). A pale yellow precipitate appeared. The mixture was vacuum filtered and the solid was washed with EtOH (5×2 mL) and dried in vacuum at 60° C. overnight to yield 67 mg (86% ) of 5-bromo-7-trifluoromethyl-3-(hydroxyimino)-1,4-dihydroquinoxalin-2-one (tentatively named as this since the regiochemistry is not sure) as a pale yellow solid of a new compound: mp 221°–223° C. $^1$H NMR (300 MHz, DMSO-$d_6$) $\delta$ 11.205 (br s, 1H, NH), 10.393 (br s, 1H, NH), 7.639 (s, 1H, H-7), 7.435 (s, 1H, H-5). LRMS: 323 (M$^+$, 80%), 293 (100%).

Example 54

3,8-Dihydrocyclobuta[b]quinoxaline-1,2-dione

The method of Skujins and Webb, *Chem. Comm.* 598 (1968), was used. Squaric acid (114 mg, 1.00 mmol; Aldrich Co.) was dissolved in hot water (2 mL) and o-phenylenediamine (108 mg, 1.00 mmol; Aldrich Co.) was dissolved in warm H$_2$SO$_4$ (2 mL, 25% w/v). The mixture was heated at 90°–100° C. for 2–3 min, and then allowed to cool to 25° C. The dark brown precipitate was collected by vacuum filtration and washed with water (10×5 mL), ethanol (10×5 mL), acetone (10×5 mL) and ether (10×5 mL), yielding 105 mg (56.5%): mp dec.>325° C. (lit. mp dec.>330° C.; Skujins and Webb, *Chem. Comm.* 598 (1968)). $^1$H NMR (300 MHz, DMSO-d$_6$) δ 10.002 (s, 2H, 2 NH), 6.621–6.633 (m, 2H, H-4+H-7), 6.324–6.354 (m, 2H, H-5+H-6).

Example 55

Preparation of 6,7-Dichloro-3-(hydroxyimino)-1,4-dihydroquinoxalin-2-one 6,7-Dichloro-3-aminoquinoxalin-2(1H)-one. An adaptation of the method of Burrell et al., *J. Chem. Soc. Perkin I.* 2707 (1973), was used. A mixture of 4,5-dichloro-1,2-phenylenediamine (354 mg, 2.00 mmol; Aldrich Co.) and ethyl thiooxamate (333 mg, 2.50 mmol; Aldrich Co.) in 5 mL of ethanol was heated to reflux. The resulting brown solution was stirred under reflux for 10 h. The resulting brown suspension was cooled down to 25° C. A brown precipitate appeared. The mixture was vacuum filtered and the brown solid was washed with EtOH (5×2 mL) and dried in vacuum at 60° C. overnight to yield 92 mg (20%) of 6,7-dichloro-3-aminoquinoxalin-2(1H)-one: mp dec.>350° C. $^1$H NMR (300 MHz, DMSO-d$_6$) δ 12.261 (br s, 1H, NH), 7.421 (s, 1H, H-5), 7.252 (s, 1H, H-8). Mass: calcd. for C$_8$H$_5$Cl$_2$N$_3$O (M$^+$) M/z 228.9810, found 228.9820.

6,7-Dichloro-3-(hydroxyimino)-1,4-dihydroquinoxalin-2-one. An adaptation of the method of Harsanyi et al., *Liebigs Ann. Chem.* 190 (1973), was used. A mixture of 6,7-dichloro-3-aminoquinoxalin-2(1H)-one (50 mg, 0.22 mmol) and hydroxylamine hydrochloride (33 mg, 0.47 mmol; Aldrich Co.) in 2 mL of ethanol was heated to reflux. The resulting brown suspension was stirred under reflux for 12 h. The resulting brown suspension was allowed to cool to 25° C. A brown precipitate appeared. The mixture was vacuum filtered and the brown solid was washed with EtOH (5×2 mL) and dried in vacuum at 60° C. overnight to yield 42 mg (79%) of 6,7-dichloro-3-(hydroxyimino)-1,4-dihydroquinoxalin-2-one: mp dec.>270° C. $^1$H NMR (300 MHz, DMSO-d$_6$) δ 11.306 (br s, 1H, NH), 11.049 (br s, 1H, NH), 10.148 (br s, 1H, NOH), 7.403 (s, 1H, H-5), 7.018 (s, 1H, H-8). Mass: calcd. for C$_8$H$_5$Cl$_2$N$_3$O$_2$ (M$^+$) M/Z 244.9759, found 244.9769.

Having now fully described this invention, it will be understood to those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A compound selected from the group consisting of:

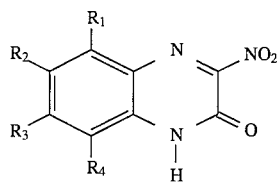

XXVI

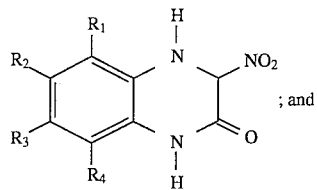

XXVII ; and

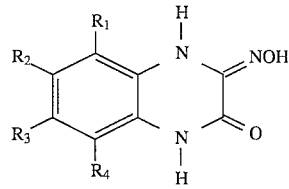

XLIX wherein R$_1$, R$_2$ and R$_3$ are independently selected from the group consisting of:
a) hydrogen,
b) C$_1$-C$_4$ alkyl,
c) nitro,
d) amino,
e) halo,
f) C$_1$-C$_4$ haloalkyl,
g) cyano,
h) C$_2$-C$_4$ alkenyl,
i) C$_2$-C$_4$ alkynyl,
j) alkanoylamino, where the alkyl portion of the alkanoyl moiety has from 1 to 4 carbon atoms,
k) azido,
l) C$_1$-C$_4$ alkoxy,
m) alkoxycarbonyl, where the alkoxy portion has from 1 to 4 carbon atoms, and
n) alkylcarbonyl, where the alkyl portion has from 1 to 4 carbon atoms; and R$_4$ is hydrogen or fluorine.

2. A compound selected from the group consisting of:

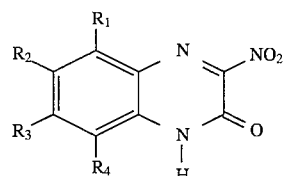

XXVI

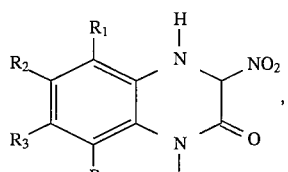

XXVII and

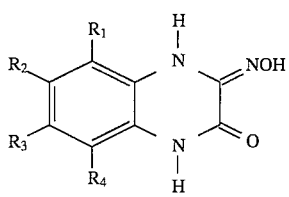

XLIX wherein
R$_1$ is one of nitro, amino, chloro, C$_1$ to C$_4$ alkyl or bromo;
R$_2$ is one of hydrogen, chloro, bromo, C$_1$ to C$_4$ alkyl or trifluoromethyl;
R$_3$ is one of nitro, chloro, bromo, C$_1$ to C$_4$ alkyl or trifluoromethyl; and
R$_4$ is hydrogen.

3. The compound of claim 1 wherein said compound is selected from the group consisting of:
1,2-dihydro-3-nitroquinoxaline-2-one;

1,2-dihydro-6,7-dichloro-3,5-dinitro-quinoxaline-2-one;
1,2-dihydro-6,7-dibromo-3,5-dinitro-quinoxaline-2-one;
1,2-dihydro-6,7-dimethyl-3,5-dinitro-quinoxaline-2-one;
1,2-dihydro-5,7-bis(trifluoromethyl)-3-nitro-quinoxaline-2-one;
1,2-dihydro-5,7-dimethyl-3-nitro-quinoxaline-2-one;
1,2-dihydro-5,7-dichloro-3-nitro-quinoxaline-2-one;
1,2-dihydro-5,7-difluoro-3-nitro-quinoxaline-2-one; and
1,2-dihydro-5,6,7-trichloro-3-nitro-quinoxaline-2-one.

4. The compound of claim 1 wherein said compound is selected from the group consisting of:
1,2,3,4-tetrahydro-3-nitro-quinoxaline-2-one;
1,2,3,4-tetrahydro-6,7-dichloro-3,5-dinitro-quinoxaline-2-one;
1,2,3,4-tetrahydro-6,7-dibromo-3,5-dinitro-quinoxaline-2-one;
1,2,3,4-tetrahydro-6,7-dimethyl-3,5-dinitro-quinoxaline-2-one;
1,2,3,4-tetrahydro-5,7-bis(trifluoromethyl)-3-nitro-quinoxaline-2-one;
1,2,3,4-tetrahydro-5,7-dimethyl-3-nitro-quinoxaline-2-one;
1,2,3,4-tetrahydro-5,7-dichloro-3-nitro-quinoxaline-2-one;
1,2,3,4-tetrahydro-5,7-difluoro-3-nitro-quinoxaline-2-one; and
1,2,3,4-tetrahydro-5,6,7-trichloro-3-nitro-quinoxaline-2-one.

5. The compound of claim 1 wherein said compound is selected from the group consisting of:
3-(hydroxyimino)-1,4-dihydroquinoxaline-2-one;
6,7-dichloro-5-nitro-3-(hydroxyimino)-1,4-dihydroquinoxaline-2-one;
6,7-dibromo-5-nitro-3-(hydroxyimino)-1,4-dihydroquinoxaline-2-one;
6,7-dimethyl-5-nitro-3-(hydroxyimino)-1,4-dihydroquinoxaline-2-one;
5,7-bis(trifluoromethyl)-3-(hydroxyimino)-1,4-dihydroquinoxaline-2-one;
5,7-dimethyl-3-(hydroxyimino)-1,4-dihydroquinoxaline-2-one;
5,7-dichloro-3-(hydroxyimino)-1,4-dihydroquinoxaline-2-one;
5,7-difluoro-3-(hydroxyimino)-1,4-dihydroquinoxaline-2-one; and
5,6,7-trichloro-3-(hydroxyimino)-1,4-dihydroquinoxaline-2-one.

6. The compound of claim 1 wherein said compound is 6,7-dichloro-3-(hydroxyimino)-1,4-dihydroquinoxalin-2-one.

* * * * *